(12) United States Patent
Babiarz et al.

US010577655B2

(10) Patent No.: US 10,577,655 B2
(45) Date of Patent: Mar. 3, 2020

(54) CELL FREE DNA DIAGNOSTIC TESTING STANDARDS

(71) Applicant: Natera, Inc., San Carlos, CA (US)

(72) Inventors: Joshua Babiarz, Castro Valley, CA (US); Bernhard Zimmermann, San Mateo, CA (US); Tudor Pompiliu Constantin, Berkeley, CA (US)

(73) Assignee: Natera, Inc., San Carlos, CA (US)

( * ) Notice: Subject to any disclaimer, the term of this patent is extended or adjusted under 35 U.S.C. 154(b) by 274 days.

(21) Appl. No.: 14/996,097

(22) Filed: Jan. 14, 2016

(65) Prior Publication Data

US 2016/0244838 A1    Aug. 25, 2016

Related U.S. Application Data

(63) Continuation-in-part of application No. 14/498,629, filed on Sep. 26, 2014, now Pat. No. 9,499,870, and a continuation-in-part of application No. 14/882,763, filed on Oct. 14, 2015, now Pat. No. 10,262,755, and a continuation-in-part of application No. 14/538,982, filed on Nov. 24, 2014, now Pat. No. 9,677,118, and a continuation-in-part of application No. 14/692,703, filed on Apr. 21, 2015, now Pat. No. 10,179,937.

(60) Provisional application No. 61/883,735, filed on Sep. 27, 2013, provisional application No. 61/978,658, filed on Apr. 11, 2014, provisional application No. 62/066,514, filed on Oct. 21, 2014, provisional application No. 62/146,188, filed on Apr. 10, 2015, provisional application No. 62/147,377, filed on Apr. 14, 2015, provisional application No. 62/148,173, filed on Apr. 15, 2015, provisional application No. 61/982,245, filed on Apr. 21, 2014, provisional application No. 61/987,407, filed on May 1, 2014, provisional application No. 61/994,791, filed on May 16, 2014, provisional application No. 62/066,514, filed on Oct. 21, 2014, provisional application No. 61/982,245, filed on Apr. 21, 2014, provisional application No. 61/987,407, filed on May 1, 2014, provisional application No. 62/066,514, filed on Oct. 21, 2014, provisional application No. 62/146,188, filed on Apr. 10, 2015, provisional application No. 62/147,377, filed on Apr. 14, 2015, provisional application No. 62/148,173, filed on Apr. 15, 2015, provisional application No. 61/994,791, filed on May 16, 2014.

(51) Int. Cl.
*C12Q 1/6883* (2018.01)
*C12Q 1/6806* (2018.01)
*C12N 15/10* (2006.01)

(52) U.S. Cl.
CPC ......... *C12Q 1/6883* (2013.01); *C12N 15/10* (2013.01); *C12Q 1/6806* (2013.01); *C12Q 2600/166* (2013.01); *Y10T 436/10* (2015.01)

(58) Field of Classification Search
CPC .............. C12Q 1/6883; C12Q 1/6806; C12Q 2600/166; C12Q 2600/156; C12Q 1/6886; C12Q 2600/16; C12N 15/10; Y10T 436/10

See application file for complete search history.

(56) References Cited

U.S. PATENT DOCUMENTS

| | | | |
|---|---|---|---|
| 5,635,366 A | 6/1997 | Cooke et al. |
| 5,716,776 A | 2/1998 | Bogart |
| 5,753,467 A | 5/1998 | Jensen et al. |
| 5,824,467 A | 10/1998 | Mascarenhas |
| 5,860,917 A | 1/1999 | Comanor et al. |
| 5,972,602 A | 10/1999 | Hyland et al. |
| 5,994,148 A | 11/1999 | Stewart et al. |
| 6,001,611 A | 12/1999 | Will |
| 6,025,128 A | 2/2000 | Veltri et al. |
| 6,066,454 A | 5/2000 | Lipshutz et al. |
| 6,100,029 A | 8/2000 | Lapidus et al. |
| 6,108,635 A | 8/2000 | Herren et al. |
| 6,124,120 A | 9/2000 | Lizardi |
| 6,143,496 A | 11/2000 | Brown et al. |
| 6,156,504 A | 12/2000 | Gocke et al. |
| 6,180,349 B1 | 1/2001 | Ginzinger et al. |
| 6,214,558 B1 | 4/2001 | Shuber et al. |
| 6,258,540 B1 | 7/2001 | Lo et al. |
| 6,300,077 B1 | 8/2001 | Shuber et al. |
| 6,479,235 B1 | 11/2002 | Schumm et al. |

(Continued)

FOREIGN PATENT DOCUMENTS

CN    1650032 A    8/2005
CN    1674028 A    9/2005

(Continued)

OTHER PUBLICATIONS

Jahr et al. Cancer Research. 2001. 61:1659-1665. (Year: 2001).*

(Continued)

*Primary Examiner* — Joseph G. Dauner

(57) ABSTRACT

Embodiments of the invention include methods and compositions for producing standards for noninvasive prenatal genetic diagnostics and for the detection and monitoring of cancer. The compositions can include a plurality of different nucleosomal DNA fragments derived from either primary cells or cell lines and can include one or more synthetic oligonucleotides. The amount of the different nucleosomal DNA fragments can be varied so as to simulate naturally occurring cell free DNA samples obtained from the blood of the pregnant woman or naturally occurring cell free DNA samples obtained from the blood of cancer patients.

9 Claims, 20 Drawing Sheets
Specification includes a Sequence Listing.

(56) References Cited

U.S. PATENT DOCUMENTS

| | | |
|---|---|---|
| 6,440,706 B1 | 12/2002 | Vogelstein et al. |
| 6,489,135 B1 | 12/2002 | Parrott et al. |
| 6,720,140 B1 | 4/2004 | Hartley et al. |
| 6,794,140 B1 | 9/2004 | Goldsborough |
| 6,807,491 B2 | 10/2004 | Pavlovic et al. |
| 6,852,487 B1 | 10/2005 | Barany et al. |
| 6,958,211 B2 | 10/2005 | Vingerhoets et al. |
| 6,964,847 B1 | 11/2005 | Englert |
| 7,035,739 B2 | 4/2006 | Schadt et al. |
| 7,058,517 B1 | 6/2006 | Denton et al. |
| 7,058,616 B1 | 6/2006 | Larder et al. |
| 7,218,764 B2 | 5/2007 | Vaisberg et al. |
| 7,297,485 B2 | 11/2007 | Bornarth et al. |
| 7,332,277 B2 | 2/2008 | Dhallan |
| 7,414,118 B1 | 8/2008 | Mullah et al. |
| 7,442,506 B2 | 12/2008 | Dhallan |
| 7,459,273 B2 | 12/2008 | Jones et al. |
| 7,645,576 B2 | 5/2010 | Lo et al. |
| 7,700,325 B2 | 5/2010 | Cantor et al. |
| 7,718,367 B2 | 5/2010 | Lo et al. |
| 7,718,370 B2 | 6/2010 | Dhallan |
| 7,727,720 B2 | 9/2010 | Dhallan |
| 7,805,282 B2 | 11/2010 | Casey et al. |
| 7,838,647 B2 | 11/2010 | Hahn et al. |
| 7,888,017 B2 | 8/2011 | Quake |
| 8,008,018 B2 | 9/2011 | Quake et al. |
| 8,024,128 B2 | 9/2011 | Rabinowitz |
| 8,133,719 B2 | 3/2012 | Drmanac et al. |
| 8,137,912 B2 | 5/2012 | Kapur et al. |
| 8,168,389 B2 | 5/2012 | Shoemaker et al. |
| 8,173,370 B2 | 5/2012 | Oeth et al. |
| 8,195,415 B2 | 10/2012 | Fan et al. |
| 8,296,076 B2 | 11/2012 | Fan et al. |
| 8,304,187 B2 | 11/2012 | Fernando |
| 8,318,430 B2 | 11/2012 | Chuu et al. |
| 8,450,063 B2 | 5/2013 | Dube et al. |
| 8,467,976 B2 | 8/2013 | Lo et al. |
| 8,515,679 B2 | 9/2013 | Rabinowitz et al. |
| 8,532,930 B2 | 9/2013 | Rabinowitz et al. |
| 8,682,592 B2 | 3/2014 | Rabinowitz et al. |
| 8,825,412 B2 | 9/2014 | Rabinowitz et al. |
| 9,085,798 B2 | 7/2015 | Chee |
| 9,323,888 B2 | 4/2016 | Rava et al. |
| 9,476,095 B2 | 10/2016 | Vogelstein et al. |
| 9,487,829 B2 | 11/2016 | Vogelstein et al. |
| 9,598,731 B2 | 3/2017 | Talasaz |
| 9,677,118 B2 | 6/2017 | Zimmermann et al. |
| 10,081,839 B2 | 9/2018 | Rabinowitz et al. |
| 10,083,273 B2 | 9/2018 | Rabinowitz et al. |
| 10,308,981 B2 | 6/2019 | Sparks et al. |
| 10,316,362 B2 | 6/2019 | Babiarz et al. |
| 2001/0051341 A1 | 12/2001 | Lo et al. |
| 2001/0053519 A1 | 12/2001 | Fodor et al. |
| 2002/0006622 A1 | 1/2002 | Bradley et al. |
| 2002/0107640 A1 | 8/2002 | Ideker et al. |
| 2003/0009295 A1 | 1/2003 | Markowitz et al. |
| 2003/0065535 A1 | 4/2003 | Karlov et al. |
| 2003/0077586 A1 | 4/2003 | Pavlovic et al. |
| 2003/0101000 A1 | 5/2003 | Bader et al. |
| 2003/0119004 A1 | 6/2003 | Wenz et al. |
| 2003/0228613 A1 | 12/2003 | Bornarth et al. |
| 2004/0033596 A1 | 2/2004 | Threadgill et al. |
| 2004/0137470 A1 | 7/2004 | Dhallan et al. |
| 2004/0146866 A1 | 7/2004 | Fu |
| 2004/0157243 A1* | 8/2004 | Huang ............. C12Q 1/6827 435/6.12 |
| 2004/0197797 A1 | 10/2004 | Inoko et al. |
| 2004/0209299 A1 | 10/2004 | Pinter et al. |
| 2004/0229231 A1 | 11/2004 | Frudakis et al. |
| 2004/0236518 A1 | 11/2004 | Pavlovic et al. |
| 2004/0259100 A1 | 12/2004 | Gunderson et al. |
| 2005/0009069 A1 | 1/2005 | Liu et al. |
| 2005/0049793 A1 | 3/2005 | Paterlini-Brechot |
| 2005/0053950 A1 | 3/2005 | Ubani et al. |
| 2005/0079535 A1 | 4/2005 | Kirchgesser et al. |
| 2005/0123914 A1 | 6/2005 | Katz et al. |
| 2005/0130173 A1 | 6/2005 | Leamon et al. |
| 2005/0142577 A1 | 6/2005 | Jones et al. |
| 2005/0144664 A1 | 6/2005 | Smith et al. |
| 2005/0164241 A1 | 7/2005 | Hahn et al. |
| 2005/0216207 A1 | 9/2005 | Kermani |
| 2005/0221341 A1 | 10/2005 | Shimkets et al. |
| 2005/0227263 A1 | 10/2005 | Green et al. |
| 2005/0250111 A1 | 11/2005 | Xie et al. |
| 2005/0255508 A1 | 11/2005 | Casey et al. |
| 2005/0272073 A1 | 12/2005 | Vaisberg et al. |
| 2006/0019278 A1 | 1/2006 | Lo et al. |
| 2006/0040300 A1 | 2/2006 | Dapprich et al. |
| 2006/0052945 A1 | 3/2006 | Rabinowitz et al. |
| 2006/0057618 A1 | 3/2006 | Piper et al. |
| 2006/0068394 A1 | 3/2006 | Langmore et al. |
| 2006/0088574 A1 | 4/2006 | Manning et al. |
| 2006/0099614 A1 | 5/2006 | Gill et al. |
| 2006/0121452 A1 | 6/2006 | Dhallan |
| 2006/0134662 A1 | 6/2006 | Pratt et al. |
| 2006/0141499 A1 | 6/2006 | Sher et al. |
| 2006/0229823 A1 | 8/2006 | Liu |
| 2006/0210997 A1 | 9/2006 | Myerson et al. |
| 2006/0216738 A1 | 9/2006 | Wada et al. |
| 2006/0248031 A1 | 11/2006 | Kates et al. |
| 2006/0281105 A1 | 12/2006 | Li et al. |
| 2007/0020640 A1 | 1/2007 | McCloskey et al. |
| 2007/0027636 A1 | 2/2007 | Rabinowitz |
| 2007/0042384 A1 | 2/2007 | Li et al. |
| 2007/0059707 A1 | 3/2007 | Cantor et al. |
| 2007/0122805 A1 | 5/2007 | Cantor et al. |
| 2007/0128624 A1 | 6/2007 | Gormley et al. |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0259351 A1 | 11/2007 | Chinitz |
| 2008/0020390 A1 | 1/2008 | Mitchell |
| 2008/0026390 A1 | 1/2008 | Stoughton et al. |
| 2008/0038733 A1 | 2/2008 | Bischoff et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0090239 A1 | 4/2008 | Shoemaker et al. |
| 2008/0096766 A1 | 4/2008 | Lee |
| 2008/0102455 A1 | 5/2008 | Poetter |
| 2008/0138809 A1 | 6/2008 | Kapur et al. |
| 2008/0182244 A1 | 7/2008 | Tafas et al. |
| 2008/0193927 A1 | 8/2008 | Mann et al. |
| 2008/0220422 A1 | 9/2008 | Shoemaker et al. |
| 2008/0234142 A1 | 9/2008 | Lietz |
| 2008/0243398 A1 | 10/2008 | Rabinowitz et al. |
| 2008/0305473 A1 | 12/2008 | Chowdary et al. |
| 2009/0023190 A1 | 1/2009 | Lao et al. |
| 2009/0029377 A1 | 1/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0143570 A1 | 6/2009 | Jiang et al. |
| 2009/0176662 A1 | 7/2009 | Rigatti et al. |
| 2009/0221620 A1 | 9/2009 | Luke et al. |
| 2009/0317817 A1 | 12/2009 | Oeth et al. |
| 2010/0035232 A1 | 2/2010 | Ecker et al. |
| 2010/0112575 A1 | 5/2010 | Fan et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0129874 A1 | 5/2010 | Mitra et al. |
| 2010/0138165 A1 | 6/2010 | Fan et al. |
| 2010/0171954 A1 | 7/2010 | Quake et al. |
| 2010/0184069 A1 | 7/2010 | Fernando et al. |
| 2010/0184152 A1 | 7/2010 | Sandler |
| 2010/0196892 A1 | 8/2010 | Quake et al. |
| 2010/0203538 A1 | 8/2010 | Dube et al. |
| 2010/0216153 A1 | 8/2010 | Lapidus et al. |

(56) References Cited

U.S. PATENT DOCUMENTS

| | | |
|---|---|---|
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0273678 A1 | 10/2010 | Alexandre et al. |
| 2010/0285537 A1 | 11/2010 | Zimmermann |
| 2010/0291572 A1 | 11/2010 | Stoughton et al. |
| 2010/0291635 A1 | 11/2010 | Peleg |
| 2010/0323352 A1 | 12/2010 | Lo et al. |
| 2011/0033862 A1 | 2/2011 | Rabinowitz et al. |
| 2011/0039724 A1 | 2/2011 | Lo et al. |
| 2011/0071031 A1 | 3/2011 | Khripin et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0151442 A1 | 6/2011 | Fan et al. |
| 2011/0159499 A1 | 6/2011 | Hindson et al. |
| 2011/0160078 A1 | 6/2011 | Fodor et al. |
| 2011/0178719 A1 | 7/2011 | Rabinowitz et al. |
| 2011/0201507 A1 | 8/2011 | Rava et al. |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0300608 A1 | 12/2011 | Ryan et al. |
| 2011/0301854 A1 | 12/2011 | Curry et al. |
| 2011/0318734 A1 | 12/2011 | Lo et al. |
| 2012/0003635 A1 | 1/2012 | Lo et al. |
| 2012/0010085 A1 | 1/2012 | Rava et al. |
| 2012/0034603 A1 | 2/2012 | Oliphant et al. |
| 2012/0034685 A1 | 2/2012 | Sparks et al. |
| 2012/0108460 A1 | 5/2012 | Quake et al. |
| 2012/0122701 A1 | 5/2012 | Ryan et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0191358 A1 | 7/2012 | Oliphant et al. |
| 2012/0196754 A1 | 8/2012 | Quake et al. |
| 2012/0214678 A1 | 8/2012 | Rava et al. |
| 2012/0264121 A1 | 10/2012 | Rava et al. |
| 2012/0270212 A1 | 10/2012 | Rabinowitz et al. |
| 2012/0295810 A1 | 11/2012 | Quake et al. |
| 2012/0295819 A1 | 11/2012 | Leamon et al. |
| 2013/0017549 A1 | 1/2013 | Hong |
| 2013/0024127 A1 | 1/2013 | Stuelpnagel |
| 2013/0034546 A1 | 2/2013 | Rava et al. |
| 2013/0060483 A1 | 3/2013 | Struble et al. |
| 2013/0069869 A1 | 3/2013 | Akao et al. |
| 2013/0090250 A1 | 4/2013 | Sparks et al. |
| 2013/0116130 A1 | 5/2013 | Fu et al. |
| 2013/0123120 A1 | 5/2013 | Zimmermann et al. |
| 2013/0130923 A1 | 5/2013 | Ehrich et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0252824 A1 | 9/2013 | Rabinowitz et al. |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0303461 A1 | 11/2013 | Iafrate et al. |
| 2013/0323731 A1 | 12/2013 | Lo et al. |
| 2013/0325360 A1 | 12/2013 | Deciu et al. |
| 2014/0032128 A1 | 1/2014 | Rabinowitz et al. |
| 2014/0038830 A1 | 2/2014 | Srinivasan et al. |
| 2014/0051585 A1 | 2/2014 | Prosen et al. |
| 2014/0065621 A1 | 3/2014 | Mhatre et al. |
| 2014/0087385 A1 | 3/2014 | Rabinowitz et al. |
| 2014/0094373 A1 | 4/2014 | Zimmermann et al. |
| 2014/0100126 A1 | 4/2014 | Rabinowitz |
| 2014/0100134 A1 | 4/2014 | Rabinowitz et al. |
| 2014/0141981 A1 | 5/2014 | Zimmermann et al. |
| 2014/0154682 A1 | 6/2014 | Rabinowitz et al. |
| 2014/0155274 A1 | 6/2014 | Xie et al. |
| 2014/0162269 A1 | 6/2014 | Rabinowitz |
| 2014/0193816 A1 | 7/2014 | Rabinowitz et al. |
| 2014/0206552 A1 | 7/2014 | Rabinowitz et al. |
| 2014/0227705 A1 | 8/2014 | Vogelstein et al. |
| 2014/0256558 A1 | 9/2014 | Varley et al. |
| 2014/0256569 A1 | 9/2014 | Rabinowitz et al. |
| 2014/0272956 A1 | 9/2014 | Huang et al. |
| 2014/0287934 A1 | 9/2014 | Szelinger et al. |
| 2014/0329245 A1 | 11/2014 | Spier et al. |
| 2014/0336060 A1 | 11/2014 | Rabinowitz |
| 2015/0051087 A1 | 2/2015 | Rabonowitz et al. |
| 2015/0064695 A1 | 3/2015 | Katz et al. |
| 2015/0147815 A1 | 5/2015 | Babiarz et al. |
| 2015/0197786 A1 | 7/2015 | Osborne et al. |
| 2015/0232938 A1 | 8/2015 | Mhatre |
| 2015/0265995 A1 | 9/2015 | Head et al. |
| 2016/0145682 A1 | 5/2016 | Woodward et al. |
| 2016/0201124 A1 | 7/2016 | Donahue et al. |
| 2016/0257993 A1 | 9/2016 | Fu et al. |
| 2016/0289740 A1 | 10/2016 | Fu et al. |
| 2016/0289753 A1 | 10/2016 | Osborne et al. |
| 2016/0312276 A1 | 10/2016 | Fu et al. |
| 2016/0319345 A1 | 11/2016 | Gnerre et al. |
| 2016/0369333 A1 | 12/2016 | Babiarz et al. |
| 2017/0121716 A1 | 5/2017 | Rodi et al. |
| 2017/0342477 A1 | 11/2017 | Jensen et al. |
| 2018/0148777 A1 | 5/2018 | Kirkizlar et al. |
| 2018/0155775 A1 | 6/2018 | Zimmermann et al. |
| 2018/0155776 A1 | 6/2018 | Zimmermann et al. |
| 2018/0155779 A1 | 6/2018 | Zimmermann et al. |
| 2018/0155785 A1 | 6/2018 | Rabinowitz et al. |
| 2018/0155786 A1 | 6/2018 | Rabinowitz et al. |
| 2018/0155792 A1 | 6/2018 | Rabinowitz et al. |
| 2018/0171409 A1 | 6/2018 | Rabinowitz et al. |
| 2018/0171420 A1 | 6/2018 | Babiarz et al. |
| 2018/0173845 A1 | 6/2018 | Sigurjonsson et al. |
| 2018/0173846 A1 | 6/2018 | Sigurjonsson et al. |
| 2018/0201995 A1 | 7/2018 | Rabinowitz et al. |
| 2018/0237841 A1 | 8/2018 | Stray et al. |
| 2018/0298439 A1 | 10/2018 | Ryan et al. |
| 2018/0300448 A1 | 10/2018 | Rabinowitz et al. |
| 2019/0010543 A1 | 1/2019 | Babiarz et al. |
| 2019/0106737 A1 | 4/2019 | Underhill |
| 2019/0106751 A1 | 4/2019 | Zimmermann et al. |
| 2019/0185913 A1 | 6/2019 | Zimmermann et al. |
| 2019/0185936 A1 | 6/2019 | Babiarz et al. |
| 2019/0194743 A1 | 6/2019 | Ryan et al. |
| 2019/0194758 A1 | 6/2019 | Babiarz et al. |
| 2019/0194759 A1 | 6/2019 | Babiarz et al. |
| 2019/0203290 A1 | 7/2019 | Rabinowitz et al. |
| 2019/0203294 A1 | 7/2019 | Babiarz et al. |
| 2019/0211391 A1 | 7/2019 | Rabinowitz et al. |
| 2019/0211392 A1 | 7/2019 | Rabinowitz et al. |
| 2019/0211393 A1 | 7/2019 | Rabinowitz et al. |
| 2019/0211399 A1 | 7/2019 | Rabinowitz et al. |
| 2019/0211402 A1 | 7/2019 | Babiarz et al. |
| 2019/0211406 A1 | 7/2019 | Babiarz et al. |
| 2019/0249241 A1 | 8/2019 | Rabinowitz et al. |
| 2019/0256894 A1 | 8/2019 | Zimmermann et al. |
| 2019/0256906 A1 | 8/2019 | Rabinowitz et al. |
| 2019/0256907 A1 | 8/2019 | Ryan et al. |
| 2019/0256908 A1 | 8/2019 | Rabinowitz et al. |
| 2019/0256909 A1 | 8/2019 | Rabinowitz et al. |
| 2019/0256912 A1 | 8/2019 | Rabinowitz et al. |
| 2019/0256916 A1 | 8/2019 | Babiarz et al. |
| 2019/0256917 A1 | 8/2019 | Babiarz et al. |
| 2019/0256919 A1 | 8/2019 | Babiarz et al. |
| 2019/0256931 A1 | 8/2019 | Babiarz et al. |
| 2019/0264277 A1 | 8/2019 | Rabinowitz et al. |
| 2019/0264280 A1 | 8/2019 | Rabinowitz et al. |
| 2019/0264288 A1 | 8/2019 | Rabinowitz et al. |
| 2019/0271043 A1 | 9/2019 | Babiarz et al. |
| 2019/0276888 A1 | 9/2019 | Rabinowitz et al. |
| 2019/0284623 A1 | 9/2019 | Rabinowitz et al. |
| 2019/0300950 A1 | 10/2019 | Rabinowitz et al. |
| 2019/0309358 A1 | 10/2019 | Rabinowitz et al. |
| 2019/0309359 A1 | 10/2019 | Zimmermann et al. |
| 2019/0309365 A1 | 10/2019 | Babiarz et al. |
| 2019/0316177 A1 | 10/2019 | Zimmermann et al. |

(56) References Cited

U.S. PATENT DOCUMENTS

| | | |
|---|---|---|
| 2019/0316184 A1 | 10/2019 | Zimmermann et al. |
| 2019/0316200 A1 | 10/2019 | Rabinowitz et al. |
| 2019/0323076 A1 | 10/2019 | Rabinowitz et al. |
| 2019/0360036 A1 | 11/2019 | Rabinowitz et al. |

FOREIGN PATENT DOCUMENTS

| | | |
|---|---|---|
| CN | 101675169 A | 3/2010 |
| EP | 0270017 A2 | 6/1988 |
| EP | 1524321 A1 | 4/2005 |
| EP | 1524321 B1 | 7/2009 |
| EP | 2163622 A1 | 3/2010 |
| EP | 2902500 A1 | 8/2015 |
| EP | 3285193 A1 | 2/2018 |
| GB | 2488358 | 8/2012 |
| JP | 2965699 | 8/1999 |
| JP | 2002-530121 A | 9/2002 |
| JP | 2004502466 A | 1/2004 |
| JP | 2004533243 A | 11/2004 |
| JP | 2005514956 A | 5/2005 |
| JP | 2005160470 A | 6/2005 |
| JP | 2006-254912 A | 9/2006 |
| JP | 2011/516069 A | 5/2011 |
| RU | 2290078 C1 | 12/2006 |
| WO | 179851 A1 | 10/2001 |
| WO | 200190419 A2 | 11/2001 |
| WO | 2002004672 A2 | 1/2002 |
| WO | 2002055985 A2 | 7/2002 |
| WO | 2002076377 | 10/2002 |
| WO | 2003031646 A1 | 4/2003 |
| WO | 3050532 A1 | 6/2003 |
| WO | 2003062441 A1 | 7/2003 |
| WO | 0190419 A9 | 11/2003 |
| WO | 3102595 A1 | 12/2003 |
| WO | 3106623 A2 | 12/2003 |
| WO | 2004087863 A2 | 10/2004 |
| WO | 2005021793 A1 | 3/2005 |
| WO | 2005035725 A2 | 4/2005 |
| WO | 2005100401 A2 | 10/2005 |
| WO | 2005123779 A2 | 12/2005 |
| WO | 2007057647 A1 | 5/2007 |
| WO | 2007062164 A3 | 5/2007 |
| WO | 2007070482 A2 | 6/2007 |
| WO | 2007/117256 A1 | 10/2007 |
| WO | 2007132167 A2 | 11/2007 |
| WO | 2007/147076 A2 | 12/2007 |
| WO | 2007147074 A2 | 12/2007 |
| WO | 2008024473 A2 | 2/2008 |
| WO | 2008048931 A1 | 4/2008 |
| WO | 2008051928 A2 | 5/2008 |
| WO | 2008059578 A1 | 5/2008 |
| WO | 2008081451 A2 | 7/2008 |
| WO | 2008115497 A2 | 9/2008 |
| WO | 2008135837 A2 | 11/2008 |
| WO | 2008157264 A2 | 12/2008 |
| WO | 2009009769 A2 | 1/2009 |
| WO | 2009013492 A1 | 1/2009 |
| WO | 2009013496 A1 | 1/2009 |
| WO | 2009019215 A1 | 2/2009 |
| WO | 2009019455 A2 | 2/2009 |
| WO | 2009/036525 A2 | 3/2009 |
| WO | 2009030100 A1 | 3/2009 |
| WO | 2009032779 A2 | 3/2009 |
| WO | 2009032781 A2 | 3/2009 |
| WO | 2009033178 A1 | 3/2009 |
| WO | 2009091934 A1 | 7/2009 |
| WO | 2009092035 A2 | 7/2009 |
| WO | 2009105531 A1 | 8/2009 |
| WO | 2009146335 A1 | 12/2009 |
| WO | 2010017214 A1 | 2/2010 |
| WO | 2010/033652 A1 | 3/2010 |
| WO | 2010075459 | 7/2010 |
| WO | 2011041485 A1 | 4/2011 |
| WO | 2011/057061 A1 | 5/2011 |
| WO | 2011057094 | 5/2011 |
| WO | 2011/090556 A1 | 7/2011 |
| WO | 2011087760 | 7/2011 |
| WO | 2011146632 A1 | 11/2011 |
| WO | 2012/019200 A2 | 2/2012 |
| WO | 2012/028746 A1 | 3/2012 |
| WO | 201283250 | 6/2012 |
| WO | 2012088456 A2 | 6/2012 |
| WO | 20120071621 | 6/2012 |
| WO | 2012108920 A1 | 8/2012 |
| WO | 2012/142531 A2 | 10/2012 |
| WO | 2007/149791 A2 | 12/2012 |
| WO | 2013030577 | 3/2013 |
| WO | 2013/045432 A1 | 4/2013 |
| WO | 2013/049892 A1 | 4/2013 |
| WO | 2013052557 A2 | 4/2013 |
| WO | 2013/078470 A2 | 5/2013 |
| WO | 2013/086464 A1 | 6/2013 |
| WO | 20130130848 | 9/2013 |
| WO | 2013/159035 A2 | 10/2013 |
| WO | 2013/181651 A1 | 12/2013 |
| WO | 2014/004726 A1 | 1/2014 |
| WO | 2014/014497 A1 | 1/2014 |
| WO | 20140018080 | 1/2014 |
| WO | 2014/035986 A1 | 3/2014 |
| WO | 2014/122288 A1 | 8/2014 |
| WO | 2014/149134 A2 | 9/2014 |
| WO | 2014/151117 A1 | 9/2014 |
| WO | 2015/100427 A1 | 7/2015 |
| WO | 2015/164432 A1 | 10/2015 |
| WO | 2016/009059 A1 | 1/2016 |
| WO | 2016/065295 A1 | 4/2016 |
| WO | 2016/138080 A1 | 9/2016 |
| WO | 2016/193490 A1 | 12/2016 |
| WO | 2017/058784 A1 | 4/2017 |
| WO | 2017/181146 A1 | 10/2017 |
| WO | 2017/181202 A2 | 10/2017 |
| WO | 2018/083467 A1 | 5/2018 |
| WO | 2018/106798 A1 | 6/2018 |
| WO | 2018/156418 A1 | 8/2018 |
| WO | 2019/140298 A1 | 7/2019 |
| WO | 2019/161244 A1 | 8/2019 |
| WO | 2019/200228 A1 | 10/2019 |

OTHER PUBLICATIONS

CanSAR. Retrieved on Mar. 26, 2018 from the internet: https://cansar.icr.ac.uk/cansar/cell-lines/Hs-578-T/copy_number_variation/chromosome_8/.*

Mamon et al. Clinical Chemistry. 2008. 54(9):1582-1584. (Year: 2008).*

Allan et al. Journal of Molecular Biology. 2012. 417:152-164 (Year: 2012).*

Widlak et al. The Journal of Biological Chemistry. 2000. 275(11):8226-8232. (Year: 2000).*

Hall, Megan P. "Panorama Non-Invasive Prenatal Screening for Microdeletion Syndromes". 2014. (Year: 2014).*

Wapner et al. American Journal of Obstetrics and Gynecology. 2014. vol. 212. (Year: 2014).*

"Random variable", In the Penguin Dictionary of Mathematics. Retrieved from http://www.credoreference.com/entry/penguinmath/random _variable, 2008, 1 page.

Casbon, J. A. et al., "A method for counting PCR template molecules with application to next-generation sequencing", Nucleic Acids Research, vol. 39, No. 12, Apr. 13, 2011, 1-8.

Craig, D. W. et al., "Identification of genetic variants using barcoded multiplexed sequencing", Nature Methods, vol. 5, Oct. 2008, 887-893.

Fan, H. Christina et al., "Sensitivity of Noninvasive Prenatal Detection of Fetal Aneuploidy from Maternal Plasma Using Shotgun Sequencing Is Limited Only by Counting Statistics", PLoS One, vol. 5, Issue 5 (e10439), May 3, 2010, 1-6.

Fu, G. K. et al., "Counting individual DNA molecules by the stochastic attachment of diverse labels", PNAS, vol. 108, No. 22, May 31, 2011, 9026-9031.

(56) References Cited

OTHER PUBLICATIONS

Fu, G. K. et al., "Digital Encoding of Cellular mRNAs Enabling Precise and Absolute Gene Expression Measurement by Single-Molecule Counting", Analytical Chemistry, vol. 86, Mar. 3, 2014, 2867-2870.

Hollas, B. et al., "A stochastic approach to count RN A molecules using DNA sequencing methods", Lecture Notes in Computer Science, vol. 2812, 2003, 55-62.

Hug, H. et al., "Measurement of the number of molecules of a single mRNA species in a complex mRNA preparation", J. Theor. Biol., vol. 221, 2003, 615-624.

Hultin, E. et al., "Competitive enzymatic reaction to control allele-specific extensions", Nucleic Acids Research, vol. 33, No. 5, Mar. 14, 2005, 1-10.

Jabara, C. B. et al., "Accurate sampling and deep sequencing of the HIV-1 protease gene using a Primer ID", PNAS, vol. 108, No. 50, Dec. 13, 2011, 20166-20171.

Kinde, I. et al., "Detection and quantification of rare mutations with massively parallel sequencing", PNAS, vol. 108, No. 23, Jun. 7, 2011, 9530-9535.

Kivioja, T. et al., "Counting absolute numbers of molecules using unique molecular identifiers", Nature Methods, Advance Online Publication, Nov. 20, 2011, 1-5.

McCloskey, M. L. et al., "Encoding PCR Products with Batch-stamps and Barcodes", Biochem Genet., vol. 45, Oct. 23, 2007, 761-767.

Merriam-Webster, "Medical Definition of Stimulant", http://www.merriam-webster.com/medical/stimulant, Mar. 14, 2016, 7 pages.

Miner, B. E. et al., "Molecular barcodes detect redundancy and contamination in hairpin-bisulfite PCR", Nucleic Acids Research, vol. 32, No. 17, Sep. 30, 2004, 1-4.

Munne, S. et al., "Chromosome Abnormalities in Human Embryos", Textbook of Assisted Reproductive Techniques, 2004, pp. 355-377.

Ragoussis, J. , "Genotyping Technologies for Genetic Research", Annual Review of Genomics and Human Genetics, vol. 10 (1), Sep. 1, 2009, 117-133.

Schmitt, M. W. et al., "Detection of ultra-rare mutations by next-generation sequencing", PNAS, vol. 109, No. 36, Sep. 4, 2012, 14508-14513.

Shiroguchi, K. et al., "Digital RNA sequencing minimizes sequence-dependent bias and amplification noise with optimized single-molecule barcodes", PNAS, vol. 109, No. 4, Jan. 24, 2012, 1347-1352.

Taliun, D. et al., "Efficient haplotype block recognition of very long and dense genetic sequences", BMC Bioinformatics, vol. 15 (10), 2014, 1-18.

McBride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.

Popova, T. et al., "Genome Alteration Print (GAP): a tool to visualize and mine complex cancer genomic profiles obtained by SNP arrays", Genome Biology, vol. 10, R128, Nov. 11, 2009, 1-14.

"Blast of AAAAAAAAATTTAAAAAAAAATTT(http://blast.ncbi.nlm.nih.gov/Blast.cgi, downloaded May 4, 2015)".

"CompetitivePCR Guide,", TaKaRa Biomedicals, Lit. #L0126 Rev. 8/99, 9 pgs.

"Db SNP rs2056688 (http://www.ncbi.nlm.nih.gov/projects/SNP/snp_ref.cgi?rs=2056688, downloaded May 4, 2015".

"Declaration by Dr. Zimmerman of Oct. 30, 2014 filed in U.S. Appl. No. 14/044,434".

"European Application No. 014198110, European Search Report dated Apr. 28, 2015, 3 pages."

"Finishing the Euchromatic Sequence of the Human Genome", Nature vol. 43, (Oct. 21, 2004),931-945.

"Fixed Medium, dictionary definition, Academic Press Dictionary of Science andTechnology", Retrieved from the Internet: <URL:www.credoreference.com/entry/apdst/fixed_medium>, 1996, 1 pg.

"Genetics Home Reference", http://ghr.nlm.nihg.gov/handbook/genomicresearch/snp, Feb. 28, 2014, 1-2.

"Guideline related to genetic examination", Societies Related to Genetic Medicine, Japanese Society for Genetic Counseling, Japanese Society for Gene Diagnosis and Therapy, Japan Society of Obstetrics an, 2003, 2-15.

"How Many Carbs in a Potato? [Online]", Retrieved from theInternet. <http://www.newhealthguide.org/How-Many-Carbs-In-A-Potato.html>, Nov. 1, 2014, 3 pgs.

"Ion Ampli Seq Comprehensive Cancer Panel, product brochure, Life TechnologiesCorporation. Retrieved from the Internet", <URL:https://tools.lifetechnologies.com/content/sfs/brochures/Ion_CompCancerPanel_Flyer.pdf>, 2012, 2 pgs.

"IonAmpliSeq Designer Provides Full Flexibility to Sequence Genes of Your Choice,product brochure, Life Technologies Corporation", Retrieved from the Internet<URL: http://tools.lifetechnologies.com/content/sfs/brochures/IonAmpliSeq_CustomPanels_AppNote_CO1.

"Merriam-Webster.com (http://www.merriam-webster.com/dictionary/universal, downloaded Jul. 23, 2014)".

"Multiplexing with RainDrop Digital PCR", RainDance Technologies, Application Note, 2013, 1-2.

"NucleicAcids, Linkers and Primers: Random Primers", New England BioLabs 1998/99Catalog, 1998, 121 and 284.

"PRIMER3, information sheet, Sourceforge.net, [retrieved on Nov. 12, 2012]. Retrieved from the Internet: <URL: http://primer3.sourceforge.net/>", 2009, 1 pg.

"www.fatsecret.com" (printed from internet Nov. 1, 2014).

PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010).

The Bump (Panorama Test, attached, Jul. 1, 2013).

What to Expect (Weird Harmony results, attached, May 1, 2015).

Wikipedia (attached, available at https://en.wikipedia.org/wiki/Stimulant, accessed Mar. 14, 2016).

Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.

Agarwal, Ashwin. et al., "Commercial Landscape of Noninvasive Prenatal Testing in the United States", Prenatal Diagnosis,33, 2013, 521-531.

Alkan, Can et al., "Personalized Copy Number and Segmental Duplication Maps Using Next-Generation Sequencing", Nature Genetics, 41, 10, 2009, 1061-1068.

Allaire, F R., "Mate selection by selection index theory", Theoretical Applied Genetics, 57(6), 1980, 267-272.

Allawi, Hatim T. et al., "Thermodynamcs of internal C•T Mismatches in DNA", Nucleic Acids Research, 26 (11), 1998, 2694-2701.

Aoki, Yasuhiro, "Statistical and Probabilistic Bases of Forensic DNA Testing", The Journal of the Iwate Medical Association, 2002, vol. 54, p. 81-94.

Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.

Ashoor, Ghalia, et al., "Chromosome-Selective Sequencing of Maternal Plasma Cell-Free, DNA for First-Trimester Detection of Trisomy 21 and Trisomy 18", American Journal of Obstetrics & Gynecology, 206, 2012, 322.e1-322.e5.

Bada, Michael A. et al., "Computational Modeling of Structural Experimental Data", Methods in Enzymology,317, 2000, 470-491.

Beaumont, Mark A et al., "The Bayesian Revolution in Genetics", Nature Reviews Genetics, 5, 2004, 251-261.

Beer, Alan E. et al., "The Biological Basis of Passage of Fetal Cellular Material into the Maternal Circulation", Annals New York Academy of Sciences, 731, 1994, 21-35.

Beerenwinkel, et al., "Methods for Optimizing Antiviral Combination Therapies", Bioinformatics, 19(1), 2003, i16-i25.

Beerenwinkel, N. et al., "Geno2pheno: estimating phenotypic drug resistance from HIV-1 genotypes", Nucleic Acids Research, 31(13), 2003, 3850-3855.

(56) References Cited

OTHER PUBLICATIONS

Benn, P. et al., "Non-Invasive Prenatal Testing for Aneuploidy: Current Status and Future Prospects", Ultrasound Obstet Gynecol, 42, 2013, 15-33.
Benn, P et al., "Non-Invasive prenatal Diagnosis for Down Syndrome: the Paradigm Will Shift, but Slowly", Ultrasound Obstet. Gynecol., 39, 2012, 127-130.
Bentley, David R et al., "Accurate Whole Human Genome Sequencing Using Reversible Terminator Chemistry", Nature, 456, 6, 2008, 53-59.
Bermudez, M. et al., "Single-cell Sequencing and mini-sequencing for preimplantation genetic diagnosis", Prenatal Diagnosis, 23, 2003, 669-677.
Bevinetto, Gina, Bevinetto (5 Foods All Pregnant Women Need, American Baby, available at http://www.parents.com/pregnancy/mybody/nutrition/5greatpregnancyfoods/, Apr. 15, 2008.
Bianchi, D W. et al., "Fetal gender and aneuploidy detection using fetal cells maternal blood: analysis of NIFTY I data", Prenat Diagn 2002; 22, 2002, 609-615.
Birch, Lyndsey et al., "Accurate and Robust Quantification of Circulating Fetal and Total DNA in Maternal Plasma from 5 to 41 Weeks of Gestation", Clinical Chemistry, 2005, 312-320.
Bisignano, et al., "PGD and Aneuploidy Screening for 24 Chromosomes: Advantages and Disadvantages of Competing Platforms", Reproductive BioMedicine Online, 23, 2011, 677-685.
Bodenreider, O., "The Unified Medical Language System (UMLS): Integrating Biomedical Terminology", Nucleic Acids Research, 32, (Database issue), 2004, D267-D270.
Breithaupt, Holger, "The Future of Medicine", EMBO Reports, 21(61), 2001, 465-467.
Brownie, Jannine et al., "The Elimination of Primer-Dimer Accumulation in PCR", Nucleic Acids Research, 25(16), 1997, 3235-3241.
Cairns, Paul et al., "Homozygous Deletions of 9b21 in Primary Human Bladder Tumors Detected by Comparative Multiplex Polymerase Chain Reaction", Cancer Research, 54, 1994, 1422-1424.
Caliendo, Angela, "Multiplex PCR and Emerging Technologies for the Detection of Respiratory Pathogens", Clinical Infectious Diseases, 52(4), 2011, S326-S330.
Carnevale, Alessandra et al., "Attitudes of Mexican Geneticists Towards Prenatal Diagnosis and Selective Abortion", American Journal of Medical Genetics, 75, 1998, 426-431.
Chakraborty, R. et al., "Paternity Excusion by DNA Markers: Effects of Paternal Mutations", Journal of Forensic Sciences, vol. 41, No. 4, Jul. 1996, 671-677.
Chen, E. et al., "Noninvasive Prenatal Diagnosis of Fetal Trisomy 18 and Trisomy 13 by Maternal Plasma DNA Sequencing", PLoS ONE, 6(7), e21791, 2011, 7 pgs.
Chetty, Shilpa. et al., "Uptake of Noninvasive Prenatal Testing (NIPT) in Women Following Positive Aneuploidy Screening", Prenatal Diagnosis,33, 2013, 542-546.
Chiu, R. et al., "Non-Invasve Prenatal Assessment of Trisomy 21 by Multiplexed Maternal Plasma DNA Sequencing: Large Scale Validity Study", BMJ, 342, c7401, 2011, 9 pgs.
Chiu, Rossa W. et al., "Effects of Blood-Processing Protocols on Fetal and Total DNA Quantification in Maternal Plasma", Clinical Chemistry, 47(9), 2001, 1607-1613.
Chiu, Rossa W.K. et al., "Maternal Plasma DNA Analysis with Massively Parallel Sequencing by Litigation for Noninvasive Prenatal Diagnosis of Trisomy 21", Clinical Chemistry, 56, 3, 2010, 459-463.
Chiu, Rossa W.K. et al., "Noninvasive Prenatal Diagnosis of Fetal Chromosomal Aneuploidy by Massively Parallel Genomic Sequencing of DNA in Maternal Plasma", PNAS, 105, 51 (with Supporting Information), 2008, 23.
Chiu, Rossa W.K. et al., "Non-Invasive Prenatal Diagnosis by Single Molecule Counting Technologies", Trends in Genetics, 25 (7), 2009, 324-331.

Chu, T. et al., "Statistical Considerations for Digital Approaches to Non-Invasive Fetal Genotyping", Bioinformatics (Advance Access publication), 26 (22), 2010, 2863-2866.
Chu, Tianjiao et al., "Statistical Model for Whole Genome Sequencing and its Application to Minimally Invasive Diagnosis of Fetal Genetic Disease", Bioinformatics, 25(10), 2009, 1244-1250.
Chu, Tianjiao. et al., "A Novel Approach Toward the Challenge of Accurately Quantifying Fetal DNA in Maternal Plasma", Prenatal Diagnosis,30, 2010, 1226-1229.
Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.
Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.
Cossu, Gianfranco et al., "Rh D/d Genotyping by Quantitative Polymerase Chain Reaction and Capillary Zone Electrophoresis", Electrophoresis, 17, 1996, 1911-1915.
Coyle, J. F. et al., "Standards for detailed models as the basis for medical data exchange and decision support", International Journai of Medical Informatics, 69(2-3), 2003, 157-174.
Cross, Jillian et al., "Resolution of trisomic mosaicism in prenatal diagnosis: estimated performance of a 50K SNP microarray", Prenat Diagn 2007; 27; 2007, 1197-1204.
D'Aquila, Richard et al., "Maximizing sensitivity and specificity of PCR by pre-amplification heating", Nucleic Acids Research, 19(13), 1991, p. 3749.
Daruwala, Raoul-Sam et al., "A Versatile Statistical Analysis Algorithm to Detect Genome Copy Number Variation", PNAS, 101(46), 2004, 16292-16297.
De Vries, et al., "Diagnostic genome profiling in mental retardation", Am J Hum Genet, 77, published online Aug. 30, 2005, 2005, 606-616.
Deangelis, M. et al., "Solid-phase Reversible Immobilization for the Isolation of PCR Products", Nucleic Acids Research; 23 (22), 1995, 4742-4743.
Devaney, S. et al., "Noninvasive Fetal Sex Determination Using Cell-Free Fetal DNA: A Systematic Review and Meta-analysis", JAMA, 306 (6), 2011, 627-636.
Dhallan, et al., "Methods to Increase the Percentage of Free Fetal DNA Recovered from the Maternal Circuaton", JAMA, 291(9), 2004, 1114-1119.
Dhalian, Ravinder et al., "A non-invasve test for prenatal diagnosis based on fetal DNA present in maternal blood: a preliminary study", The LANCET, 369, 2007, 474-481.
Dieffenbach, C W. et al., "General Concepts for PCR primer design", Genome Research. PCR methods and Applications vol. 3, 1993, S30-S37.
Ding, C et al., "Direct molecular haplotyping of long-range genomic DNA with M1-PCR", PNAS 100(13), 2003, 7449-7453.
Dohm, J. et al., "Substantial Biases in Ultra-Short Read Data Sets From High-Throughput DNA Sequencing", Nucleric Acids Research, 36 (16), e105, 2008, 10 pgs.
Dolganov, Gregory et al., "A Novel Method of Gene Transcript Profiling in Airway Biopsy Homogenates Reveals Increased Expression of a Na—K+—Cl-Cotransporter (NKCC1) in Asthmatic Subjects", Genome Res., 11, 2001, 1473-1483.
Donohoe, Gerard G et al., "Rapid Single-Tube Screening of the C282Y Hemochromatosis Mutation by Real-Time Multigiex Allele-specific PCR without Fluorescent Probes", Clinicai Chemistry, 46, 10, 2000, 1540-1547.
Donoso, P. et al., "Current Value of Preimplantation Genetic Aneuploidy Screening in IVF", Human Reproduction Update, 13(1), 2007, 15-25.
Echeverri, et al., "Caffeine's Vascular Mechanisms of Action", International Journal of Vascular Medicine vol. 2010(2010), 10 pages, Aug. 25, 2010.
Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.

(56) References Cited

OTHER PUBLICATIONS

Eichler, H., "Mild Course of Fetal Rh D Haemolytic Disease due to Maternal Alloimmunisation to Paternal HLA Class I and II Antigens"; Vox Sang, 68, 1995, 243-247.
Ellison, Aaron M., "Bayesian Inference in Ecology", Ecology Letters, 2004, vol. 7, p. 509-520.
Ellonen, P. et al., "Development of SNP Microarray for Supplementary Paternity Testing", International Congress Series, 1261, 2004, 12-14.
EP06838311.6, "European Communication and Extended European Search Report", dated Dec. 30, 2008; 8 pgs.
EP08742125.1, "European Communication Pursuant to Article 94(3) EPC and Examination Report", dated Feb. 12, 2010, 5 pgs.
Fan, et al., "Whole-genome molecular haplotyping of single cells", Nature Biotechnology, vol. 29; No. 1, Jan. 1, 2011, 51-57.
Fan, Christina H. et al., "Non-Invasive Prenatal Measurement of the Fetal Genome", Nature, doi:10.1038/nature11251, 2012, 26 pgs.
Fan, Christina H et al., "Noninvasive Diagnosis of Fetal Aneuoloidy by Shotgun Sequencing DNA from Maternal Blood", PNAS, 105, 42, 2008, 16266-16271.
Fan, Jian-Bing et al., "Highly Parallel Genomic Assay", Nature Reviews, 7, 2006, 632-644.
Fazio, Gennaro et al., "Identification of RAPD Markers Linked to Fusarium Crown and Root Rot Resistance (Frl) in Tomato", Euphytica 105, 1999, 205-210.
Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.
Fiorentino, F et al., "Strategies and Clinical Outcome of 250 Cycles of Preimplantation Genetic Diagnosis for Single Gene Disorders", Human Reproduction, 21, 3, 2006, 670-684.
Fiorentino, Francesco et al., "Short Tandem Repeats Haplotyping of the HLA Region in Preimplantation HLA Matching", European Journal of Human Genetics, 13, 2005, 953-958.
Forejt, et al., "Segmental trisomy of mouse chromosome 17: introducing an alternative model of Down's syndrome", Genomics, 4(6), 2003, 647-652.
Forshew, et al., "Noninvasive identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.
Fredriksson, et al., "Multiplex amplification of all coding sequences within 10 cancer genes by Gene-Collector", Nucleic Acids Research, 2007, vol. 35, No. 7 e47, 1-6.
Freeman, Jennifer L. et al., "Copy Number Variation: New Insights in Genome Diversity", Genome Research, 16, 2006, 949-961.
Frost, Mackenzie S. et al., "Differential Effects of Chronic Pulsatile Versus Chronic Constant Maternal Hyperglycemia on Fetal Pancreatic B-Cells", Journal of Pregnancy, 2012,, Article ID 812094, 2012, 8.
Ganshirt-Ahlert, D. et al., "Ratio of Fetal to Maternal DNA is Less Than 1 in 5000 at different Gestational Ages in Maternal Blood", Clinical Genetics, 38, 1990, 38-43.
Ganshirt-Ahlert, D. et al., "Fetal DNA in Uterine Vein Blood", Obstetrics & Gynecology, 80 (4), 1992, 601-603.
Ganshirt-Ahlert, Dorothee et al., "Three Cases of 45,X/46,XYnf Mosaicism", Human Genetics, 76, 1987, 153-156.
Gardina, P. et al., "Ploidy Status and Copy Number Aberrations in Primary Glioblastomas Defined by Integrated Analysis of Allelic Ratios, Signal Ratios and Loss of Heterozygosity Using 500k SNP Mapping Arrays", BMC Genomics, 9 (489), (doi:10.1186/1471-2164-9-489), 2008, 16 pgs.
Ghanta, Sujana. et al., "Non-Invasive Prenatal Detection of Trisomy 21 Using Tandem Single Nucleotide Polymorphisms", PLoS ONE, 5 (10), 2010, 10 pgs.
Gjertson, David W et al., "Assessing Probability of Paternity and the Product Rule in DNA Systems", Genetica, 96, 1995, 89-98.

Greenwalt, T. et al., "The Quantification of Fetomaternal Hemorrhage by an Enzyme-Linked Antibody Test with Glutaraldehyde Fixation", Vox Sang, 63, 1992, 268-271.
Gueerra, J., "Terminal Contributions for Duplex Oligonucleotide Thermodynamic Properties in the Context of Nearest Neighbor Models", Biopolymers, 95(3), (2010), 2011, 194-201.
Gueetta, Esther et al., "Analysis of Fetal Blood Cells in the Maternal Circulation: Challenges, Ongoing Efforts, and Potential Solutions", Stem Cells and Development, 13, 2004, 93-99.
Guichoux, et al., "Current Trends in Microsatellite Genotyping", Molecular Ecology Resources, 11, 2011, 591-911.
Hall, M., "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Dec. 8, 2014].
Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.
Hara, Eiji et al., "Subtractive eDNA cloning using oligo(dT)3o-latex and PCR: isolation of eDNA clones specific to undifferentiated human embryonal carcinoma cells", Nucleic Acids Research, 19(25), 1991, 7097-7104.
Hardenbol, P., "Multiplexed Genotyping With Secquence-Tagged Molecular Inversion Probes", Nature Biotechnology, 21 (6), 2003, 673-678.
Hardenbol, Paul et al., "Highly multiplexed molecular inversion probe genotyping: Over 10,000 targeted SNPs genotyped in a singled tube essay", Genome Research, 15, 2005, 269-275.
Harismendy, O. et al., "Method for improving Sequence Coverage Uniformity of Targeted Genomic Intervals Amplified by LR-PCR Using Illumina GA Sequencing-By-Synthesis Technology"; Bio Techniques, 46(3), 2009, 229-231.
Harper, J. C. et al., "Recent Advances and Future Developments in PGD", Prenatal Diagnosis, 19, 1999, 1193-1199.
Harton, G.L. et al., "Preimplantation Genetic Testing for Marfan Syndrome", Molecular Human Reproduction, 2 (9), 1996, 713-715.
Hayden, et al., "Multiplex-Ready PCP: A new method for multiplexed SSR and SNP genotyping", BMC Genomics 2008 9(80), 1-12.
Hellani, A. et al., "Clinical Application of Multiple Displacement Amplification in Preimplantation Genetic Diagnosis", Reproductive BioMedicine Online, 10 (3), 2005, 376-380.
Hellani, Ali et al., "Multiple displacement amplification on single cell and possible PGD applications", Molecular Human Reproduction, 10(11), 2004, 847-852.
Hojsgaard, S. et al., "BIFROST—Block recursive models induced from relevant knowledge, observations, and statistical techniques", Computational Statistics & Data Analysis, 19(2), 1995, 155-175.
Holleley, et al., "Multiplex Manager 1.0: a Cross-Platform Computer Program that Plans and Optimizes Multiplex PCR", BioTechniques46:511-517 (Jun. 2009), 511-517.
Hollox, E. et al., "Extensive Normal Copy Number Variation of a β-Defensin Antimicrobial-Gene Cluster", Am. J. Hum. Genet., 73, 2003, 591-600.
Homer, et al., "Resolving Individuals Contributing Trace Amounts of DNA to Highly Complex Mixtures Using High-Density SNP Genotyping Microarrays", PLOS Genetics, 4(8), 2008, 9 pgs.
Hoogendoorn, Bastiaan et al., "Genotyping Single Nucleotide Polymorphisms by Primer Extension and High Performance Liquid Chromatography", Hum Genet, 104, 1999, 89-93.
Hospital, F. et al. "A General Algorithm to Compute Multilocus Genotype Frequencies Under Various Mating Systems" vol. 12, No. 6, Jan. 1, 1996 (Jan. 1, 1996), pp. 455-462.
Howie, et al., "Fast and accurate genotype imputation in genome-wide association studies through pre-phasing", Nature Genetics, vol. 44, No. 8, Jul. 22, 2012, 955-959.
Hu, Dong Gui et al., "Aneuploidy Detection in Single Cells Using DNA Array-Based Comparative Genomic Hybridization"; Molecular Human Reproduction , 10(4), 2004, 283-289.

(56) References Cited

OTHER PUBLICATIONS

Ido, Yasuo et al., "Hyperglycemia-Induced Apoptosis in Human Umbilical Vein Endothelial Cells: Inhibition by the AMP-Activated Protein Kinase Activation", Diabetes, 51. 2002, 159-167.
Illumina Catalog, "Paired-End Sample Preparation Guide, Illumina Catalog# PE-930-1 001, Part# 1005063 Rev. E", 2011, 1-40.
Ishii, et al., "Optimizaton of Annealing Temperature to Reduce Bias Caused by a Primer Mismatch in Multitemplate PCR", Applied and Environmental Microbiology, Aug. 2001, p. 3753-3755.
Johnson, D.S. et al., "Comprehensve Analysis of Karyotypic Mosaicism Between Trophectoderm and Inner Cell Mass", Molecular Human Reproduction, 16(12), 2010, 944-949.
Johnson D.S. et al., "Preclinical Validation of a Microarray Method for Full Molecular Karyotyping of Blastomeres in a 24-h Protocol", Human Reproduction, 25 (4), 2010, 1066-1075.
Kaplinski, Lauris et al., "MultiPLX: Automatic Grouping and Evaluation of PCR Primers", Bioinformatics, 21(8), 2005, 1701-1702.
Kazakov, V.I et al., "Extracellular DNA in the Blood of Pregnant Women", sitologia, 37, 3, 1995, 8.
Kijak, G. et al., "Discrepant Results in the Interpretation of HIV-1 Drug-Resistance Genotypic Data Among Widely Used Algorithms", HIV Medicine, 4, 2003, 72-78.
Kinnings, S. L. et al., "Factors affecting levels of circulating cell-free fetal DNA in maternal plasma and their implications for noninvasive prenatal testing", Prenatal Diagnosis, vol. 35, 2015, 816-822.
Konfortov Bernard A. et al., "An Efficient Method for Multi-Locus Molecular Haplotyping", Nucleic Acids Research, 35(1), e6, 2007, 8 pgs.
Krjutskov, K. et al.,"Development of a single tube 640-plex genotyping method for detection of nucleic acid variations on micoarrays", Nucleic Acids Research, vol. 36, No. 12, May 23, 2008 (May 23, 2008), pp. e75-e75.
Kuliev, Anver et al., "Thirteen Years' Experience on Preimplantation Diagnosis: Report of the Fifth International Symposium on Preimplantation Genetics", Reproductive Biomedicine Online, 8, 2, 2004, 229-235.
Lambert-Messerlian, G. et al., "Adjustment of Serum Markers in First Trimester Screening", Journal of Medical Screening, 16 (2), 2009, 102-103.
Lathi, Ruth B. et al., "Informatics Enhanced SNP Microarray Analysis of 30 Miscarriage Samples Compared to Routine Cytogenetics", PLoS ONE, 7(3), 2012, 5 pgs.
Leary, Rebecca J. et al., "Detection of Chromosomal Alterations in the Circulation of Cancer Patients with Whole-Genome Sequencing", Science Translational Medicine, 4, 162, 2012, 12.
Li, Ying. et al., "Non-Invasive Prenatal Diagnosis Using Cell-Free Fetal DNA in Maternal Plasma from PGD Pregnancies", Reproductive BioMedicine Online, 19 (5), 2009, 714-720.
Li, Ying et al., "Size Separation of Circulatory DNA in Maternal Plasma Permits Ready Detection of Fetal DNA Polymorphims", Clinical Chemistry, 50, 6, 2004, 1002-1011.
Li B, "Highly Multiplexed Amplicon Preparation for Targeted Re-Sequencing of Sample Limited Specimens Using the Ion AmpliSeq Technology nd Semiconductor Sequencing", Proceedings of the Annual Meeting of the American Society of Human Genetics [retrieved on Oct. 30, 2012]. Retrieved from the Internet: <URL:http://www.ashg.org/2012meeting/abstracts/fulltext/f120121811.htm>, 2012, 1 pg.
Liao, Gary J.W. et al., "Targeted Massively Parallel Sequencing of Maternal Plasma DNA Permits Efficient and Unbiased Detection fo Fetal Alleles", Clinical Chemistry, 57 (1), 2011, 92-101.
Liao, J. et al., "An Alternative Linker-Mediated Polymerase Chain Reaction Method Using a Dideoxynucleotide to Reduce Amplification Background", Analytical Biochemistry 253, 137-139 (1997).
Liew, Michael et al., "Genotyping of Single-Nucleotide Polymorphisms", Clinical Chemistry, 50(7), 2004, 1156-1164.
Lindroos, Katarina et al., "Genotyping SNPs by minisequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.
Lo, et al., "Digital PCR for the Molecular Detection of Fetal Chromosomal Aneuploidy", PNAS, vol. 104, No. 32, Jul. 7, 2007, 13116-13121.
Lo, et al., "Fetal Nucleic Acids in Maternal Blood: the Promises", Clin. Chem. Lab. Med., 50(6), 2012, 995-998.
Lo, et al., "Free Fetal DNA in Maternal Circulation", JAMA, 292(23), (Letters to the Editor), 2004, 2835-2836.
Lo, , "Non-Invasive Prenatal Diagnosis by Massively parallel Sequencing of Maternal Plasma DNA", Open Biol 2: 120086, 2012, 1-5.
Lo, et al., "Prenatal Sex Determination by DNA Amplification from Maternal Peripheral Blood", The Lancet,2, 8676, 1989, 363-1365.
Lo, et al., "Rapid Clearance of Fetal DNA from Maternal Plasma", Am. J. Hum. Genet., 64, 1999; 218-224.
Lo, et al., "Strategies for the Detection of Autosomal Fetal DNA Sequence from Maternal Peripheral Blood", Annals New York Academy of Sciences,731, 1994, 204-213.
Lo, et al., "Two-way cell traffic between mother and fetus: biologic and clinical implications", Blood, 88(11), Dec. 1, 1996, 4399-4395.
Lo, Dennis Y. et al., "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.
Lo, Dennis Y. et al., "Plasma placental RNA allelic ratio permits noninvasive prenatal chromosomal aneuploidy detection", Nature Medicine, 13(2), 2007, 218-223.
Lo, Dennis Y.M. et al., "Maternal Plasma DNA Sequencing Reveals the Genome-Wide Genetic and Mutational Profile of the Fetus", Science Translational Medicine, 2, 61, 2010, 13.
Lo, Dennis Y.M. et al., "Presence of Fetal DNA in Maternal Plasma and Serum", The Lancet, 350, 1997, 485-487.
Lo, Dennis Y.M. et al., "Quantitative Analysis of Fetal DNA in Maternal Plasma and Serum: Implications for Noninvasive Prenatal Diagnosis", Am. Hum. Genet., 62, 1998, 768-775.
Lo, Y.M.D et al., "Prenatal Determination of Fetal Rhesus D Status by DNA Amplification of Peripheral Blood of Rhesus-Negative Mothers", Annals New York Academy of Sciences, 731, 1994, 229-236.
Lo, Y-M. D. et al., "Prenatal Determination of Fetal RhD Status by Analysis of Peripheral Blood of Rhesus Negative Mothers", The Lancet, 341, 1993, 1147-1148.
Lo, Y-M.D et al., "Detection of Single-Copy Fetal DNA Sequence from Maternal Bood", The Lancet, 335, 1990, 1463-1464.
Lo, Y. et al., "Detection of Fetal RhD Sequence from Peripheral Blood of Sensitized RhD-Negative Pregnant Women", British Journal of Haematology, 87, 1994, 658-660.
Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.
Maniatis, T. et al., "In: Molecular Cloning: A Laboratory Manual", Cold Spring Harbor Laboratory, New York, Thirteenth Printing, 1986, 458-459.
Mansfield, Elaine S , "Diagnosis of Down Syndrome and Other Aneuploidies Using Quantitative Polymerase Chain Reaction and Small Tandem Repeat Polymorphisms", Human Moiecular Genetics, 2, 1, 1993, 43-50.
Markoulatos, P. et al., "Multiplex Polymerase Chain Reaction: A Practical Approach", 2002 Wiley-Liss, Inc. DOI 10.1002/jcla.2058 Journal of Clinical Laboratory Analysis 16:47-51 (2002).
May, Rober M. et al., "How Many Species Are There on Earth?", Science, 241, 1988, 1441-1449.
McCray, Alexa T. et al., "Aggregating UMLS Semantic Types for Reducing Conceptual Complexity", MEDINFO 2001: Proceedings of the 10th World Congress on Medical Informatics (Studies in Health Technology and Informatics, 84, V. Patel et al. (eds.), IOS Press Amsterdam, 2001, 216-220.
Mennuti, M. et al., "Is It Time to Sound an Alarm About False-Positive Cell-Free DNA Testing for Fetal Aneuploidy?", American Journal of Obstetric, 2013, 5 pgs.

(56) References Cited

OTHER PUBLICATIONS

Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19(4), 2013, 318-329.
Miller, Robert , "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.
Miller, Robert R , "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.
Morand, et al., "Hesperidin contributes to the vascular protective effects of orange juice: a randomized crossover study in healthy volunteers", Am J Clin Nutr. Jan. 2011;93(1 ):73-80. Epud Nov. 10, 2010.
Munne, S. et al., "Chromosome abnormalities in human embryos", Human Reproduction Update, 4 (6), 842-855.
Murtaza, M. et al., "Non-Invasive Analysis of Acquired Resistance to Cancer Therapy by Sequencing of Plasma DNA", Nature (doi:10. 1038/nature12065), 2012, 6 pgs.
Muse, Spencer V., "Examining rates and patterns of nucleotide substitution in plants", Plant Molecular Biology 42: 25-43, 2000.
Myers, Chad L. et al., "Accurate Detection of Aneuploidies in Array CGH and Gene Expression Microarray Data", Bioinformatics, 20(18), 2004, 3533-3543.
Nannya, Yasuhito et al., "A Robust Algorithm for Copy Number Detection Using High-density Oligonucleotide Single Nucleotide Polymorphism Genotyping Arrays", Cancer Res., 65, 14, 2005: 6071-6079.
Nicolaides, K. et al., "Noninvasive Prenatal Testing for Fetal Trisomies in a Routinely Screened First-Trimester Population", American Journal of Obstetrics (article in press), 207, 2012, 1.e1-1.e6.
Nicolaides, K.H. et al., "Validaton of Targeted Sequencing of Single-Nucleotide Polymorphisms for Non-Invasive Prenatal Detection of Aneuploidy of Chromosomes 13, 18, 21, X, and Y", Prenatal Diagnosis, 33, 2013, 575-579.
Nicolaides, Kypros H. et al., "Prenatal Detection of Fetal Triploidy from Cell-Free DNA Testing in Meternal Blood", Fetal Diagnosis and Therapy, 2013, 1-6.
Nygren, et al., "Quantification of Fetal DNA by Use of Methylation-Based DNA Discrimination", Clincal Chemistry 56:10 1627-1635 (2010).
Ogino, S. et al., "Bayesian Analysis and Risk Assessment in Genetic Counseling and Testing", Journal of Molecular Diagnostics, 6 (1), 2004, 9 pgs.
O'Malley, R. et al., "An adapter ligation-mediated PCR method for high-throughput mapping of T-DNA inserts in the Arabidopsis genome", Nat. Protoc. 2, 2910-2917 (2007).
Orozco A.F., et al., "Placental Release of Distinct DNA-Associated Micro-Particles into Maternal Circulation: Reflective of Gestation Time and Preeclampsia", Placenta,30, 2009, 891-897.
Ozawa, Makiko et al., "Two Families with Fukuyama Congenital Muscular Dystrophy that Underwent in Utero Diagnosis Based on Polymorphism Analysis", Clinical Muscular Dystrophy: Research in Immunology and Genetic Counseling—FY 1994 Research Report, 1994, 8.
Paez, Guillermo J. et al., "Genome coverage and sequence fidelity of φ29 polymerase-based multiple strand displacement whole genome amplification", Nucleic Acids Research, 32(9), 2004, 1-11.
Page, S. L. et al., "Chromosome Choreography: The Meiotic Ballet", Science, 301, 2003, 785-789.
Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012, 10.
Palomaki, Glenn E. et al., "DNA Sequencing of Maternal Plasma to Detect Down Syndrome: An International Clinical Validation Study", Genetics in Medicine (pre-print verson), 13, 2011, 8 pgs.
Papageorgiou, Elisavet A. et al., "Fetal-Specific DNA Methylation Ratio Permits Noninvasive Prenatal Diagnosis of Trisomy 21", Nature Medicine (advance online publicaton),17, 2011, 5 pgs.
PCT/US2006/045281, "International Preliminary Report on Patentability", dated May 27, 2008, 1 pg.
PCT/US2006/045281, "International Search Report and Written Opinion", dated Sep. 28, 2007, 7 pgs.
PCT/US2008/003547, "International Search Report", dated Apr. 15, 2009, 5 pgs.
PCT/US2009/034506, "International Search Report", dated Jul. 8, 2009, 2 pgs.
PCT/US2009/045335, "International Search Report", dated Jul. 27, 2009, 1 pg.
PCT/US2009/052730, "International Search Report"; dated Sep. 28, 2009; 1 pg.
PCT/US2010/050824, "International Search Report"; dated Nov. 15, 2010, 2 pgs.
PCT/US2011/037018, "International Search Report"; dated Sep. 27, 2011, 2 pgs.
PCT/US2011/061506, "International Search Report", dated Mar. 16, 2012, 1 pgs.
PCT/US2011/066938, "International Search Report", dated Jun. 20, 2012, 1 pg.
PCT/US2012066339, "International Search Report", dated Mar. 5, 2013, 1 pg.
PCT/US2013/028378, "International Search Report and Written Opinion", dated May 28, 2013, 11 pgs.
PCT/US2013/57924, "International Search Report and Written Opinion", dated Feb. 18, 2014, 8 pgs.
PCT/US2014/051926, "International Search Report mailed", dated Dec. 9, 2014, 3 pgs.
PCT/US2014/51926, "Written Opinion", dated Dec. 9, 2014, 5 pgs.
PCT/US2015/026957, "International Preliminary Report on Patentability dated Nov. 3, 2016", dated Nov. 3, 2016, 3 pages.
Pearson, K., "On the criterion that a given system of deviations from the probable in the case of a correlated system of variables is such that it can be reasonably supposed to have arisen from random sampling", Philosophical Magazine Series 5, vol. 50, Issue 302, 1900, 157-175.
Pena, Sergio D.J et al., "Paternity Testing in the DNA Era", Trends in Genetics, 10, 6, 1994, 204-209.
Perkel, Jeffrey M. , "Overcoming the Challenges of Multiplex PCR", Biocompare Editorial Article, NULL, 2012, 1-5.
Perry, George H. et al., "The Fine-Scale and Complex Architecture of Human Copy-Number Variation", The American Journal of Human Genetics,82, 2008, 685-695.
Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.
Peters, David P. et al., "Noninvasive Prenatal Diagnosis of a Fetal Microdeletion Syndrome", New England Journal of Medicine, 365(19), 2011, 1847-1848.
Pfaffl, Michael W., "Relative Expression Software Tool (REST©) for Group-Wise Comparison and Statistical Analysis of Relative Expression Results in real-Time PCR", Nucleic Acids Research, 30(9), 2002, 10 pgs.
Phillips, C. et al., "Resolving Relationship Tests that Show Ambiguous STR Results Using Autosomal SNPs as Supplementary Markers"; Forensic Science International: Genetics 2, 2008, 198-204.
Podder, Mohua et al., "Robust SN P genotyping by multiplex PCR and arrayed primer", BMC Medical Genomics,1(5), 2008, 1-15.
Porreca, Gregory J et al., "Multiplex Amplification of Large Sets of Human Exons", Nature Methods, 4, (advance online publication), 2007, 6.
Price, T.S. et al., ""SW-Array: a dynamic programming solution for the identification of copy-number changes in genomic DNA using array comparative genome hybridization data",", Nucleic Acids Research, vol. 33, No. 11, Jun. 16, 2005 (Jun. 16, 2005), pp. 3455-3464.

(56) References Cited

OTHER PUBLICATIONS

Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.
Rabinowitz, Matthew et al., "Origins and rates of aneuploidy inhuman blastomeres", Fertility and Sterlity, Elsevier Sciencie Inc, 97(2), 2012, 395-401.
Rabinowitz, Matthew. et al., "Non-Invasive Prenatal Aneuploidy Testing of Chromosomes 13, 18, 21, X, and Y Using Targeted Sequencing of *Polymorphic Loci*", The American Society of Human Genetics, meeting poster, 2012, 1 pg.
Rachlin, J. et al., "Computational tradeoffs in multiplex PCR assay design for SNP genotyping", BMC Genomics, vol. 6, No. 102, Jul. 25, 2005, 11 pages.
Rahmann, Sven et al., "Mean and variance of the Gibbs free energy of oligonucleotides in the nearest neighbor model under varying conditions", Bioinformatics, 20(17), 2004, 2928-2933.
Rava, Richard P. et al., "Circulating Fetal Cell-Free DNA Fraction Differ in Autosomal Aneuploidies and Monosomy X", Clinical Chemistry, 60(1), (papers in press), 2012, 8 pgs.
Rechitsky, Svetlana et al., "Preimplantation Genetic Diagnosis with HLA Matching", Reproductive Bio Medicine Online, 9, 2, 2004, 210-221.
Renwick, Pamela. et al., "Proof of Principle and First Cases Using Preimplantation Genetic Haplotyping—A Paradigm Shift for Embryo Diagnosis", Reproductive BioMedicine Online, 13 (1), 2006, 110-119.
Ricciotti, Hope, "Eating by Trimester", Online], Retrieved from Internet:<http://www.youandyourfamily.com/article.php?story=Eating+by+Trimester>, 2014, 3.
Roper, Stephen M. et al. "Forensic Aspects of DNA-Based Human Identity Testing", Journal of Forensic Nursing, 4, 2008, 150-156.
Roux, K., "Optimization and Troubleshooting in PCR", PCR Methods Appl. 4, 1995, 185-194.
Rozen, Steve et al., "Primer3 on the WWW for General Users and for Biologis Programmers", Methods in Molecular Biology, 132: Bioinformatics Methods and Protocols, 1999, 365-386.
Russel, L M., "X Chromosome Loss and Ageing", Cytogenetic and Genome Res., 116, 2007, 181-185.
Ryan, et al., "The importance of phase information for human genomics", Nature Reviews Genetics, voi. 12, No. 3, Mar. 1, 2011.
Ryan, Allison et al., "Informatics-Based, Highly Accurate, Noninvasive Prenatal Paternity Testing", Genetics in Medicine (advance online publication), 2012, 5 pgs.
Rychlik, et al., "Optimization of the annealing temperature for DNA amplification in vitro", Nucleic Acids Research, 18(21), 1990, 6409-6412.
Samango-Sprouse, C. et al., "SNP-Based Non-Invasive Prenatal Testing Detects Sex Chromosome Aneuploidies with High Accuracy", Prenatal Diagnosis, 33, 2013, 1-7.
Sander, Chris, "Genetic Medicine and the Future of Health Care", Science, 287(5460), 2000, 1977-1978.
Santalucia, J. et al., "The Thermodynamics of DNA Structural Motifs", Annu. Rev. Biophys. Biomol. Struct., 33, 2004, 415-440.
Santalucia, John J.R et al., "Improved Nearest-Neighbor Parameters for Predicting DNA Duplex Stability", Biochemistry, 35, 1996, 3555-3562.
Sasabe, Yutaka, "Genetic Diagnosis of Gametes and Embryos Resulting from ART", Japanese Journal of Fertility and Sterility, 2001, vol. 46, No. 1, p. 43-46.
Schoumans, J. et al., "Detection of chromosomal imbalances in children with idiopathic mental retardation by array based comparative genomic hybridisation (array-CGH)", JMed Genet, 42, 2005, 699-705.
Sebat, Jonathan et al., "Strong Association of De Novo Copy Number Mutations with Autism", Science, 316, 2007; 445-449.
Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.
Sermon, Karen et al., "Preimplantation genetic diagnosis", The Lancet, Lancet Limited. 363(9421), 2000, 1633-1641.
Servin, B et al., "MOM: A Program to Compute Fully Informative Genotype Frequencies in Complex Breeding Schemes", Journal of Heredity, vol. 93, No. 3, Jan. 1, 2002 (Jan. 1, 2001), pp. 227-228.
Shaw-Smith, et al., "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., 41, 2004, 241-248.
Shen, et al., "High-quality DNA sequence capture or 524 disease candidate genes", High-quality DNA sequence canture of 524 disease candidate genes, Proceedings of the National Academy of Sciences, vol. 108, No. 16, Apr. 5, 2011 (Apr. 5, 2011), pp. 6540-6554.
Shen, Zhiyong, "MPprimer: a program for reliable multiplex PCR primer design", BMC Bioinformatics 2010, 11:143, 1-7.
Sherlock, J et al., "Assessment of Diagnostic Quantitative Fluorescent Multiplex Polymerase Chain Reaction Assays Performed on Single Cells", Annals of Human Genetics,62, 1, 1998, 9-23.
Simpson, J. et al., "Fetal Cells in Maternal Blood: Overview and Historical Perspective", Annals New York Academy of Sciences, 731, 1994, 1-8.
Sint, Daniela et al., "Advances in Multiplex PCR: Balaning Primer Efficiencies and Improving Detection Success", Methods in Ecology and Evolution, 3, 2012, 898-905.
Slater, Howard et al., "High-Resolution Identification of Chromosomal Abnormalities Using Oligonucleotide Arrays Containing 116,204 SNPs", Am. J. Hum. Genet., 77, 5, 2005, 709-726.
Snijders, Antoine et al., "Assembly of Microarrays for Genome-Wide Measurement of DNA Copy Number", Nature Genetic, 29, 2001, 263-264.
Sparks, et al., "Non-Invasive Prenatal Detection and Selective Analysis of Cell-Fee DNA Obtained from Maternal Blood: Evaluation for Trisomy 21 and Trisomy 18", American Journal of Obstetrics & Gynecology 206, 2012, 319.e1-319.e9.
Sparks, Andrew B. et al., "Selective Analysis of Cell-Free DNA in Maternal Blood for Evaluation of Fetal Trisomy", Prenatal Diagnosis, 32, 2012, 1-7.
Spiro, Alexander et al., "A Bead-Based Method for Multiplexed Identification and Quantitated of DNASequences using Flow Cytometry", Applied and Environmental Microbiology, 66, 10, 2000, 4258-4265.
Spits, C et al., "Optimization and Evaluation of Single-Cell Whole Genome Multiple Displacement Amplification", Human Mutation, 27(5), 496-503, 2006.
Srinivasan, et al., "Noninvasive Detection of Fetal Subchromosome Abnormalities via Deep Sequencing of Maternal Plasma", The American journal of Human Genetics 92, 167-176, Feb. 7, 2013.
Stephens, Mathews. et al., "A Comparison of Bayesian Methods for Haplotype Reconstruction from Population Genotype Data", Am. J. Hum. Genet., 73, 2003, 1162-1169.
Stevens, Robert et al., "Ontology-Based Knowledge Representation for Bioinformatics", Briefings in Bioinformatics, 1, 4, 2000, 398-414.
Steyerberg, E.W et al., "Application of Shrinkage techniques in Logistic Regression Anaysis: A Case Stud", Statistica Neerlandica, 55(1), 2001, 76-88.
Strom, C. et al., "Three Births after preimplantation genetic diagnosis for cystic fibrosis with sequential first and second polar body analysis", American Journal of Obstetrics and Gynecology, 178 (6), 1998, 1298-1306.
Strom, Charles M. et al., "Neonatal Outcome of Preimplantation Genetic Diagnosis by Polar Body Removal: The First 109 Infants", Pediatrics, 106( 4), 2000, 650-653.
Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.

(56) References Cited

OTHER PUBLICATIONS

Su, S.Y. et al., ""Inferring combined CNV/SNP haplotypes from genotype data"", Bioinformatics, vol. 26, No. 11,1, Jun. 1, 2010; 1437-1445.

Sun, Guihua et al., "SNPs in human miRNA genes affect biogenesis and function", RNA, 15(9), 2009, 1640-1651.

Sweet-Kind Singer, J. A. et al., "Log-penalized linear regresson", IEEE International Symposium on Information Theory, 2003. Proceedings, 2003, 286.

Tamura, et al., "Sibling Incest and formulation of paternity probability: case report", Legal Medicine, 2000, vol. 2, p. 189-196.

Tang, et al., Multiplex fluorescent PCR for noninvasive prenatal detection of fetal-derived paternally inherited diseases using circulatory fetal DNA in maternal plasma, Eur J Obstet Gynecol Reprod Biol, 2009, vol. 144, No. 1, p. 35-39.

Tang, N. et al., "Detectlon of Fetal-Derived Paternally Inherited X-Chromosome Polymorphisms in Maternal Plasma", Clinical Chemistry, 45 (11), 1999, 2033-2035.

Thomas, M.R et al., "The Time of Appearance and Disappearance of Fetal DNA from the Maternal Circulation", Prenatal Diagnosis, 15, 1995, 641-646.

Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.

Tong, Yu K. et al., "Noninvasive Prenatal Detection of Trisomy 21 by Epigenetic-Genetic Chromosome-Dosage Approach", Clinical Chemistry, 56(1), 2010, 90-98.

Troyanskaya, Olga G. et al., "A Bayesian Framework for Combining Heterogeneous Data Sources for Gene Function Prediction (in *Saccharomyces cerevisiae*)", PNAS, 100(14), 2003, 8348-8353.

Tsui, Nancy B.Y et al., "Non-Invasive Prenatal Detection of Fetal Trisomy 18 by RNA-SNP Allelic Ratio Analysis Using Maternal Plasma SERPINB2 mRNA, A Feasibility Study", Prenatal Diagnosis, 29, 2009, 1031-1037.

Turner, E. et al., "Massively Parallel Exon Capture and Library-Free Resequencing Across 16 Genomes", Nature Methods, 6 (5), 2009, 315-316.

Vallone, Peter, "AutoDimer: a Screening Tool for Primer-Dimer and Hairpin Structures", Bio Techniques, 37, 2004, 226-231.

Varley, Katherine Elena et al., "Nested Patch PCR Enables Highly Multiplexed Mutation Discovery in Candidate Genes", Genome Res., 18(11), 2008, 1844-1850.

Verlinsky, Y. et al., "Over a Decade of Experience with Preimplantation Genetic Diagnosis", Fertility and Sterility, 82 (2), 2004, 302-303.

Wagner, Jasenka et al., "Non-Invasive Prenatal Paternity Testing from Maternal Bood", Int. J. Legal Med., 123, 2009, 75-79.

Wang, Eric et al., "Gestational Age and Maternal Weight Effects on Fetal Cell-Free DNA in Maternal Plasma", Prenatal Diagnosis, 33, 2013, 662-666.

Wang, Hui-Yun et al., "A genotyping system capable of simultaneously analyzing >1000 single nucleotide polymorphisms in a haploid genome", Genome Res., 15, 2005, 276-283.

Wang, Yuker et al., "Allele quantification using molecular inversion probes (MIP)", Nucleic Acids Research, vol. 33, No. 21, Nov. 28, 2005, 14 pgs.

Wapner, R. et al., "Chromosomal Microarray Versus Karyotyping for Prenatal Diagnosis", The New England Journal of Medicine, 367 (23), 2012, 2175-2184.

Watkins, N. et al., "Thermodynamic contributions of single internal rA •dA, rC • dC, rG • dG and rU • dT mismatches in RNA/DNA duplexes", Nucleic Acids Research, 9 (5),, 2010, 1894-1902.

Wells, D, "Microarray for Analysis and Diagnosis of human Embryos", 12th International Congress on Prenatal Diagnosis and Therapy, Budapest, Hungary, 2004, 9-17.

Wells, Dagan, "Advances in Preimplantation Genetic Diagnosis", European Journal of Obstertrics and Gynecology and Reproductive Biology, 115S, 2004, S97-S101.

Wells, Dagan, "Detailed Chromosomal and Molecular Genetic Analysis of Single Cells by Whole Genome Amplification and Comprartive Genomic Hybridisation", Nucleic Acids Research, 27, 4, 1999, 1214-1218.

Wen, Daxing et al., "Universal Multiples PCR: A Novel Method of Simultaneous Amplification of Multiple DNA Fragments", Plant Methods, 8(32), NULL, 2012, 1-9.

Wilton, et al., "Birth of a Healthy Infant After Preimplantation Confirmation of Euploidy by Comparative Genomic Hybridization", N. Engl. J. Med., 345(21), 2001, 1537-1541.

Wilton, L., "Preimplantation Genetic Diagnosis and Chromosome Analysis of Blastomeres Using Comparative Genomic Hybridization", Human Reproduction Update, 11 (1), 2005, 33-41.

Wright, C. F. et al., "Cell-free fetal DNA and RNA in maternal blood: implications for safer antenatal testing", BMJ, vol. 39, Jul. 18, 2009, 161-165.

Wu, Y. Y. et al., "Rapid and/or high-throughput genotyping for human red blood cell, platelet and leukocyte antigens, and forensic applications", Clinica Chimica Acta, vol. 363, 2006, 165-176.

Xia, Tianbing et al., "Thermodynamic Parameters for an Expanded Nearest-Neighbor Model for Formation of RNA Duplexes with Watson-Crick Base Pairs", Biochemstry, 37, 1998, 14719-14735.

Yeh, Iwei et al., "Knowledge Acquisition, Consistency Checking and Concurrency Control for Gene Ontology (GO)", Bioinformatics, 19, 2, 2003, 241-248.

You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.

Zhang, Rui et al., "Quantifying RNA allelic ratios by microfluidic multiplex PCR and sequencing", Nature Methods, 11(1), 2014, 51-56.

Zhao, Xiaojun et al., "An Integrated View of Copy Number and Allelic Alterations in the Cancer Genome Using Single Nucleotide Polymorphism Arrays", Cancer Research,64, 2004, 3060-3071.

Zhou, W. et al., "Counting Alleles Reveals a Connection Between Chromosome 18q Loss and Vascular Invasion", Nature Biotechnology, 19, 2001, 78-81.

Zimmermann, et al., "Noninvasive Prenatal Aneuploidy Testing of Chromosomes 13, 18, 21 X, and Y, Using targeted Sequencing of Polymorphic Loci", Prenatal Diagnosis. 32, 2012, 1-9.

Kirkizlar, E. et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 2015, pp. 407-416.

Riley, D. E., "DNA Testing: An Introduction for Non-Scientists an Illustrated Explanation", Scientific Testimony: An Online Journal, http://www.scientific.org/tutorials/articles/riley/riley.html, Apr. 6, 2005, 22 pages.

Tu, J. et al., "Pair-barcode high-throughput sequencing for large-scale multiplexed sample analysis", BMC Genomics, vol. 13, No. 43, Jan. 25, 2012, 1-9.

Abbosh, C. et al., "Phylogenetic ctDNA analysis depicts early-stage lung cancer evolution", NATURE, vol. 545, May 25, 2017, 446-451.

Butler, J. et al., "The Development of Reduced Size STR Amplicons as Tools for Analysis of Degraded DNA*", Journal of Forensic Sciences, vol. 48, No. 5, 2003, 1054-1064.

De Bruin, E. et al., "Spatial and temporal diversity in genomic instability processes defines lung cancer evolution", Science, vol. 346, No. 6206, Oct. 10, 2014, 251-256.

Fan, H. C. et al., "Microfluidic digital PCR enables rapid prenatal diagnosis of fetal aneuploidy", American Journal of Obstetrics & Gynecology, vol. 200, May 2009, 543.e1-543.e7.

Hawkins, T. et al., "Whole genome amplification—applications and advances", Current Opinion in Biotechnology, 13, 2002, 65-67.

Jamal-Hanjani, M. et al., "Detection of ubiquitous and heterogeneous mutations in cell-free DNA from patients with early-stage non-small-cell lung cancer", Annals of Oncology, vol. 27, No. 5, Jan. 28, 2016, 862-867.

Jamal-Hanjani, M. et al., "Tracking Genomic Cancer Evolution for Precision Medicine: The Lung TRACERx Study", PLOS Biology, vol. 12, No. 7, Jul. 2014, 1-7.

(56) References Cited

OTHER PUBLICATIONS

Narayan, A. et al., "Ultrasensitive measurement of hotspot mutations in tumor DNA in blood using error-suppressed multiplexed deep sequencing", Cancer Research, vol. 72, No. 14, Jul. 15, 2012, 3492-3498.

Pathak, A. et al., "Circulating Cell-Free DNA in Plasma/Serum of Lung Cancer Patients as a Potential Screening and Prognostic Tool", Clinical Chemistry, 52, 2006, 1833-1842.

Rogaeva, E. et al., "The Solved and Unsolved Mysteries of the Genetics of Early-Onset Alzheimer's Disease", NeuroMolecular Medicine, vol. 2, 2002, 1-10.

Sahota, A., "Evaluation of Seven PCR-Based Assays for the Analysis of Microchimerism", Clinical Biochemistry, vol. 31, No. 8., 1998, 641-645.

Ten Bosch, J., "Keeping Up Wth the Next Generation Massively Parallel Sequencing in Clinical Diagnostics", Journal of Molecular Diagnostics, vol. 10, No. 6, 2008, 484-492.

Thermofisher Scientific, "Ion AmpliSeq Cancer Hotspot Panel v2", Retrieved from the Internet: https://tools.thermofisher.com/content/sfs/brochures/Ion-AmpliSeq-Cancer-Hotspot-Panel-Flyer.pdf, 2015, 2 pages.

Wikipedia, "Maximum a posteriori estimation", https://en.wikipedia.org/w/index.php?title=Maximum_a_posteriori_estimation&oldid=26878808, [retrieved on Aug. 1, 2017], Oct. 30, 2005, 2 pages.

Wright, C. et al., "The use of cell-free fetal nucleic acids in maternal blood for non-invasive prenatal diagnosis", Human Reproduction Update, vol. 15, No. 1, 2009, 139-151.

Xu, N. et al., "A Mutation in the Fibroblast Growth Factor Receptor 1 Gene Causes Fully Penetrant Normosmic Isolated Hypogonadotropic Hypogonadism", The Journal of Clinical Endocrinology & Metabolism, vol. 92, No. 3, 2007, 1155-1158.

Xu, S. et al., "Circulating tumor DNA identified by targeted sequencing in advanced-stage non-small cell lung cancer patients", Cancer Letters, vol. 370, 2016, 324-331.

Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.

Carvalho, B. et al., "Exploration, normalization, and genotype calls of high-density oligonucleotide SNP array data", Biostatistics, vol. 8, No. 2, 2007, 485-499.

Ford, E. et al., "A method for generating highly multiplexed ChIP-seq libraries", BMC Research Notes, vol. 7, No. 312, May 22, 2014, 1-5.

Wapner, R. et al., "First-Trimester Screening for Trisomies 21 and 18", The New England Journal of Medicine, vol. 349, No. 15, Oct. 9, 2003, 1405-1413.

Ashoor, G. et al., "Fetal fraction in maternal plasma cell-free DNA at 11-13 weeks' gestation: relation to maternal and fetal characteristics", Ultrasound in Obstetrics and Gynecology, vol. 41, 2013, 26-32.

Chan, K.C. et al., "Size Distributions of Maternal and Fetal DNA in Maternal Plasma", Clinical Chemistry, vol. 50, No. 1, 2004, 88-92.

Dodge, Y., "Bayes' Theorem", The Concise Encyclopedia of Statistics, 2008, 30-31.

Geiss, G. K. et al., "Direct multiplexed measurement of gene expression with color-coded probe pairs", Nature Biotechnology, vol. 26, No. 3, Feb. 17, 2008, 317-325.

Gunderson, K. L. et al., "A genome-wide scalable SNP genotyping assay using microarray technology", Nature Genetics, vol. 37, No. 5, May 2005, 549-554.

Quinn, G. P. et al., "Experimental Design and Data Analysis for Biologists", Graphical Exploration of Data, 2002, 64-67.

Anker, P. et al., "Detection of circulating tumour DNA in the blood (plasma/serum) of cancer patients", Cancer and Metastasis Reviews, vol. 18, 1999, 65-73.

Chen, X. Q. et al., "Microsatallite alterations in plasma DNA of small cell lung cancer patients", Nature Medicine, vol. 2, No. 9, Sep. 1996, 1033-1035.

Jenkins, S. et al., "High-throughput SNP genotyping", Comparative and Functional Genomics, vol. 3, Dec. 5, 2001, 57-66.

Kwok, P. Y., "High-throughput genotyping assay approaches", Pharmacogenomics, vol. 1, No. 1, 2000, 1-5.

Lander, E. S. et al., "Initial sequencing and analysis of the human genome", NATURE, vol. 409, Feb. 15, 2001, 860-921.

Levsky, J. M. et al., "Fluorescence in situ hybridization: past, present and future", Journal of Cell Science, vol. 116, No. 14, 2003, 2833-2838.

Tebbutt, S. J. et al., "Microarray genotyping resource to determine population stratification in genetic association studies of complex disease", BioTechniques, vol. 37, Dec. 2004, 977-985.

Yuan, X. et al., "Probability Theory-based SNP Association Study Method for Identifying Susceptibility Loci and Genetic Disease Models in Human Case-Control Data", IEEE Trans Nanobioscience, vol. 9, No. 4, Dec. 2010, 232-241.

Chang, H.W. et al., "Assessment of Plasma DNA Levels, Allelic Imbalance, and CA 125 as Diagnostic Tests for Cancer", Journal of the National Cancer Institute, vol. 94, No. 22, Nov. 20, 2002, 1697-1703.

Choi, M. et al., "Genetic diagnosis by whole exome capture and massively parallel DNA sequencing", PNAS, vol. 106, No. 45, Nov. 10, 2009, 19096-19101.

Garcia-Murillas, I. et al., "Mutation tracking in circulating tumor DNA predicts relapse in early breast cancer", Science Translational Medicine, vol. 7, No. 302, Aug. 26, 2015, 1-2.

Jamal-Hanjani, M. et al., "Tracking the Evolution of Non-Small-Cell Lung Cancer", The New England Journal of Medicine, vol. 376, No. 22, Jun. 1, 2017, 2109-2121.

Jarvie, T., "Next generation sequencing technologies", Drug Discovery Today: Technologies, vol. 2, No. 3, 2005, 255-260.

Kim, H. et al., "Whole-genome and multisector exome sequencing of primary and post-treatment glioblastoma reveals patterns of tumor evolution", Genome Research, vol. 25, No. 3, Feb. 3, 2015, 316-327.

Leary, R. J. et al., "Development of Personalized Tumor Biomarkers Using Massively Parallel Sequencing", Science Translational Medicine, vol. 2, No. 20, Feb. 24, 2010, 1-8.

Ma, Xiaotu et al., "Rise and fall of subclones from diagnosis to relapse in pediatric B-acute lymphoblastic leukaemia", Nature Communications, vol. 6, Mar. 19, 2015, 1-12.

Margulies, M. et al., "Genome sequencing in microfabricated high-density picolitre reactors", Nature, vol. 437, Sep. 15, 2005, 376-380.

Margulies, M. et al., "Genome sequencing in microfabricated high-density picolitre reactors plus Supplemental Methods", Nature, vol. 437, Sep. 15, 2005, 40 pgs.

Ohsawa, M. et al., "Prenatal Diagnosis of Two Pedigrees of Fukuyama Type Congenital Muscular Dystrophy by Polymorphism Analysis", The Health and Welfare Ministry, 1994, 5 pgs.

Pergament, E. et al., "Single-Nucleotide Polymorphism-Based Non-invasive Prenatal Screening in a High-Risk and Low-Risk Cohort", Obstetrics & Gynecology, vol. 124, No. 2, Part 1, Aug. 2014, 210-218 + Appendices.

Primdahl, H. et al., "Allelic Imbalances in Human Bladder Cancer: Genome-Wide Detection With High-Density Single-Nucleotide Polymorphism Arrays", Journal of the National Cancer Institute, vol. 94, No. 3, Feb. 6, 2002, 216-223.

Samango Sprouse, C. et al., "SNP-based non-invasive prenatal testing detects sex chromosome aneuploidies with high accuracy", Prenatal Diagnosis, vol. 33, 2013, 643-649.

Bianchi, D. W. et al., "Genome-Wide Fetal Aneuploidy Detection by Maternal Plasma DNA Sequencing", Obstetrics & Gynecology, vol. 119, No. 5, May 2012, 890-901.

Palomaki, G. E. et al., "DNA sequencing of maternal plasma to detect Down syndrome: An international clinical validation study", Genetics in Medicine, vol. 13, No. 1, Nov. 2011, 913-920.

Alaeddini, R. et al., "Forensic implications of genetic analyses from degraded DNA—A review", Forensic Science International: Genetics, vol. 4, 2010, 148-157.

Alberts, B. et al., "Chapter 20: Germ Cells and Fertilization", Molecular Biology of the Cell, Fourth Edition, 2002, 1127-1156.

Alberts, B. et al., "Chapter 4: DNA and Chromosomes", Molecular Biology of the Cell, Fourth Edition, 2002, 191-234.

(56) References Cited

OTHER PUBLICATIONS

Antonarakis, S. E. et al., "Chromosome 21 and Down Syndrome: From Genomics to Pathophysiology", Nature Reviews Genetics, vol. 5, Oct. 2004, 725-738.
Beroud, C. et al., "Prenatal diagnosis of spinal muscular atrophy by genetic analysis of circulating fetal cells", The Lancet, vol. 361, Mar. 22, 2003, 1013-1014.
Bianchi, D. W., "Circulating Fetal DNA: Its Origin and Diagnostic Potential—A Review", Placenta, vol. 25, Supplemental A, May 2004, S93-S101.
Bianchi, D. W., "Review: Fetal Cells in the Maternal Circulation: Feasibility for Prenatal Diagnosis", British Journal of Haematology, vol. 105, 1999, 574-583.
Butt, A. N. et al., "Overview of Circulating Nucleic Acids in Plasma/Serum: Update on Potential Prognostic and Diagnostic Value in Diseases Excluding Fetal Medicine and Oncology", Ann. N.Y. Acad. Sci., vol. 1137, 2008, 236-242.
Deutsch, S. et al., "Detection of aneuploidies by paralogous sequence quantification", J Med Genet, vol. 41, 2004, 908-915.
Dietmaier, W. et al., "Multiple Mutation Analyses in Single Tumor Cells with Improved Whole Genome Amplification", American Journal of Pathology, vol. 154, No. 1, Jan. 1999, 83-95.
Everitt, B. S., "Medical Statistics From A to Z", 2003, 3 pages.
Hartwell, L. H. et al., "Chapter 11: The Direct Detection of Genotype Distinguishes Individual Genomes", Genetics: From Genes to Genomes, Second Edition, 2004, 371-414.
Hartwell, L. H. et al., "Chapter 13: Chromosomal Rearrangements and Changes in Chromosome Number Reshape Eukaryotic Genomes", Genetics: From Genes to Genomes, Second Edition, 2004, 441-486.
Hattori, M. et al., "The DNA sequence of human chromosome 21", Nature, vol. 405, May 18, 2000, 311-319.
Hornak, M. et al., "Aneuploidy Detection in Pigs Using Comparative Genomic Hybridization: From the Oocytes to Blastocysts", PLoS ONE, vol. 7, No. 1, Jan. 2012, 6 pages.
Illumina, "Patent Owner Illumina's Preliminary Response to Petition", Oct. 17, 2018, 75 pgs.
Illumina, "Petition for Inter Partes Review of U.S. Pat. No. 8,682,592", Jun. 13, 2019, 91 pages.
Illumina, "Plaintiff/Counterclaim Defendant Illumina, Inc.'s Amended Patent L.R. 3-3 Preliminary Invalidity Contentions for U.S. Pat. No. 8,682,592", Oct. 30, 2018, 22 pages.
Illumina, "Plaintiff/Counterclaim-Defendant Illumina, Inc.'s Patent L.R. 3-3 Contentions for U.S. Patent Preliminary Invalidity Contentions for U.S. Pat. No. 8,682,592", Oct. 9, 2018, 81 pages.
Illumina, Inc., "Declaration of David Peters, Ph.D. In Support of Petition for Inter Partes Review of U.S. Pat. No. 8,682,592", Jun. 13, 2019, 136 pages.
*Illumina, Inc. V. Natera, Inc.* "Order Re: Claim Construction", Jan. 30, 2019, 16 pgs.
Kamat, A. A. et al., "Quantification of total plasma cell-free DNA in ovarian cancer using real-time PCR", Ann N Y Acad Sci., vol. 1075, Sep. 2006, 230-234.
Lo, Y., "Noninvasive prenatal detection of fetal chromosomal aneuploidies by maternal plasma nucleic acid analysis: a review of the current state of the art", BJOG an International Journal of Obstetrics and Gynaecology, vol. 116, 2009, 152-157.
Lu, I. et al., "Establishment of a system based on universal multiplex-PCR for screening genetically modified crops", Anal. Bioanal. Chem, vol. 396, Oct. 24, 2009, 2055-2064.
Lui, Y. Y. et al., "Predominant Hematopoietic Origin of Cell-Free DNA in Plasma and Serum after Sex-Mismatched Bone Marrow Transplantation", Clinical Chemistry, vol. 48, vol. 3, 2002, 421-427.
Minkoff, E. et al., "Stem Cells, Cell Division, and Cancer", Biology Today Third Edition, Chapter 12, 2004, 10 pages.
Munne, S. et al., "Improved implantation after preimplantation genetic diagnosis of aneuploidy", Reproductive BioMedicine Online, vol. 7., No. 1., May 15, 2003, 91-97.
Natera, Inc. "Declaration of Sandra L. Haberny", May 16, 2019, 3 pages.

Natera, Inc., , "Defendant Natera, Inc.'s Invalidity Contentions Under Patent L.R. 3-3; Document Production Accompanying Invalidity Contentions Under Patent L.R. 3-4", Aug. 20, 2018, 17 pages.
Natera, Inc., , "Exhibit 8 EHRICH Invalidity Chart", Aug. 20, 2018, 16 pages.
Natera, Inc., , "Exhibits A-H to Haberny Declaration", May 16, 2019, 192 pages.
Natera, Inc., , "Motion to Dismiss", May 16, 2019, 2 pages.
Natera, Inc., , "Natera Inc.'s First Amended Answer, Affirmative Defenses and Counterclaims", Aug. 16, 2018, 28 pages.
Natera, Inc., , "Natera, Inc.'s Supplemental Objections and Response to Plaintiff Illumina, Inc.'s Interrogatory No. 8", Mar. 20, 2019, 29 pages.
Natera, Inc., , "Opening Brief in Support of Motion to Dismiss", May 16, 2019, 26 pages.
Natera, Inc., , "Petitioner Reply Per Board Order of Nov. 2, 2018 (Paper No. 10)", Nov. 9, 2018, 8 pgs.
Ng, S. B. et al., "Individualised multiplexed circulating tumour DNA assays for monitoring of tumour presence in patients after colorectal cancer surgery", Scientific Reports, vol. 7, No. 40737, Jan. 19, 2017, 11 pages.
Pastinen, T. et al., "Minisequencing: A Specific Tool for DNA Analysis and Diagnostics on Oligonucleotide Arrays", Genome Research, vol. 7, 1997, 606-614.
Peters, D., "List of Materials Considered by David Peters, Ph.D.", Jun. 13, 2019, 2 pages.
Reinert, T. et al., "Analysis of circulating tumour DNA to monitor disease burden following colorectal cancer surgery", Gut, vol. 65, 2016, 625-634.
Riva, F., "Patient-Specific Circulating Tumor DNA Detection during Neoadjuvant Chemotherapy in Triple-Negative Breast Cancer", Clinical Chemistry, vol. 63, No. 3, 2017, 691-699.
Sham, P. et al., "DNA Pooling: A Tool for Large-Scale Association Studies", Nature Reviews Genetics, vol. 3, Nov. 2002, 862-871.
Shen, R. et al., "High-throughput SNP genotyping on universal bead arrays", Mutation Research, vol. 573, Feb. 11, 2005, 70-82.
Snyder, T. M. et al., "Universal noninvasive detection of solid organ transplant rejection", PNAS, vol. 108, No. 15, Apr. 12, 2011, 6229-6234.
The International Hapmap Consort, , "The International HapMap Project", Nature, vol. 426, Dec. 18, 2003, 789-796.
Tiersch, T. R. et al., "Reference Standards for Flow Cytometry and Application in Comparative Studies of Nuclear DNA Content", Cytometry, vol. 10, Mar. 21, 1989, 706-710.
Wang, D. G. et al., "Large-Scale Identification, Mapping, and Genotyping of Single-Nucleotide Polymorphisms in the Human Genome", Science, vol. 280, May 15, 1998, 1077-1082.
Wang, T.L. et al., "Digital karyotyping", PNAS, vol. 99, No. 25, Dec. 10, 2002, 16156-16161.
Weiss, C. A., "Chapter 8: Confidence Intervals for One Population Mean", Introductory Statistics, Sixth Edition, 2002, 340-381.
Wong, K. K. et al., "Allelic imbalance analysis by high-density single nucleotide polymorphic allele (SNP) array with whole genome amplified DNA", Nucleic Acids Research, vol. 32, No. 9, May 17, 2004, 8 pages.
Zhang, L. et al., "Whole genome amplification from a single cell: Implications for genetic analysis", Proc. Nat'l. Acad. Sci. USA, vol. 89, Jul. 1992, 5847-5851.
Zimmermann, B. , "Noninvasive prenatal aneuploidy testing of chromosomes 13, 18, 21, X, and Y, using targeted sequencing of polymorphic loci, Supplemental Informtion", Prenatal Diagnosis, vol. 32, 2012, 7 pages.
Ballif, B. C. et al., "Detection of Low-Level Mosaicism by Array CGH in Routine Diagnostic Specimens", American Journal of Medical Genetics Part A, vol. 140A, 2006, 2757-2767.
Beck, J. et al., "Digital Droplet PCR for Rapid Quantification of Donor DNA in the Circulation of Transplant Recipients as a Potential Universal Biomarker of Graft Injury", Clinical Chemistry, vol. 59, No. 12, 2013, 1732-1741.
Birkenkamp-Demtroder, K. et al., "Abstract 3653: Sequencing of plasma cfDNA from patients with locally advanced bladder cancer for surveillance and therapeutic efficacy monitoring", Cancer Research, vol. 78, No. 13 Supplement, Jul. 2019, 1 page.

(56) References Cited

OTHER PUBLICATIONS

Burnham, P. et al., "Myriad Applications of Circulating Cell-Free DNA in Precision Organ Transplant Monitoring", Annals of the American Thoracic Society, vol. 14, Supplement 3, Sep. 2017, S237-S241.
Cheung, S. W. et al., "Rapid Publication: Microarray-Based CGH Detects Chromosomal Mosaicism Not Revealed by Conventional Cytogenetics", American Journal of Medical Genetics Part A, vol. 143A, 2007, 1679-1686.
Conlin, L. K. et al., "Mechanisms of mosaicism, chimerism and uniparental disomy identified by single nucleotide polymorphism array analysis", Human Molecular Genetics, vol. 19, No. 7, Jan. 6, 2010, 1263-1275.
Coombes, R. C., "Abstract P4-01-02: Early detection of residual breast cancer through a robust, scalable and personalized analysis of circulating tumour DNA (ctDNA) antedates overt metastatic recurrence", Cancer Research, vol. 79, No. 4 Supplement, Feb. 15, 2019.
Dawson, S.J. et al., "Analysis of Circulating Tumor DNA to Monitor Metastatic Breast Cancer", The New England Journal of Medicine, vol. 368, No. 13, Mar. 28, 20136, 1199-1209.
Deng, S. et al., "TNER: A Novel Background Error Suppression Method for Mutation Detection in Circulating Tumor DNA", bioRxiv, http://dx.doi.org/10.1101/214379, Nov. 5, 2017, 12 pgs.
Diehl, F. et al., "Circulating mutant DNA to assess tumor dynamics", Nature Medicine, vol. 14, No. 9, Jul. 31, 2008, 985-990.
Donaghue, C. et al., "Detection of mosaicism for primary trisomies in prenatal samples by QF-PCR and karyotype analysis", Prenatal Diagnosis, vol. 25, 2005, 65-72.
Forshew, T. et al., "Supplementary Materials for Noninvasive Identification and Monitoring of Cancer Mutations by Targeted Deep Sequencing of Plasma DNA", Sci. Transl. Med, vol. 4, May 30, 2012, 20 pgs.
Gielis, E. M. et al., "Plasma donor-derived cell-free DNA kinetics after kidney transplantation using a single tube multiplex PCR assay", PLOS One, vol. 13, No. 12, e0208207, Dec. 6, 2018, 16 pgs.
Han, S-W et al., "Predictive and Prognostic Impact of Epidermal Growth Factor Receptor Mutation in Non-Small-Cell Lung Cancer Patients Treated With Gefitinib", Journal of Clinical Oncology, vol. 23, No. 11, Apr. 10, 2005, 2493-2501.
Imielinski, M. et al., "Mapping the Hallmarks of Lung Adenocarcinoma with Massively Parallel Sequencing", Cell, vol. 150, Sep. 14, 2012, 1107-1120.
Kunishima, S. et al., "First description of somatic mosaicism in MYH9 disorders", British Journal of Haematology, vol. 128, 2005, 360-365.
Lindberg, J. et al., "Exome Sequencing of Prostate Cancer Supports the Hypothesis of Independent Tumour Origins", European Urology, vol. 63, 2013, 347-353.
Lo, Y-M D., "Non-invasive prenatal diagnosis using fetal cells in maternal blood", J. Clin. Pathol., vol. 47, 1994, 1060-1065.
Magbanua, M. J. et al., "Abstract PD2-01: Personalized serial circulating tumor DNA (ctDNA) analysis in high-risk early stage breast cancer patients to monitor and predict response to neoadjuvant therapy and outcome in the I-SPY 2 Trial", Cancer Research, vol. 79, No. 4 Supplement, Feb. 15, 2019.
Mardis, E. R., "The impact of next-generation sequencing technology on genetics", Trends in Genetics, vol. 24, No. 3, Feb. 11, 2008, 133-141.
McDonald, B. R. et al., "Abstract P4-01-21: Multiplexed targeted digital sequencing of circulating tumor DNA to detect minimal residual disease in early and locally advanced breast cancer", Cancer Research, vol. 79, No. 4 Supplement, Feb. 15, 2019.
Mertes, F. et al., "Targeted enrichment of genomic DNA regions for next-generation sequencing", Briefings in Functional Genomics, vol. 10, No. 6, Nov. 26, 2011, 374-386.
NCBI,, "dbSNP record for rs1294331", Retrieved from the Internet: <URL: www.ncbi.nlm.nih.gov/snp/?term=rs 1294331 >, 2019, 2 pgs.
NCBI,, "dbSNP record for rs1872575", Retrieved from the Internet: <URL: www.ncbi.nlm.nih.gov/snp/?term=rs1872575, 2019, 2 pgs.
NCBI,, "dbSNP record for rs2362450", Retrieved from the Internet: <URL: www.ncbi.nlm.nih.gov/snp/?term=rs2362450>, 2019, 1 pg.
NCBI,, "dbSNP record for rs2384571", Retrieved from the Internet: <URL: www.ncbi.nlm.nih.gov/snp/?term=rs2384571>, 2019, 2 pgs.
NCBI,, "dbSNP record for rs2498982", Retrieved from the Internet: <URL: www.ncbi.nlm.nih.gov/snp/?term=rs2498982>, 2019, 3 pgs.
NCBI,, "dbSNP record for rs3731877", Retrieved from the Internet: <URL: www.ncbi.nlm.nih.gov/snp/?term=rs3731877>, 2019, 2 pgs.
Newman, A. M. et al., "Integrated digital error suppression for improved detection of circulating tumor DNA", Nature Biotechnology, vol. 34, No. 5, May 2016, 547-555.
Nguyen-Dumont, T., "A high-plex PCR approach for massively parallel sequencing", BioTechniques, vol. 55, No. 2, Aug. 2013, 69-74.
Papadopoulou, E. et al., "Cell-Free DNA and RNA in Plasma as a New Molecular Marker for Prostate Cancer", Oncology Research, vol. 14, 2004, 439-445.
Poirier, K. et al., "Maternal mosaicism for mutations in the ARX gene in a family with X linked mental retardation", Human Genetics, vol. 118, Aug. 3, 2005, 45-48.
Poon, L. L. et al., "Differential DNA Methylation between Fetus and Mother as a Strategy for Detecting Fetal DNA in Maternal Plasma", Clinical Chemistry, vol. 48, No. 1, 2002, 35-41.
Saker, A. et al., "Genetic characterisation of circulating fetal cells allows non-invasive prenatal diagnosis of cystic fibrosis", Prenatal Diagnosis, vol. 26, Jul. 11, 2006, 906-916.
Shi, H. et al., "Melanoma whole-exome sequencing identifies V600E B-RAF amplification-mediated acquired B-RAF inhibitor resistance", Nature Communications, vol. 3, No. 724, Mar. 6, 2012, 8 pages.
Sigdel, T. et al., "Plasma Donor-Derived Cell-Free DNA Quantification by massively multiplex PCR Distinguishes Kidney Transplant Acute Rejection", Transplantation, vol. 102, No. 7S, Jul. 2018, S178-S179.
Sigdel, T. K. et al., "Optimizing Detection of Kidney Transplant Injury by Assessment of Donor-Derived Cell-Free DNA via Massively Multiplex PCR", Journal of Clinical Medicine, vol. 8, No. 19, Dec. 23, 2018, 17 pages.
Tynan, J. A. et al., "Restriction Enzyme-Mediated Enhanced Detection of Circulating Cell-Free Fetal DNA in Maternal Plasma", The Journal of Molecular Diagnostics, vol. 13, No. 4, Jul. 2011, 382-389.
Wikipedia,, "Buffy coat", Retrieved from "https://en.wikipedia.orgJw/index.php?title=Buffy_coat&oldid=900992886", Jun. 9, 2019, 2 pgs.
Yung, T. K. et al., "Single-Molecule Detection of Epidermal Growth Factor Receptor Mutations in Plasma by Microfluidics Digital PCR in Non-Small Cell Lung Cancer Patients", Clinical Cancer Research, vol. 15, Mar. 10, 2009, 2076-2084.

\* cited by examiner

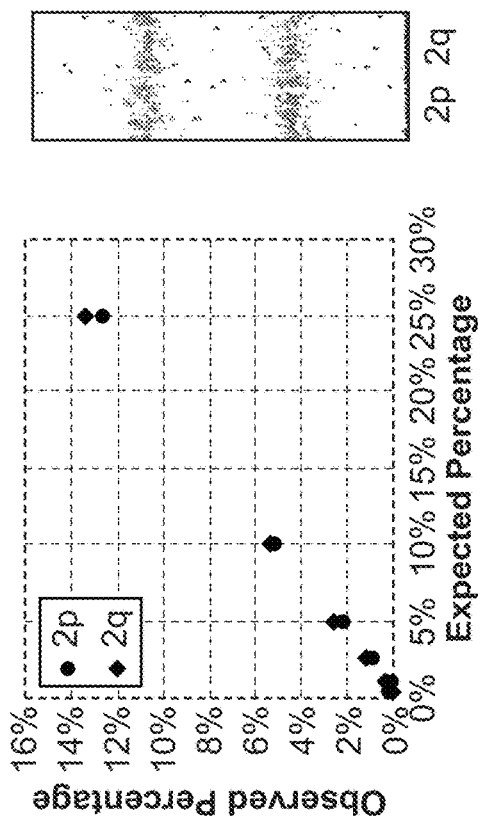
FIG. 4A
FIG. 4B
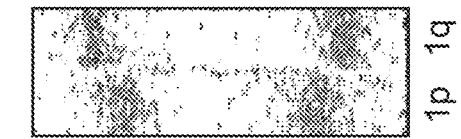
FIG. 4C
FIG. 4D
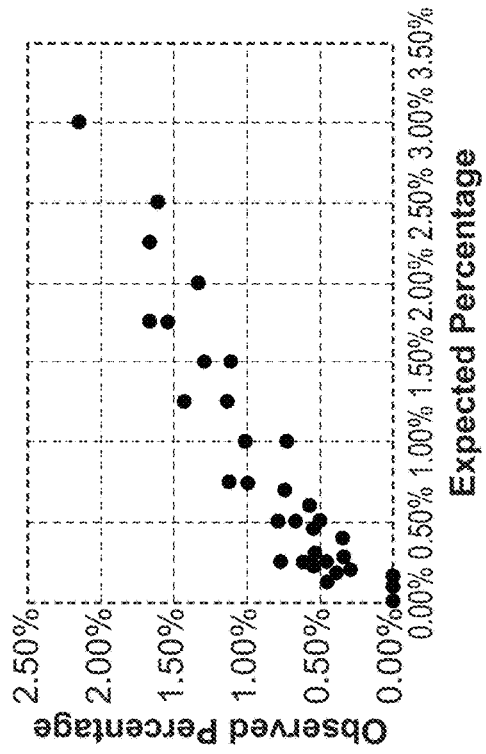
FIG. 4E

|  | count | Mean Error | St.Dev | avDOR | LODz-5 |
|---|---|---|---|---|---|
| TRANSVERSION | 1619 | 0.00155 | 0.00165 | 39,702 | 0.00973 |
| TRANSITION | 810 | 0.02193 | 0.01099 | 39,746 | 0.07688 |

FIG. 6

| Source | Gene | Chr | Position | Ref | HCC1954 WT | HCC1954 Mut | HCC2218 Mut | HCC1937 Mut | %Mut in Tumor |
|---|---|---|---|---|---|---|---|---|---|
| HCC1954 | GPHB5 | 14 | 63,784,405 | G | G | A | G | G | 25% |
|  | CLSPN | 1 | 36,226,206 | T | T | C | T | T | 24% |
|  | FLG2 | 1 | 152,328,936 | G | G | G | C | G | 38% |
| HCC2218 | TRAPPC8 | 18 | 29,470,816 | C | C | C | T | C | 51% |
|  | MTMR3 | 22 | 30,398,972 | G | G | G | G | C | 66% |
| HCC1937 | TP53 | 17 | 7,577,022 | G | G | G | G | A | 99% |
|  | TTN | 2 | 179,635,206 | G | G | G | G | C | 96% |

FIG. 8

| Gene Name: | Chr: | Position: | Notes: |
|---|---|---|---|
| TRAPPC8 | 18 | 29470816 | Mutation |
| EPHA7 | 6 | 93956553 | Filler |
| RGS22 | 8 | 101083610 | Filler |
| PIK3CA | 3 | 178928079 | Filler |
| PIK3CA | 3 | 178936050 | Filler |
| DNAH14 | 1 | 225306960 | Filler |
| TXNDC6 | 3 | 138022433 | Filler |
| TP53 | 17 | 7577022 | Mutation |
| SEC31A | 4 | 83778206 | Filler |
| ZMIZ1 | 10 | 81058322 | Filler |
| MTMR3 | 22 | 30398972 | Mutation |
| CLSPN | 1 | 36226206 | Mutation |
| FLG2 | 1 | 152328936 | Mutation |
| TTN | 2 | 179635206 | Mutation |
| GPHB5 | 14 | 63784405 | Mutation |

FIG. 9

| Mut spike # | 1 | 2 | 3 | 14 | 15 | 17 | 18 | 19 | 21 | 26 | 27 | 38 | 41 |
|---|---|---|---|---|---|---|---|---|---|---|---|---|---|
| locus | 25398284 | 25398284 | 25398284 | 7578404 | 7578404 | 7577124 | 7577124 | 7578202 | 7578275 | 7577547 | 7577547 | 7579329 | 7577022 |
| Ref | C | C | C | A | A | C | C | A | G | C | C | T | G |
| Sub | T | G | A | T | C | delC | T | C | A | A | T | C | A |
| Mean error | 0.0255 | 0.0012 | 0.0013 | 0.0003 | 0.0002 | N/A | 0.021 | 0.0002 | 0.0206 | 0.0026 | 0.0297 | 0.0151 | 0.034 |
| St.Dev | 0.0037 | 0.0011 | 0.0008 | 0.0009 | 0.0008 | N/A | 0.0089 | 0.0006 | 0.0118 | 0.0023 | 0.0107 | 0.007 | 0.0156 |
| LODz5 | 0.0442 | 0.0067 | 0.0051 | 0.0049 | 0.0043 | N/A | 0.0653 | 0.0034 | 0.0794 | 0.0139 | 0.0833 | 0.0503 | 0.1121 |
| %input | 21.25 | 21.91 | 21.45 | 24.21 | 25.05 | 27.47 | 28.23 | 36.58 | 36.17 | 24.01 | 27.46 | 36.06 | 34.41 |
| % detected | 21.51 | 22.60 | 22.81 | 26.42 | 22.91 | N/A | 22.69 | 47.69 | 60.70 | 31.36 | 31.57 | 42.02 | 32.60 |
| fold difference | 1.01 | 1.03 | 1.06 | 1.09 | 0.91 |  | 0.80 | 1.30 | 1.68 | 1.31 | 1.15 | 1.17 | 0.95 |
| %input | 8.67 | 9.25 | 8.84 | 7.90 | 8.36 | 9.80 | 10.29 | 10.34 | 10.18 | 7.80 | 9.80 | 10.13 | 9.50 |
| % detected | 9.30 | 9.71 | 9.67 | 8.95 | 8.15 | N/A | 5.61 | 15.38 | 23.76 | 13.17 | 13.06 | 12.93 | 8.87 |
| fold difference | 1.07 | 1.05 | 1.09 | 1.13 | 0.97 |  | 0.54 | 1.49 | 2.33 | 1.69 | 1.33 | 1.28 | 0.93 |
| %input | 2.19 | 2.38 | 2.24 | 1.81 | 1.93 | 2.33 | 2.46 | 2.26 | 2.22 | 1.78 | 2.32 | 2.21 | 2.06 |
| % detected | 2.51 | 2.55 | 2.68 | 2.20 | 1.95 | N/A | 1.18 | 3.67 | 5.78 | 3.35 | 3.45 | 2.98 | 2.01 |
| fold difference | 1.15 | 1.07 | 1.19 | 1.22 | 1.01 |  | 0.48 | 1.63 | 2.61 | 1.88 | 1.48 | 1.35 | 0.98 |
| %input | 1.13 | 1.23 | 1.16 | 0.92 | 0.98 | 1.19 | 1.26 | 1.14 | 1.12 | 0.91 | 1.19 | 1.12 | 1.04 |
| % detected | 1.33 | 1.35 | 1.21 | 1.00 | 0.88 | N/A | 0.61 | 1.76 | 2.96 | 1.74 | 1.75 | 1.51 | 1.03 |
| fold difference | 1.17 | 1.10 | 1.04 | 1.08 | 0.89 |  | 0.48 | 1.54 | 2.64 | 1.92 | 1.47 | 1.35 | 0.99 |
| %input | 0.462 | 0.504 | 0.474 | 0.373 | 0.398 | 0.483 | 0.513 | 0.462 | 0.453 | 0.367 | 0.483 | 0.451 | 0.420 |
| % detected | 0.500 | 0.480 | 0.540 | 0.320 | 0.370 | N/A | 0.280 | 0.752 | 1.210 | 0.730 | 0.774 | 0.588 | 0.516 |
| fold difference | 1.08 | 0.95 | 1.14 | 0.86 | 0.93 |  | 0.55 | 1.63 | 2.67 | 1.99 | 1.60 | 1.30 | 1.23 |
| %input | 0.117 | 0.127 | 0.120 | 0.094 | 0.100 | 0.122 | 0.129 | 0.115 | 0.113 | 0.092 | 0.122 | 0.113 | 0.105 |
| % detected | 0.131 | 0.121 | 0.138 | 0.113 | 0.098 | N/A | 0.086 | 0.174 | 0.342 | 0.185 | 0.191 | 0.175 | 0.140 |
| fold difference | 1.12 | 0.95 | 1.15 | 1.21 | 0.98 |  | 0.67 | 1.51 | 3.02 | 2.01 | 1.57 | 1.55 | 1.33 |
| %input | 0.047 | 0.051 | 0.048 | 0.038 | 0.040 | 0.049 | 0.052 | 0.046 | 0.045 | 0.037 | 0.049 | 0.045 | 0.042 |
| % detected | 0.061 | 0.057 | 0.059 | 0.017 | 0.026 | N/A | 0.063 | 0.075 | 0.113 | 0.07 | 0.126 | 0.066 | 0.097 |
| fold difference | 1.30 | 1.12 | 1.23 | 0.45 | 0.65 |  | 1.22 | 1.63 | 2.49 | 1.90 | 2.59 | 1.46 | 2.31 |

FIG. 13

CELL FREE DNA DIAGNOSTIC TESTING STANDARDS

CROSS-REFERENCE TO RELATED APPLICATIONS

This application is a continuation-in-part application of U.S. application Ser. No. 14/498,629, filed Sep. 26, 2014, which claims the benefit of U.S. Provisional Application Ser. No. 61/883,735, filed Sep. 27, 2013 and claims the benefit of U.S. Provisional Application Ser. No. 61/978,658, filed Apr. 11, 2014. This application is a continuation-in-part application of U.S. application Ser. No. 14/882,763, filed Oct. 14, 2015. U.S. application Ser. No. 14/882,763, filed Oct. 14, 2015 claims the benefit of U.S. Provisional Application Ser. No. 62/066,514, filed Oct. 21, 2014; U.S. Provisional Application Ser. No. 62/146,188, filed Apr. 10, 2015; U.S. Provisional Application Ser. No. 62/147,377, filed Apr. 14, 2015; and U.S. Provisional Application Ser. No. 62/148,173, filed Apr. 15, 2015, and is a continuation-in-part application of U.S. application Ser. No. 14/538,982, filed Nov. 24, 2014, and is a continuation-in-part application of U.S. application Ser. No. 14/692,703, filed Apr. 21, 2015. U.S. application Ser. No. 14/538,982, filed Nov. 24, 2014 claims the benefit of U.S. Provisional Application Ser. No. 61/982,245, filed Apr. 21, 2014; U.S. Provisional Application Ser. No. 61/987,407, filed May 1, 2014; U.S. Provisional Application Ser. No. 61/994,791, filed May 16, 2014, and U.S. Provisional Application Ser. No. 62/066,514, filed Oct. 21, 2014. U.S. application Ser. No. 14/692,703, filed Apr. 21, 2015, claims the benefit of U.S. Provisional Application Ser. No. 61/982,245, filed Apr. 21, 2014; U.S. Provisional Application Ser. No. 61/987,407, filed May 1, 2014; U.S. Provisional Application Ser. No. 62/066,514, filed Oct. 21, 2014; U.S. Provisional Application Ser. No. 62/146,188, filed Apr. 10, 2015; U.S. Provisional Application Ser. No. 62/147,377, filed Apr. 14, 2015; U.S. Provisional Application Ser. No. 62/148,173, filed Apr. 15, 2015; and U.S. Provisional Application Ser. No. 61/994,791, filed May 16, 2014. Each of these applications cited above is hereby incorporated by reference in its entirety.

SEQUENCE LISTING

The instant application contains a Sequence Listing which has been submitted electronically in ASCII format and is hereby incorporated by reference in its entirety. Said ASCII copy, created on Dec. 18, 2015, is named N009US02_SL.txt and is 4,370 bytes in size.

FIELD OF THE INVENTION

The invention is in the field of nucleic acid-based diagnostics

BACKGROUND OF THE INVENTION

Cell free DNA found in the blood and other bodily fluids can be used to detect and diagnose many genetic disorders. Numerous methods exist for non-invasive prenatal genetic diagnostics. Non-invasive prenatal genetic diagnoses can be performed on cell-free DNA, e.g., obtained from blood, from a patient. Cell-free DNA can also be used to detect or monitor the presence of tumor cells in patients. Such methods are complex to carry out and are subject to numerous errors resulting in imprecision and inaccuracy. It is important for commercial laboratories to demonstrate proficiency in testing in order to obtain regulatory approval for carrying out such tests. Accordingly, it is necessary for laboratories carrying out such procedures to engage in proficiency testing using standards for analysis. Such standard testing can be problematic given the relative scarcity of naturally occurring samples and the variability between such samples. Provided herein are methods and compositions for addressing this problem.

SUMMARY OF THE INVENTION

Provided below is a non-exhaustive list of some embodiments of the invention. An embodiment of the invention is a prenatal nucleic acid proficiency testing standard composition, comprising a first nucleosomal nucleic acid preparation derived from a first cell source and a second nucleosomal nucleic acid preparation from a second cell source, wherein the quantity of the first nucleic acid preparation is greater than the quantity of the second nucleic acid preparation. In another embodiment, the invention is a prenatal nucleic acid proficiency testing standard composition, comprising a first nucleosomal nucleic acid preparation derived from a first cell source and a second nucleosomal nucleic acid preparation from a second cell source, wherein the quantity of the first nucleic acid preparation is approximately equal to the quantity of the second nucleic acid preparation.

In some embodiments of the prenatal nucleic acid proficiency testing standard composition, the first nucleosomal nucleic acid preparation is derived from a primary cell source. In some embodiments, the first nucleosomal nucleic acid preparation is derived from a cell line. In some embodiments the first nucleosomal nucleic acid preparation is derived from a cell line and the second nucleosomal nucleic acid preparation is one or more synthetic oligonucleotides. In some embodiments the first cell source and the second cell source are cell lines. In some embodiments the first cell source and the second cell source are primary cell sources. In some embodiments primary cell source is blood cells from a buffy coat layer.

In some embodiments of the subject compositions nucleosomal nucleic acid preparation has been prepared with an endonuclease. The endonuclease can be a micrococcal endonuclease. In some embodiments the first nucleosomal nucleic acid preparation and the second nucleosomal nucleic acid are one or more nucleosomal ladder components. In some embodiments the first nucleosomal nucleic acid preparation and the second nucleosomal nucleic acid comprise a monosomal nucleosomal ladder fraction. In some embodiments the first nucleosomal nucleic acid preparation comprises a disomal nucleosomal ladder fraction. In some embodiments the first nucleosomal nucleic acid preparation comprises a trisomal nucleosomal ladder fraction. In some embodiments, the second nucleosomal nucleic acid preparation comprises a monosomal nucleosomal ladder fraction. In some embodiments the second nucleosomal nucleic acid preparation comprises a trisomal nucleosomal ladder fraction. In some embodiments, the second nucleosomal nucleic acid preparation comprises a disomal nucleosomal ladder fraction.

In some embodiments the amount of the second nucleosomal nucleic acid preparation is less than 40% of the total nucleic acid in the composition. In some embodiments the amount of the second nucleosomal nucleic acid preparation is less than 30% of the total nucleic acid in the composition. In some embodiments the second nucleosomal nucleic acid preparation is less than 20% of the total nucleic acid in the composition. In some embodiments the amount of the second nucleosomal nucleic acid preparation is less than 10% of the total nucleic acid in the composition.

The first cell source and the second cell source may be from genetically related individuals, including embodiments for use in the analysis of fetal DNA. In some embodiments the first cell source is the mother of the second cell source. In some embodiments the first cell source is the father of the second cell source. In some embodiments the first cell source is a sibling of the second cell source.

An embodiment of the invention is a composition comprising a cancer cell nucleic acid proficiency testing standard for diagnostics that detect cell free cancer DNA, comprising a first nucleosomal nucleic acid preparation derived from a first cell source and a second nucleosomal nucleic acid preparation from a second cell source, wherein the quantity of the first nucleic acid preparation is greater than the quantity of the second nucleic acid preparation.

In another embodiment, the invention is a cancer nucleic acid proficiency testing standard composition, comprising a first nucleosomal nucleic acid preparation derived from a first cell source and a second nucleosomal nucleic acid preparation from a second cell source, wherein the quantity of the first nucleic acid preparation is approximately equal to the quantity of the second nucleic acid preparation.

In some embodiments the cancer cell nucleic acid proficiency testing standard composition comprises a first nucleosomal nucleic acid preparation that is derived from a primary cell source. In some embodiments the first nucleosomal nucleic acid preparation is derived from a cell line. In some embodiments the first cell source and the second cell source are cell lines. In some embodiments the first cell source and the second cell source are primary cell sources. In some embodiments the first nucleosomal nucleic acid preparation is derived from a cell line and the second nucleosomal nucleic acid preparation is one or more synthetic oligonucleotides.

In some embodiments of the subject compositions, nucleosomal nucleic acid preparation can be been prepared with an endonuclease. The endonuclease can be a micrococcal endonuclease. In some embodiments the first nucleosomal nucleic acid preparation and the second nucleosomal nucleic acid are nucleosomal ladder fractions. In some embodiments the first nucleosomal nucleic acid preparation and the second nucleosomal nucleic acid comprise monosomal nucleosomal ladder fractions. In some embodiments the first nucleosomal nucleic acid preparation comprises a disomal nucleosomal ladder fraction. In some embodiments the first nucleosomal nucleic acid preparation comprises a trisomal nucleosomal ladder fraction. In some embodiments, the second nucleosomal nucleic acid preparation comprises a disomal nucleosomal ladder fraction. In some embodiments the second nucleosomal nucleic acid preparation comprises a trisomal nucleosomal ladder fractions. In some embodiments, second nucleosomal nucleic acid preparation comprises a disomal nucleosomal ladder fractions. In some embodiments the second nucleosomal nucleic acid preparation comprises a trisomal nucleosomal ladder fractions.

In some embodiments the amount of the second nucleosomal nucleic acid preparation is less than 40% of the total nucleic acid in the composition. In some embodiments the amount of the second nucleosomal nucleic acid preparation is less than 30% of the total nucleic acid in the composition. In some embodiments the second nucleosomal nucleic acid preparation is less than 20% of the total nucleic acid in the composition. In some embodiments the amount of the second nucleosomal nucleic acid preparation is less than 10% of the total nucleic acid in the composition.

The first cell source and the second cell source may be from genetically related individuals, from the same individual, or from genetically unrelated individuals. In some embodiments the first cell source is the mother of the second cell source. In some embodiments the first cell source is non-cancerous tissue and the second cell source is a corresponding cancer cell culture from the same individual.

The invention also includes sets of the subject cell free DNA diagnostic testing standards, wherein the set comprises at least two cell free DNA diagnostic testing standards. In some embodiments, the sets can comprise cell free DNA diagnostic testing standards that are the same as one another with respect to the identity of the cell sources, but differ with respect to one another with respect to the ratios of the different nucleosomal nucleic acid components of the mixture.

The invention also includes methods of making prenatal nucleic acid proficiency testing standard compositions and the prenatal nucleic acid proficiency testing standard compositions made by the methods. Embodiments of such methods include mixing a first nucleosomal nucleic acid preparation derived from a first cell source, and a second nucleosomal nucleic acid preparation from a second cell source, wherein the quantity of the first nucleic acid preparation is greater than the quantity of the second nucleic acid preparation. Embodiments of the subject methods include methods of making all of the compositions described herein.

The invention also includes methods of making the subject cell-free nucleic acid diagnostic proficiency testing standard compositions prepared by the subject methods. Embodiments of such methods include mixing a first nucleosomal nucleic acid preparation derived from a first cell source, and a second nucleosomal nucleic acid preparation from a second cell source, wherein the quantity of the first nucleic acid preparation is greater than (or in some embodiments, equal to) the quantity of the second nucleic acid preparation. Embodiments of the subject methods include methods of making all of the compositions described herein. The cell-free nucleic acid diagnostic proficiency testing standard compositions prepared by the subject methods can be used for testing proficiency to perform diagnosis or detection of a wide range of genetic disorders such as cancer or fetal chromosomal abnormalities.

BRIEF DESCRIPTION OF THE DRAWINGS

FIG. 1A shows mixtures of 96 patient-derived cfDNAs, concentrated 50 fold. FIG. 1B shows cell line-derived artificial cfDNA. FIG. 1C shows white blood cell-derived artificial cfDNA.

FIGS. 4A-4E show the detection of copy number variants in cell-free DNA diagnostic standards (PlasmArt standards).

FIG. 6 shows a table containing count, mean error, standard deviation, avDOR and LODz5 for transversion and transition events across all bases assessed.

FIG. 8 shows a table of single nucleotide variation (SNV) data assayed across four cell lines.

FIG. 9 shows a sub-primer pool containing 7 assays targeting seven single nucleotide variations.

FIG. 13 is a summary of mutant spike detection data.

DETAILED DESCRIPTION OF THE INVENTION

Figure 1A:
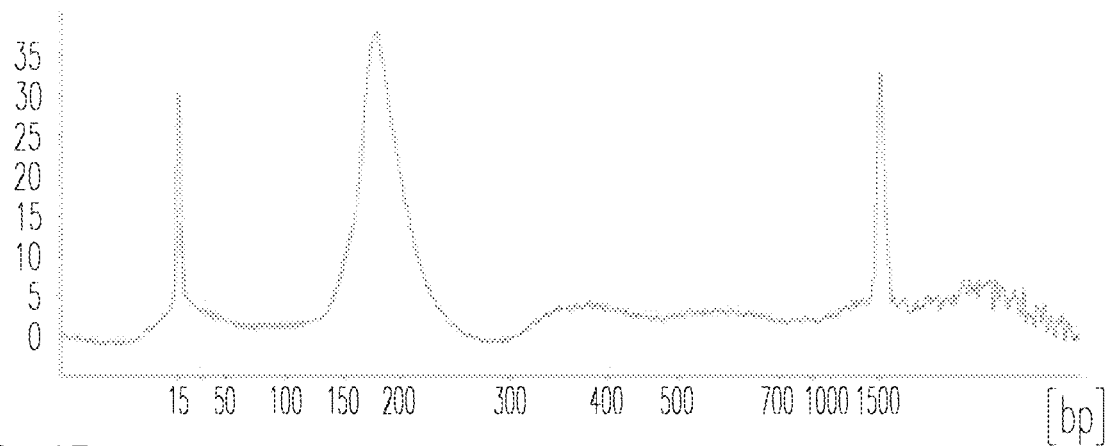
FIGS. 1A-1C show size distributions of natural and artificial cfDNA (cell free).

The present invention provides nucleic acid standards that are compositions useful for proficiency testing of laboratories engaging in the analysis of circulating cell-free DNA samples, including cell-free DNA that is used for prenatal genetic analysis or cell-free DNA that is used for the detection or analysis of cancerous cells. These standards are designed to simulate naturally occurring cell free circulating DNA found in the bloodstream of a test subject, e.g., a pregnant woman or suspected cancer patient. It was unexpected that artificially created standards could produce results that were sufficiently close to results obtained from actual patient data so as to provide a useful substitute for a naturally occurring cell-free DNA sample. These artificially created standards can be used to simulate cell-free DNA samples obtained directly from a natural source. Many commercial testing laboratories are regulated, such laboratories have need to develop standardized testing procedures in order to obtain approval or accreditation. The development of such standardized testing procedures can be facilitated by using standards for analysis. A problem with such biological standards is their limited availability. This problem may be addressed using the subject composition and related methods, which can be used to produce large quantities of genetic testing standards, thereby facilitating the commercialization of the tests of interest.

A non-invasive prenatal diagnostic assay can detect and analyze cell-free DNA that is a mixture of maternally derived DNA and DNA derived from the fetus carried by the mother. In some embodiments, the mother may be carrying more than one fetus, e.g. twins, and the subject cell free DNA standard is designed to simulate such cases of multiple pregnancies.

Some embodiments of the invention are compositions comprising at least two nucleosomal nucleic acid preparations, wherein each nucleosomal nucleic acid preparation is derived from a different cell source. In some embodiments of the invention, the compositions can comprise more than two nucleosomal nucleic acid preparations derived from different cell sources. In some embodiments, the compositions can comprise a first nucleosomal nucleic acid preparation derived from a first cell source and a second nucleosomal nucleic acid derived from a second cell source. In some embodiments, the different cell sources in a given preparation are different from one another. In various embodiments, different ratios of the nucleosomal nucleic acid preparation components of the subject compositions are provided for, thereby enabling the creation of proficiency testing standards that simulate a given fetal fraction of interest. In some embodiments, different ratios of the nucleosomal nucleic acid preparation components of the subject compositions are provided for, thereby enabling the creation of proficiency testing standards that simulate different stages of cancer.

The subject prenatal nucleic acid proficiency testing standard compositions may be created so as to simulate a wide variety of potential patient samples. The patient samples can vary with respect to the relative amounts of maternally derived cell free nucleic acid to fetal he derived cell free nucleic acid. An additional source of potential variation is chromosomal abnormalities or genetic alleles associated with a genetic disease that are present in the fetus or the mother.

Examples of chromosomal abnormalities include various aneuploidies, deletions, copy number variations, translocations, and the like. Examples of aneuploidies include, trisomy 21, trisomy 18, trisomy 13, Turner's syndrome, Klinefelter's syndrome, XYY, XXX, and the like. Additionally, in some embodiments the source of variation may be a genetic allele associated with a genetic disease or carrier state, such as cystic fibrosis, sickle cell anemia, thalassemia's, Tay-Sachs disease, Canavan disease, and the like. Similarly, various cancer cell genomes can comprise aneuploidies, deletions, copy number variations, translocations, and the like. The patient samples can vary with respect to the relative amounts cell free nucleic acid derived from the cancer cell of interest and from other non-cancerous cells in the body of the patient.

The ratio of total fetal DNA to total maternal DNA (maternal DNA plus fetal DNA) can, for the sake of convenience, be referred to as the fetal fraction. Embodiments of cell free DNA diagnostic testing standards for prenatal nucleic acid proficiency testing can be produced to mimic a wide variety of potential fetal fractions present in actual maternal cell free circulating DNA samples obtained from pregnant women. Fetal fractions in the range of 0% to 100%, as well as all increments within this range can be simulated in various embodiments of the subject compositions. In some embodiments, the subject compositions comprise a first nucleosomal nucleic acid preparation derived from a first cell source and a second nucleosomal nucleic acid preparation derived from a second cell source where in the quantity of the first nucleic acid preparation is greater than the quantity of the second nucleic acid preparation. In some embodiments, the first cell source will be representative of the mother and the second cell source will be representative of the fetus. In some embodiments the second size-fractionated nucleic acid preparation will be less than 40% of the total nucleic acid amount in the final preparation. In some embodiments the second size-fractionated nucleic acid preparation will be less than 30% of the total nucleic acid amount in the final preparation. In some embodiments the second size-fractionated nucleic acid preparation will be less than 20% of the total nucleic acid amount in the final preparation. In some embodiments the second size-fractionated nucleic acid preparation will be less than 10% of the total nucleic acid amount in the final preparation.

In embodiments of the invention for use with the analysis of cell-free derived from cancer cells, the ratio of total cell free cancer cell derived DNA to total cell free DNA (cell free cancer cell derived DNA plus other cell free DNA found in the sample) can, for the sake of convenience, be referred to as the tumor fraction. Cell-free cancer nucleic acid analysis proficiency testing standards can be produced to mimic a wide variety of tumor fractions present in cell free circulating DNA samples obtained from patients or suspected patients. Tumor fractions in the range of 0% to 100%, as well as all increments within this range can be simulated in various embodiments of the subject compositions. In some embodiments, the subject compositions comprise a first nucleosomal nucleic acid preparation derived from a first cell source and a second nucleosomal nucleic acid preparation derived from a second cell source wherein the quantity of the first nucleic acid preparation is greater than the quantity of the second nucleic acid preparation. In some embodiments, the first cell source will be representative of the patient germline (noncancerous) and the second cell source will be representative of the cancerous cells. In some embodiments the second size-fractionated nucleic acid preparation will be less than 40% of the total nucleic acid amount in the final preparation. In some embodiments the second nucleosomal nucleic acid preparation will be less than 30% of the total nucleic acid amount in the final preparation. In some embodiments the second size-fractionated nucleic acid preparation will be less than 20% of the total nucleic acid amount in the final preparation. In some embodiments the second size-fractionated nucleic acid preparation will be less than 10% of the total nucleic acid amount in the final preparation. It will be understood by person skilled in the art that although the previous description refers to a first cell source and a second cell source, embodiments of the invention also provided for that include more than two cell sources, for example the sample may be prepared from one tumor cell line and 3 separate non-tumor cell lines. In another embodiment, the invention also provides for more than two cell sources, such as one non-tumor cell line and two or more separate tumor cell lines, which can be useful to simulate tumor heterogeneity.

The nucleosomal fractions derived from nucleosomal ladders are said to be "fractions" because they do not contain all sizes of the DNA fragments in the nucleosomal preparation derived from the first cell source or the second cell source. By employing nucleosomal nucleic acid preparations, a practical upper size limit is applied, the specific size limit depending on whether monosomal, disomal, or trisomal fraction containing preparations are used in the particular embodiment.

The compositions include multiple possible combinations of nucleosomal fractions from the first cell source and the second cell source. In some embodiments the nucleosomal nucleic acid preparation prepared from the first cell source comprises (1) the monosomal fraction, the monosomal fraction and the disomal fraction, or the monosomal fraction and the disomal fraction and the trisomal fraction. In some embodiments the nucleosomal nucleic acid preparation prepared from the second cell source comprises (1) the monosomal fraction, the monosomal fraction and the disomal fraction, or the monosomal fraction and the disomal fraction and the trisomal fraction. The provided embodiments included all possible combinations of the nucleosomal fractions, (1) the monosomal fraction from the first cell source in combination with the monosomal fraction from the second cell source, (2) the monosomal fraction from the first cell source in combination with the monosomal and disomal fractions from the second cell source, (3) the monosomal fraction from the first cell source in combination with the monosomal, disomal and trisomal fractions from the second cell source, (4) the monosomal and disomal fractions from the first cell source in combination with the monosomal fraction from the second cell source, (5) the monosomal and disomal fractions from the first cell source in combination with the monosomal and disomal fractions from the second cell source, (6) the monosomal and disomal fractions from the first cell source in combination with the monosomal, disomal and trisomal fractions from the second cell source, (7) the monosomal, disomal, and trisomal fractions from the first cell source in combination with the monosomal fraction from the second cell source, (8) the monosomal, disomal, and trisomal fractions from the first cell source in combination with the monosomal and disomal fractions from the second cell source, (9) the monosomal, disomal, and trisomal fractions from the first cell source in combination with the monosomal, disomal and trisomal fractions from the second cell source. As used herein, monosomal nucleosomal fraction can also be referred to as the mononucleosomal fraction, disomal nucleosomal fraction can also be referred to as the dinucleosomal fraction, and trisomal nucleosomal fraction can also be referred to as the trinucleosomal fraction.

In some embodiments, the composition includes a set of nucleic acid standards having two or more nucleic acid standard compositions, each standard composition comprising a mixture of a first nucleosomal nucleic acid preparation generated in vitro from a cancer cell source, and a second nucleosomal nucleic acid preparation generated in vitro from a matched non-cancer cell source.

In some embodiments, the composition includes a set of nucleic acid standards having two or more nucleic acid standard compositions, each standard composition comprising a mixture of a first nucleosomal nucleic acid preparation generated in vitro from a cancer cell source, and a second nucleosomal nucleic acid preparation generated in vitro from a matched non-cancer cell source, where the ratio of the quantity of the first nucleosomal nucleic acid preparation and the quantity of the second nucleosomal nucleic acid preparation in each nucleic acid standard composition of the set of nucleic acid compositions is different, where the first nucleosomal fraction comprises between 1% and 90% of the total nucleosomal nucleic acids in at least two of the two or more nucleic acid standard compositions, and where a copy number of a chromosomal region known to exhibit copy number variation in cancer, is different in the first nucleosomal nucleic acid preparation compared to the second nucleosomal nucleic acid preparation.

In some embodiments, the composition comprises a set of nucleic acid standards having between 2 and 10 nucleic acid standard compositions. In another embodiment, the composition comprises a set of nucleic acid standard compositions comprising between 2, 3, 4, 5, 6, 7, 8, 9, 10, 11, 12, 15, 20, 25 or 50 nucleic acid standard compositions on the low end and 3, 4, 5, 6, 7, 8, 9, 10, 11, 12, 15, 20, 25, 50, 100 or 250 nucleic acid standard compositions on the high end. In yet another embodiment, the composition comprises at least two nucleic acid standard compositions having between 0.01% and 1% of the first nucleic acid preparation compared to the second nucleic acid preparation. In another embodiment, the composition includes a set of at least 3, 4, 5, 6, 7, 8, 9, 10, 11 or 12 nucleic acid standard compositions, where the set of nucleic acid standard compositions comprises between 0.01% and 1% of the first nucleic acid preparation compared to the 2, 3, 4, 5, 6, 7, 8, 9, 10, 11 or 12 nucleic acid preparations. In another embodiment, the composition comprises between 2, 3, 4, 5, 6, 7, 8, 9 or 10 nucleic acid standard compositions on the low end and 3, 4, 5, 6, 7, 8, 9, 10, 11, 12, 15 or 20 nucleic acid standard compositions on the high end, where the set further includes between 0.01% and 1% of the first nucleic acid preparation compared to the second nucleic acid preparation.

In another embodiment, the composition includes a set of nucleic acid standard compositions having between 0.01% and 1% of the first nucleic acid preparation compared to the second nucleic acid preparation, and where nucleic acids from the first nucleic acid preparation is between 0.01, 0.02, 0.03, 0.04, 0.05, 0.075, 0.1, 0.2, 0.3, 0.4, 0.5, 0.6, 0.7, 0.8, 0.9 or 1 on the low end and 0.02, 0.03, 0.04, 0.05, 0.075, 0.1, 0.2, 0.3, 0.4, 0.5, 0.6, 0.7, 0.8, 0.9, 1, 2, 3, 4, 5 or 10 on the high end as much as nucleic acids from the second nucleic acid preparation. In some embodiments, the first nucleic acid preparation is a nucleic acid preparation generated in vitro from a cancer cell source. In some embodiments, the second nucleic acid preparation is a nucleic acid preparation generated in vitro from a matched non-cancer cell source.

In some embodiments, the composition includes a set of nucleic acid standard compositions where at least one of the two or more nucleic acid standard compositions includes a synthetic oligonucleotide between 50 and 500 base pairs in length comprising at least 50 contiguous nucleotides having a sequence that is at least 90% identical to a genomic sequence comprising or flanking a mutation correlated with cancer selected from a single nucleotide variant, an indel, or a gene fusion junction. In some embodiments, the composition includes a synthetic oligonucleotide of between 75 and 400 base pairs in length. In another embodiment, the composition includes a synthetic oligonucleotide of between 100 and 350 base pairs in length. In yet another embodiment, the composition includes a synthetic oligonucleotide of between 125 and 300 base pairs in length. In some embodiments the synthetic oligonucleotide comprises at least 50 contiguous nucleotides having a sequence that is at least 91%, 92%, 93%, 94%, 95%, 96%, 97%, 98%, 99% or 100% identical to a genomic sequence comprising or flanking a mutation correlated with cancer selected from a single nucleotide variant, an indel, or a gene fusion junction. For the purposes of the present application, a small indel is considered to reside between 1 base pair and 10 base pairs for a deletion and 1 base pair and 10 base pairs for an insertion. Likewise, a medium indel for the purpose of this application is considered to be between 10 base pairs and 200 base pairs for a deletion and 10 base pairs and 200 base pairs for an insertion. A large indel for the purpose of this application is considered to be a deletion, or insertion, of over 200 base pairs to a megabase in length.

In some embodiments, the composition includes a set of nucleic acid standard compositions where at least one of the two or more nucleic acid standard compositions includes a synthetic oligonucleotide of between 50 and 500 base pairs in length comprising at least 75 contiguous nucleotides having a sequence that is at least 90% identical to a genomic sequence comprising or flanking a mutation correlated with cancer selected from a single nucleotide variant, an indel, or a gene fusion junction location. In some embodiments, at least one of the two or more nucleic acid standard compositions includes a synthetic oligonucleotide of between 75 and 400 base pairs in length comprising at least 100 contiguous nucleotides having a sequence that is at least 90% identical to a genomic sequence comprising or flanking a mutation correlated with cancer selected from a single nucleotide variant, an indel, or a gene fusion junction. In other embodiment, at least one of the two or more nucleic acid standard compositions includes a synthetic oligonucleotide of between 50, 75 or 100 base pairs in length on the low end and 300, 350, 400, 450 or 500 base pairs in length on the high end, and where the synthetic oligonucleotide includes at least 25, 50, or more contiguous nucleotides having a sequence that is at least 90%, 91%, 92%, 93%, 94%, 95%, 96%, 97%, 98%, 99% or 100% identical to a genomic sequence comprising or flanking a mutation correlated with cancer selected from a single nucleotide variant, an indel, or a gene fusion junction.

In some embodiments, the set of nucleic acid standards comprises two or more nucleic acid standard compositions, each standard composition comprising a different mixture of a wild-type nucleosomal nucleic acid preparation, typically generated in vitro, from a wild-type cell source and a synthetic oligonucleotide between 50 and 500 base pairs in length comprising at least 50 contiguous nucleotides having a sequence that is at least 90% identical to a genomic sequence comprising or flanking a mutation correlated with cancer selected from a single nucleotide variant, an indel, or a gene fusion junction, where the synthetic oligonucleotide is present in different concentrations in different standard compositions of the set at a concentration of between 0.01% and 20% of the concentration of nucleic acids from the wild-type nucleosomal nucleic acid preparation. In some embodiments, at least one of the standard compositions of the set further includes a CNV nucleosomal nucleic acid preparation generated in vitro from a cancer cell source exhibiting aneuploidy at a chromosomal region where aneuploidy has been correlated with cancer. Thus, in some embodiments, at least one standard composition of the set includes both the synthetic oligonucleotide at a concentration of between 0.01, 0.02, 0.05, 0.1 and 1% on the low end to 0.1, 0.2, 0.5, 1, 2, 5, 10 and 20% on the high end of the range of the total concentration of nucleic acids in the standard composition, and the CNV nucleosomal nucleic acid preparation at a concentration of between 0.01, 0.02, 0.05, 0.1 and 1% on the low end to 0.1, 0.2, 0.5, 1, 2, 5, 10 and 20% on the high end of the range of the total concentration of nucleic acids in the standard composition. In certain embodiments, all but one of the nucleic acid standard compositions in the set, comprises both the synthetic oligonucleotide and the CNV nucleosomal nucleic acid preparation. Some embodiments provided herein, are kits that include the nucleic acid standard sets provided herein in separate tubes, vessels, or chamber. These kits can also include primers for amplifying the synthetic oligonucleotide and/or at least a portion of the chromosomal region where aneuploidy has been correlated with cancer.

In some embodiments, at least two of the standard compositions of the set each include a different CNV nucleosomal nucleic acid preparation generated in vitro from a cancer cell source exhibiting aneuploidy at a chromosomal region where aneuploidy has been correlated with cancer. In some embodiments, each of the standard compositions of the nucleic acid set include a distinct CNV nucleosomal nucleic acid preparation generated in vitro from a cancer cell source exhibiting aneuploidy at a chromosomal region where aneuploidy has been correlated with cancer.

In some embodiments, the set of nucleic acid standard compositions comprises between 2 and 10 nucleic acid standard compositions. In another embodiment, the set of nucleic acid standard compositions comprises between 2, 3, 4, 5, 6, 7, 8, 9, 10, 11, 12, 15, 20, 25 or 50 nucleic acid standard compositions on the low end and 3, 4, 5, 6, 7, 8, 9, 10, 11, 12, 15, 20, 25, 50, 100 or 250 nucleic acid standard compositions on the high end. In yet another embodiment, the set of nucleic acid standard compositions comprises at least two standard compositions having between 0.01% and 1% of the first nucleic acid preparation compared to the second nucleic acid preparation. In another embodiment, the set of nucleic acids includes at least 3, 4, 5, 6, 7, 8, 9, 10, 11 or 12 nucleic acid standard compositions, where the set of nucleic acid standard compositions comprises between 0.01% and 1% of the first nucleic acid preparation compared to the 2, 3, 4, 5, 6, 7, 8, 9, 10, 11 or 12 nucleic acid preparations. In another embodiment, the set of nucleic acid standard compositions includes between 2, 3, 4, 5, 6, 7, 8, 9 or 10 nucleic acid standard compositions on the low end and 3, 4, 5, 6, 7, 8, 9, 10, 11, 12, 15 or 20 nucleic acid standard compositions on the high end, where the set of nucleic acid standard compositions further includes between 0.01% and 1% of the first nucleic acid preparation compared to the second nucleic acid preparation.

In another embodiment, the set of nucleic acid standards comprises between 0.01% and 1% of the first nucleic acid preparation compared to the second nucleic acid preparation, and where nucleic acids from the first nucleic acid preparation is between 0.01, 0.02, 0.03, 0.04, 0.05, 0.075, 0.1, 0.2, 0.3, 0.4, 0.5, 0.6, 0.7, 0.8, 0.9 or 1 on the low end and 0.02, 0.03, 0.04, 0.05, 0.075, 0.1, 0.2, 0.3, 0.4, 0.5, 0.6, 0.7, 0.8, 0.9, 1, 2, 3, 4, 5 or 10 on the high end as much as nucleic acids from the second nucleic acid preparation. In some embodiments, the first nucleic acid preparation is a nucleic acid preparation generated in vitro from a cancer cell source or a tumor fraction. In some embodiments, the second nucleic acid preparation is a nucleic acid preparation generated in vitro from a matched non-cancer cell source.

In some embodiments, the set of nucleic acid standard compositions includes a standard composition with a known average allelic imbalance ratio. The standard composition can have an average allelic imbalance ratio for a particular allelic state indicative of aneuploidy of the chromosome segment, of between 0.4 and 10% to mimic an average allelic imbalance of an allele in a sample that is present in low concentrations, such as would be expected for circulating free DNA (cfDNA) from a fetus or from a tumor.

In some embodiments, the standard compositions as disclosed herein, are used as genetic reference points to detect or identify one or more genetic variations the sample under investigation.

Accordingly, in certain aspects, a standard composition can be prepared by a method comprising fragmenting a nucleic acid sample into fragments that mimic the size of fragments of DNA circulating in plasma of the individual. In certain aspects, a control sample is used in parallel that has no aneuploidy for the chromosome segment under investigation.

In illustrative embodiments, data from one or more standard compositions provided herein can be analyzed in a method along with a test sample. For example, where a test sample is a plasma sample suspected of containing circulating free tumor DNA, the method can be also be performed for a control sample from a tumor from the subject along with the plasma sample. As disclosed herein, the control sample can be prepared by fragmenting the sample to mimic the DNA composition of an apoptotic cell, especially when the sample is from an individual afflicted with cancer. As such, data from the control sample will increase the confidence of detection of chromosomal aneuploidy by the standard composition in the sample.

In certain embodiments, provided herein is a method for determining whether circulating tumor nucleic acids are present in a sample, comprising detecting circulating tumor nucleic acids in the sample and on a control sample with a known average allelic imbalance ratio. The control sample, for example, can be a sample from a tumor of the individual. In some embodiments, the control sample has an average allelic imbalance expected for the sample under analysis. For example, the control sample can have an average allelic imbalance (AAI) of between 0.5% and 5% or an average allelic imbalance ratio of 0.5%. In some embodiments, the control sample is one or a set of nucleic acid standards provided herein.

In another illustrative embodiment, provided herein is a method for detecting circulating tumor nucleic acids in a sample of blood or a fraction thereof, from an individual, the method includes the following steps: a. analyzing the sample and one or more nucleic acid standard compositions provided herein to determine a ploidy state of a chromosomal segment in the individual by generating phased allelic data for a set of polymorphic loci on the chromosomal segment using nucleic acid sequence data, wherein the chromosomal segment is known to exhibit aneuploidy in cancer, wherein the nucleic acid sequence data is generated by performing high throughput DNA sequencing on a plurality of copies of a series of amplicons generated by a multiplex amplification reaction, and wherein each amplicon of the series of amplicons spans at least one polymorphic loci of the set of polymorphic loci; and b. determining the level of allelic imbalance present at the set of polymorphic loci based on the ploidy state determination. The detectable allelic imbalance in illustrative examples is indicative of the presence of circulating tumor nucleic acids in the sample.

In one embodiment, provided herein is a method for determining the genetic mutations in a solid tumor from an individual, the method includes the following steps:

A. determining whether an aneuploidy mutation is present by analyzing each of a sample of blood or a fraction thereof from the individual, and one or more nucleic acid standard compositions provided herein, to determine a level of allelic imbalance for each of a plurality of chromosomes or chromosome segments known to exhibit aneuploidy in cancer by:

i. generating nucleic acid sequence data for a set of polymorphic loci on each of the plurality of chromosomes or chromosome segments;

ii. using the nucleic acid sequence data to generate phased allelic data for the set of polymorphic loci on each of the plurality of chromosomes or chromosome segments, and iii. determining the level of allelic imbalance present for each of the plurality of chromosomes or chromosome segments using the phased allelic data, wherein a detectable allelic imbalance is indicative of an aneuploidy mutation in the solid tumor for each of the plurality of chromosomal segments.

In illustrative examples of the method embodiments above, the method is capable of detecting an average allelic imbalance equal to or greater than 0.45%. In illustrative examples of the method embodiments above, the one or more nucleic acid standard compositions comprise two or more nucleic acid standard compositions, each standard composition comprising a mixture of a first nucleosomal nucleic acid preparation generated in vitro from a cancer cell source or tumor fraction, and a second nucleosomal nucleic acid preparation generated in vitro from a matched non-cancer cell source, wherein the ratio of the quantity of the first nucleosomal nucleic acid preparation and the quantity of the second nucleosomal nucleic acid preparation in each nucleic acid standard composition of the set of nucleic acid compositions is different, wherein the first nucleosomal fraction comprises between 1% and 90% of the total nucleosomal nucleic acids in at least two of the two or more nucleic acid standard compositions, and wherein a copy number of a chromosomal region known to exhibit copy number variation in cancer, is different in the first nucleosomal nucleic acid preparation compared to the second nucleosomal nucleic acid preparation. In certain embodiments, the one or more nucleic acid standard compositions comprises one, two, three, four, five, six, seven, eight or more control samples made by spiking between 0.5% and 3.5% of DNA from a cell line having an aneuploidy of a control chromosomal segment known to be associated with cancer into a nucleic acid preparation from a matched cell line known to be disomic for the control chromosome or chromosomal segment.

In a further embodiment, the method further includes determining whether a single nucleotide variant is present in a plurality of single nucleotide variant loci known to be associated with cancer by performing high throughput DNA sequencing of the plurality of single nucleotide variance loci, from a sample of blood or a fraction thereof from the individual, wherein the presence of the single nucleotide variant in the sample for any of the plurality of single nucleotide loci is indicative of the presence of the single nucleotide variant in the solid tumor, thereby determining the genetic mutations in the solid tumor. In illustrative embodiments, the one or more nucleic acid standard compositions comprises an oligonucleotide comprising a single nucleotide variant known to be correlated with cancer. In illustrative embodiments, at least one of the one or more nucleic acid standard compositions further comprises a synthetic oligonucleotide between 50 and 500 base pairs in length comprising at least 50 contiguous nucleotides having a sequence that is at least 90% identical to a genomic sequence comprising or flanking a mutation correlated with cancer selected from a single nucleotide variant location, an indel location, or a gene fusion junction location.

In certain embodiments, nucleic acid sequence data can be generated by a variety of methods known in the art. In certain embodiments, the nucleic acid sequence data is generated using microarrays. In illustrative embodiments, the nucleic acid sequence data is generated by performing high-throughput DNA sequencing of the sample.

Some embodiments of the invention are kits comprising two or more nucleic acid standard compositions, each standard composition comprising a different mixture of a wild-type nucleosomal nucleic acid preparation generated in vitro from a wild-type cell source and a synthetic oligonucleotide between 50 and 500 base pairs in length comprising at least 50 contiguous nucleotides having a sequence that is at least 90% identical to a genomic sequence comprising or flanking a mutation correlated with cancer selected from a single nucleotide variant location, an indel location, or a gene fusion junction location, where the oligonucleotide is present in different concentrations in different standard compositions of the set at a concentration of between 0.01% and 20% of the concentration of nucleic acids from the wild-type nucleosomal nucleic acid preparation, and one or more primers for amplifying the one or more synthetic oligonucleotides.

In some embodiments, the kit comprises between 2 and 10 nucleic acid standard compositions. In another embodiment, the kit comprises between 2, 3, 4, 5, 6, 7, 8, 9, 10, 11, 12, 15, 20, 25 or 50 nucleic acid standard compositions on the low end and 3, 4, 5, 6, 7, 8, 9, 10, 11, 12, 15, 20, 25, 50, 100 or 250 nucleic acid standard compositions on the high end. In yet another embodiment, the kit comprises at least 3, 4, 5, 6, 7, 8, 9, 10, 11 or 12 nucleic acid standard compositions, wherein the kit comprises between 0.01% and 1% of the first nucleic acid preparation compared to the 2, 3, 4, 5, 6, 7, 8, 9, 10, 11 or 12 nucleic acid preparations. In another embodiment, the kit the comprises at least two nucleic acid standard compositions having between 0.01% and 1% of the first nucleic acid preparation compared to the second nucleic acid preparation, and where nucleic acids from the first nucleic acid preparation is between 0.01, 0.02, 0.03, 0.04, 0.05, 0.075, 0.1, 0.2, 0.3, 0.4, 0.5, 0.6, 0.7, 0.8, 0.9 or 1 on the low end and 0.02, 0.03, 0.04, 0.05, 0.075, 0.1, 0.2, 0.3, 0.4, 0.5, 0.6, 0.7, 0.8, 0.9, 1, 2, 3, 4, 5 or 10 on the high end as much as nucleic acids from the second nucleic acid preparation. In some embodiments, the first nucleic acid preparation in the kit is a nucleic acid preparation generated in vitro from a cancer cell source or tumor fraction. In some embodiments, the second nucleic acid preparation in the kit is a nucleic acid preparation generated in vitro from a matched non-cancer cell source.

In some embodiments, the kit comprises at least one nucleic acid standard composition comprising a synthetic oligonucleotide of between 50 and 500 base pairs, 75 and 400 base pairs, 100 and 350 base pairs, or 125 and 300 base pairs, in length having a sequence that is at least 90%, 91%, 92%, 93%, 94%, 95%, 96%, 97%, 98%, 99% or more identical to a genomic sequence comprising or flanking a mutation correlated with cancer selected from a single nucleotide variant location, an indel location, or a gene fusion junction location.

Kits for detecting circulating DNA according to some embodiments of the present invention, include standard compositions (and/or controls) for circulating DNA detection. For example, in certain embodiments, the standard compositions are sold and optionally shipped and packaged together with primers used to polymerize and/or amplify the standard compositions and/or to perform the amplification reactions discussed herein. In certain embodiments, controls include polynucleotides such as DNA, including isolated genomic DNA that exhibits one or more chromosomal aneuploidies such as CNV and/or includes one or more SNVs. In certain embodiments, the standard compositions (and/or controls) are called PlasmArt standards and include polynucleotides having sequence identity to regions of the genome known to exhibit CNV, especially in certain inherited diseases, and in certain disease states such as cancer, as well as a size distribution that reflects that of cfDNA fragments naturally found in plasma. Exemplary methods for making PlasmArt standards are provided in the examples herein. In general, genomic DNA from a source known to include a chromosomal aneuploidy is isolated, fragmented, purified, and size selected.

In certain embodiments, provided herein are artificial cfDNA polynucleotide standard compositions made by spiking isolated polynucleotide samples prepared as summarized in the examples, into DNA samples known not to exhibit a chromosomal aneuploidy and/or SNVs, at concentrations similar to those observed for cfDNA in vivo, such as between, for example, 0.01% and 20%, 0.1% and 15%, or 0.4% and 10% of DNA in that fluid. These standard compositions can be used as controls for assay design, characterization, development, and/or validation, and as quality control standards during testing, such as cancer testing performed in a CLIA lab and/or as standards included in research use only or diagnostic test kit.

The invention also includes methods of making the nucleic acid standard compositions. Embodiments of making the nucleic acid standard compositions include mixing a first nucleosomal nucleic acid preparation derived from a first cell source, and a second nucleosomal nucleic acid preparation from a second cell source, wherein the quantity of the first nucleic acid preparation is greater than (or in some embodiments, equal to) the quantity of the second nucleic acid preparation. In another embodiment, the invention includes methods of making the nucleic acid standard compositions include mixing a first nucleosomal nucleic acid preparation derived from a first cell source, and a second nucleosomal nucleic acid preparation from a second cell source, wherein the quantity of the first nucleic acid preparation is less than the quantity of the second nucleic acid preparation. In some embodiments, the nucleic acid standard compositions of the instant application can be used for diagnostic purposes or detection of a wide range of genetic disorders such as cancer or fetal chromosomal abnormalities. In some embodiments, the method of making includes mixing a first nucleosomal nucleic acid preparation generated in vitro from a cancer cell source, and a second nucleosomal nucleic acid preparation generated in vitro from a matched non-cancer cell source.

Cell Sources

The nucleosomal nucleic acid preparations used to create the subject prenatal or cancer nucleic acid proficiency testing standard compositions can be derived from a variety of cell types. Suitable cell types can be primary cells obtained directly from a human subject or can be cell lines that can be propagated in in vitro cell culture. A wide variety of primary cells can be used.

Typically primary cells from an easily removable tissue or fluid source are used, e.g. blood or a cellular blood fraction such as a buffy coat layer. Similarly, a wide variety of cell lines may be used. Examples of such cell lines include cell lines obtained from the Cornell Institute or the American Type Culture Collection (ATTC).

In some embodiments, the cell sources are from a genetically related individuals. Examples of such genetically related individuals are (1) mother and child, (2) mother and multiple children, and (3) mother, father and child. In other embodiments the cell sources are from genetically unrelated individuals. In some embodiments the primary cells are from genetically related individuals. In other embodiments, the cell lines are obtained from genetically related individuals. In some embodiments, the cell sources are from cells from the same tissue type, wherein one of the cell types is a cancer cell line and the other cell source is a cell line from the same tissue, but not a cancerous cell line. In some embodiments, the cell sources are from cells from the same tissue type, wherein one of the cell types is a cancer cell line and the other cell source is an in vitro non-cancerous matched cell line.

In some embodiments the first cell source may be primary cells from a first human subject and the second cell source may be primary cells from a different human subject. In some embodiments, the first cell source and the second cell source may be obtained from the same cell lines propagated in in vitro cell culture. In some embodiments, the first cell source is a primary cell line derived from a first tissue and the second cell source is a primary cell line derived from a second tissue. In some embodiments the first cell source is a primary cell line and additional control nucleic acids included in the standard compositions comprise one or more synthetic oligonucleotides. In some embodiments the one or more synthetic oligonucleotides include one or more single nucleotide variations. In some embodiments the one or more synthetic oligonucleotides are between 50 and 500 base pairs in length. In some embodiments, the one or more synthetic oligonucleotides are between 50 and 500 base pairs in length and include at least 25 contiguous nucleotides having a sequence that is at least 90% identical to a genomic sequence comprising or flanking a mutation correlated with a single nucleotide variation (SNV). In some embodiments, the one or more synthetic oligonucleotides are between 50 and 500 base pairs in length and include at least 25 contiguous nucleotides having a sequence that is at least 95% identical to a genomic sequence comprising or flanking a mutation correlated with a single nucleotide variation. In some embodiments, the one or more synthetic oligonucleotides are between 50 and 500 base pairs in length and include at least 100 contiguous nucleotides having a sequence that is at least 90% identical to a genomic sequence comprising or flanking a mutation correlated with a single nucleotide variation. In some embodiments, the one or more synthetic oligonucleotides are between 50 and 500 base pairs in length and include at least 100 contiguous nucleotides having a sequence that is at least 95% identical to a genomic sequence comprising or flanking a mutation correlated with a single nucleotide variation (SNV). In some embodiments, the one or more synthetic oligonucleotides are between 100 and 400 base pairs in length and include at least 25 contiguous nucleotides having a sequence that is at least 98% identical to a genomic sequence comprising or flanking a mutation correlated with a single nucleotide variation (SNV), an indel location, or a gene fusion junction location. In some embodiments, the one or more synthetic oligonucleotides are between 100 and 400 base pairs in length and include at least 50 contiguous nucleotides having a sequence that is at least 95% identical to a genomic sequence comprising or flanking a mutation correlated with a single nucleotide variation (SNV), an indel location, or a gene fusion junction location. In some embodiments, the one or more synthetic oligonucleotides are between 50 and 500 base pairs in length and include at least 50 contiguous nucleotides having a sequence that is at least 90% identical to a genomic sequence comprising or flanking a mutation correlated with a single nucleotide variation (SNV), an indel location, or a gene fusion junction location.

In some embodiments the first cell line and the second cell line may be from the same cell line. In some embodiments the first cell line and the second cell line are from different cell lines. In some embodiments the first cell line is a cancerous cell line and the second cell line is a non-cancerous cell line. In some embodiments the first cell line is a cancerous cell line and the second cell line is an in vitro matched non-cancer cell line. In some embodiments the first cell line is a cell line having a copy number variation and the second cell line is a cell line having one or more single nucleotide variations or indels. In some embodiments the first cell source may be from a primary cell line and the second cell source may be from a second cell line having one or more single nucleotide variations (SNV). In some embodiments the primary cell line may include a copy number variation and the second cell line may include one or more single nucleotide variations (SNVs).

Nucleic Acid Isolation

The nucleic acids may be isolated from the cell sources by a variety of methods well known to the person of ordinary skill in molecular biology. Typically such methods will involve lysing the cell, thereby liberating nucleic acids so as to leave chromatin structure sufficiently intact to allow the preparation nucleosomal ladders, i.e., nucleosomal preparations. Suitable cell lysis methods include methods in which the nucleus is separately released for subsequent isolation and methods in which the nuclear membrane is dissolved. In some embodiments, the cells may be permeabilized, e.g, using a detergent such as lysolecithin, so as to retain chromatin structure. In some embodiments, the cell membrane may be disrupted by inducing apoptosis in the cells of the cell source.

It is of interest to prepare nucleic acids that are of free of other cellular components so as to enable the biochemical manipulation of the nucleosomal ladders for use in subsequent procedures, e.g., DNA sequencing. In an embodiment of the invention, the commercially available nucleic acid system called AMPURE™ can be used to both purify DNA and isolate nucleosomal fractions of the desired size.

Nucleosomal Ladders

In human cells (as well as other eukaryotic cells) nuclear DNA is organized in the chromatin in nucleosome's in which the chromosomal DNA is organized in approximately 147 base pair units of DNA wrapping around a histone core. The DNA is close proximity to the histone core is relatively resistant to cleavage as compared to the DNA that is present between the nucleosomes. The nucleosomes form a regular pattern in the chromatin, such that exposure of the nucleosomal structures in chromatin to an endonuclease, e.g., micrococcal endonuclease results in a reproducible pattern of a DNA fragments of approximately defined length. This pattern can be visualized by separating the nucleic acid digest fragment based on length, e.g., by electrophoresis. The histone component of the nucleosome serves to protect the DNA wrapped around the histone core from endonuclease digestion. Fragmenting genomic DNA with a nuclease or fragmenting with a non-enzymatic method (e.g., a chemical digestion with a hydroxyl radical-based reaction, electromagnetic radiation, or sonication) are well known to persons of ordinary skill in the art. Subjecting the chromatin to a digestion reaction results in the formation of a set of nucleic acid fragments approximately 147 base pairs in length and multiples thereof, for the sake of convenience such a set of fragments can be can be referred to as a nucleosomal ladder. A nucleosomal ladder would, for example, appear as a series of bands of different molecular weight when separated by gel electrophoresis. The nucleosomal ladder comprises the approximately 147 base pair fragment and the multiples thereof obtained by digesting the chromatin. The 147 base pair fragment is referred to as the monosomal fraction of the nuclear ladder. The two-fold multiple of the monosomal fraction is referred to as the disomal fraction and is formed by nucleases (or other DNA cleavage agents) cleaving DNA adjacent to two nucleosomes (but leaving the internucleosomal region intact). The three-fold multiple of the monosomal fraction is referred to as the trisomal fraction and is formed by nucleases (or other DNA cleavage agents) cleaving DNA adjacent to three nucleosomes (but leaving the internucleosomal regions intact). It will be understood by person skilled in the art of molecular biology that nuclease cleavage (or other DNA cleavage agents) is imprecise and can give rise a set of nucleic acid fragments of similar, but not identical size.

In some embodiments of the invention the nucleosomal ladders may be produced by inducing apoptosis in cells. As a part of apoptosis process, endogenous endonucleases cleave the DNA component of the chromatin so as to form nucleosomal ladders. In some embodiments of the invention the nucleosomal ladders may be produced by digesting the chromatin with an endonuclease, e.g., micrococcal endonuclease. In other embodiments of the invention the nucleosomal ladder may be produced by exposing the chromatin to digestion with nonenzymatic agents. AMPURE™ can be used to both purify DNA and isolate nucleosomal fractions of the desired size. In other embodiments, nucleosomal fractions of the desired size can be obtained by gel electrophoresis separated fragment purification, purification from HPLC, or purification through ultracentrifugation.

Manipulation of Nucleosomal Fractions

In some embodiments, the nucleosomal fractions, monosomal, disomal, trisomal, and various combinations thereof may be manipulated so as simulate one or more genetic abnormalities, such as a duplication, deletion, or point mutation. For example, a deletion may be simulated by exposing nucleosomal preparations to a solid support comprising nucleic acids (or analogs thereof) to selectively bind to the region to be deleted, thereby producing a preparation containing a greatly reduced amount of the region to be deleted. Similarly, point mutations may be introduced by techniques such as PCR performed on the nucleosomal fractions.

Analysis of Cell Free Fetal DNA in the Maternal Blood Stream

The subject compositions for prenatal nucleic acid proficiency testing can be used in a wide variety of prenatal genetic testing methods. The proficiency testing standards are used essentially the same as a sample obtained from a test subject, thereby providing a meaningful standard from the specific test being evaluated. Such methods of noninvasive prenatal genetic testing typically involve the analysis of cell free nucleic acids found in the bloodstream of a pregnant woman. In some embodiments, the prenatal genetic testing method involves nondirected sequencing of the cell free nucleic acids such as in U.S. Pat. Nos. 8,296,076 B2, 8,008,018 B2, 7,888,017 B2, and 8,467,976 B2. In other embodiments, the directed analysis of specific polymorphic regions or specific non-polymorphic regions, such as in patent applications US 2013/0143213, A1, US 2013/0172211 A1, US 2012/0270212 A1, US 2012/0122701 A1, US 2013/0123120 A1, and US 2011/0178719 A1, can be employed.

Analysis of Cell Free DNA for Cancer Cell Derived DNA

Various protocols are known to the person or ordinary skill in the art for analyzing cell free DNA circulating in the blood stream or other tissue, but ultimately derived from cancerous cells, for example, see publications such as: Circulating Cell-Free DNA in Plasma/Serum of Lung Cancer Patients as a Potential Screening and Prognostic Tool, Pathak et al, Clinical Chemistry October 2006 vol. 52 no. 10 1833-1842; Cell-free Tumor DNA in Blood Plasma As a Marker for Circulating Tumor Cells in Prostate Cancer, Schwarzenbach et al, Clin Cancer Res Feb. 1, 2009 15; 1032; Cell-free DNA: measurement in various carcinomas and establishment of normal reference range, Wua et al, Clinica Chimica Acta, Volume 321, Issues 1-2, July 2002, Pages 77-87; Detection of Circulating Tumour DNA in the Blood (Plasma/Serum) of Cancer Patients, Anker et al, Cancer and Metastasis Reviews 1999, Volume 18, Issue 1, pp 65-73; Cell-free nucleic acids as biomarkers in cancer patients, Schwarzenbach et al, Nature Reviews Cancer 11, 426-437 (June 2011); Circulating Tumor-Specific DNA: A Marker for Monitoring Efficacy of Adjuvant Therapy in Cancer Patients, Fiegl et al, Cancer Res Feb. 15, 2005 65; 1141.

The following examples are offered for purposes of illustration only and should not be construed as limiting the claimed inventions.

EXAMPLES

Example 1

Developing Synthetic Pregnancy Plasma Samples for Use in Non-Invasive Prenatal Testing Introduction: Cell-free DNA (cfDNA)-based non-invasive prenatal testing (NIPT) allows for the identification of fetal aneuploidies from the mixture of maternal and fetal cfDNA (cell free DNA) in maternal circulation using next-generation sequencing-based approaches. Such tests are revolutionizing prenatal screening and fetal aneuploidy detection. However, cfDNA is a mixture of maternal and fetal cfDNA, and both the overall amount of cfDNA as well as the fraction of cfDNA from the fetus can be limiting. This limits the number of analyses that can be performed on a single sample (e.g. for development and proficiency testing). Additionally, validating NIPT performance on rare disorders is challenging as patient recruitment is limiting. To overcome these challenges, a novel method for creating an artificial pregnancy plasma DNA (PlasmArt) was invented.

Methods: DNA was isolated from primary cells or cultured immortalized cells and treated to generate nucleosomal-size ladders (mono-, di-, and tri-nucleosome-size fragments). These ladders mimicked observed cfDNA fragment lengths, which are derived from genomic DNA digested by apoptotically-activated nucleases. This includes shorter "fetal" fragments and a combination of shorter and longer "maternal" fragments. To simulate pregnancy plasma, the maternal and child "cfDNAs" were mixed at various ratios to mimic a range of fetal fractions. These mixtures were then examined using the Natera PANORAMA™ NIPT, which employs the advanced "Next-generation Aneuploidy Test Using SNPs" (NATUS) algorithm. The NATUS algorithm reports copy number for each chromosome with an associated confidence.

Results: This approach allowed for the identification of the fetal fraction influence on test accuracy on the same mother-child pair, rather than comparing accuracy over fetal fractions encountered from distinct pregnancies in the population. The performance of the Natera PANORAMA™ NIPT was examined on mixtures of maternal and child samples. NIPT correctly distinguished affected and unaffected "pregnancy", suggesting that these fetal fraction mixtures behave similarly to cfDNA isolated from maternal plasma. The ability to call chromosome copy number with high confidence at fetal fractions of below 5% correlated well with "true" pregnancy plasma samples.

Example 2

Cell Free DNA Testing Standards for Genetic Disorders

Non-invasive Prenatal Screening (NIPS) to conditions that are rare and not routinely screened for in pregnancy is challenging. The collection of sufficient samples to confidently validate test performance is essentially impossible. Further, the samples that are collected are almost always identified after an invasive procedure and therefore of later gestational age and higher fetal fraction. As fetal fraction is a crucial parameter affecting performance of all NIPS, using exclusively higher fetal fraction samples may result in inflated claims of test sensitivity. Therefore, an alternative approach to validating NIPS for rare disorders is needed to adequately estimate test performance. A method to generate artificial cfDNA samples (PlasmArt) that mimic the size distribution of natural cfDNA, i.e., cell-free DNA diagnostic testing standards was developed. PlasmArt can be generated from lymphoblastoid cell lines or white blood cells (i.e. buffy coat) of normal or affected individuals. Once prepared, PlasmArt from two individuals, such as a mother and her child, can be combined to simulate pregnancy cfDNA at any desired fetal fraction ratio, enabling simulation of the fetal fractions observed in real populations. To generate artificial samples that mimic natural cfDNA, we sought to replicate the mechanism of cfDNA fragmentation in vitro. An individual's cfDNA predominately arises from apoptosis of cells in the hematopoietic system (Lui Y Y, Chik K W, Chiu R W, Ho C Y, Lam C W, Lo Y M. Clin Chem. 2002; 48:421-7). During apoptosis, the Caspase-Activated DNase (CAD) is activated by Caspase-3 cleavage of the CAD inhibitor. The activated nuclease preferentially cleaves DNA between nucleosomes (Widlak P. Acta Biochim Pol. 2000; 47:1037-44), resulting in the characteristic mono-, di-, and trinucleosomal-sized DNA fragments observed in cfDNA (Li Y, Zimmermann B, Rusterholz C, Kang A, Holzgreve W, Hahn S. Clin Chem. 2004; 50:1002-11; Fan H C, Blumenfeld Y J, Chitkara U, Hudgins L, Quake S R. Clin Chem. 2010; 56:1279-86.). Each nucleosome coordinates approximately 146 nucleotides of DNA (Luger K, Mäder A W, Richmond R K, Sargent D F, Richmond T J. Nature. 1997; 389:251-60.). Based on the intranucleosomal nuclease activity that generates cfDNA, we used micrococcal nuclease (MNase), which has a similar biochemical activity of cleaving preferentially between nucleosomes (Widlak P, Li P, Wang X, Garrard W T., J Biol Chem. 2000; 275:8226-32; Allan J, Fraser R M, Owen-Hughes T, Keszenman-Pereyra D. J Mol Biol. 2012; 417:152-64.). Previous methods to generate artificial cfDNA from pregnancy samples have relied on sonicated DNA (Srinivasan A, Bianchi D W, Huang H, Sehnert A J, Rava R P. Am J Hum Genet. 2013; 92:167-76). However sonication results in broad fragment size distributions (peak size 200 nucleotides+/−100) (See http://www.diagenode.com/en/applications/dna-Shearing.php for a description of sonication sizes and distributions), and start sites are not constrained by nucleosome position. By employing an enzyme with a similar biochemical activity to the in vivo nuclease involved in fragmentation, the cell-free DNA diagnostic testing standards, e.g., the PlasmArt preparation method described herein, approximates the size and cleavage biases observed in natural cfDNA.

Results: In vitro recapitulation of the fragmentation profile observed in cell free DNA Artificial samples should approximate the size distribution of cfDNA observed in vivo to capture potential biases introduced during library construction. Library preparation PCR typically favors short fragments over long, thus post amplification only short fragments will be represented. We first confirmed the nucleosomal ladder pattern observed in natural cfDNA from samples purified in the Natera clinical laboratory. To overcome the low concentration of natural cfDNA, the cfDNA from 96 pregnant individuals was mixed in equal volumes, concentrated approximately 50 fold, and examined on a BIOANALYZER™ electrophoresis system (FIG. 1A). The mononucleosomal peak is present at 180 nucleotides. A dinucleosomal peak is present at 382 nucleotides. PlasmArt was prepared from cell lines (FIG. 1B) and white blood cells (FIG. 1C). PlasmArt from cell lines displays a mononucleosomal peak at 148 nucleotides and the dinucleosomal peak at 349 nucleotides. For white blood cells, the mononucleosomal peak is at 146 nucleotides and the dinucleosomal peak is at 359 nucleotides. Thus the method for creating PlasmArt results in a DNA fragment profile similar to natural cfDNA. The location of the peaks suggest that natural cfDNA are larger than artificial cfDNA fragments, but this is consistent with the observation that CAD releases larger fragments than MNase, likely due to a higher activity of MNase in vitro. Overall, PlasmArt is more similar than other methods used to create artificial cfDNA, and we hypothesize that size difference has a minimal effect. In fact, the small fragments produce a more challenging sample type for PCR assay methods that require that target SNPs be flanked by two intact primer binding sites, a less likely occurrence as DNA fragments become smaller.

Figure 1B:
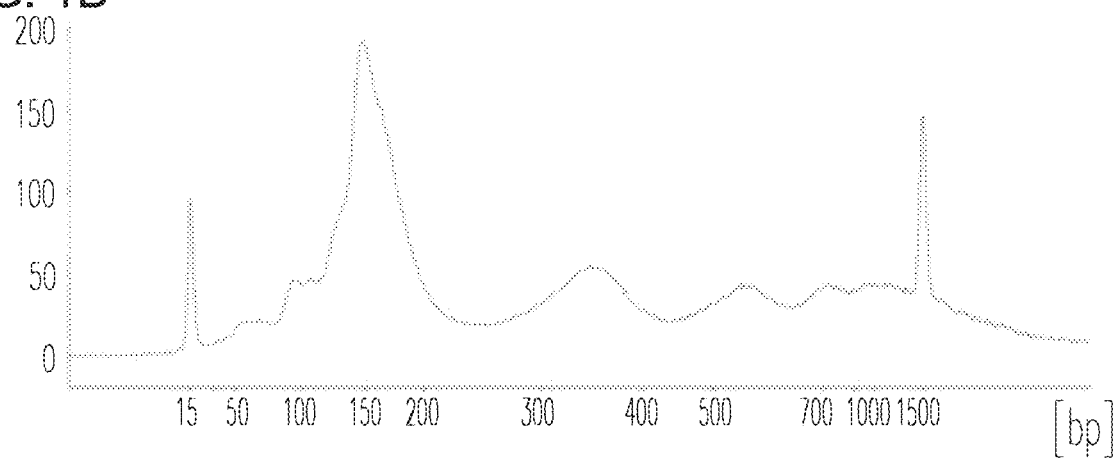
Figure 1C:
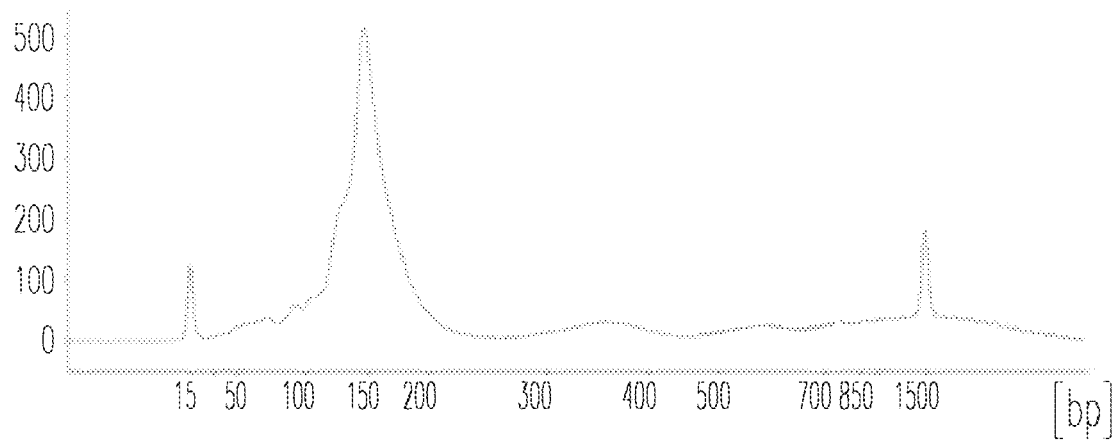

FIGS. 1A-1C shows size distributions of natural and artificial cfDNA (cell free). FIG. 1A shows mixtures of 96 patient-derived cfDNAs, concentrated 50 fold. FIG. 1B shows cell line-derived artificial cfDNA. FIG. 1C shows white blood cell-derived artificial cfDNA.

Mixtures of Mononucleosomal Mother and Child Simulate Real Samples:

In addition to mimicking the size distribution of natural cfDNA, mixtures of mother and child PlasmArt samples must have similar NIPS performance to pregnancy cfDNA samples. PlasmArt was generated from cell lines purchased from the Coriell Cell Repository: GM11388 (child) and GM11389 (mother). Four independent mixtures of mother and child were made such that the molar ratios were 3%, 6%, 9%, and 12% child. These samples were used as input into the PANORAMA™ NIPS. The fetal fraction calculated by the algorithm for these samples were 3.5%, 6.3%, 9.1%, and 12.0%, respectively (FIG. 2, R2=0.99, slope=0.94), indicating a near perfect correlation between input child amount and measured fetal fraction in PANORAMA™.

Figure 2:
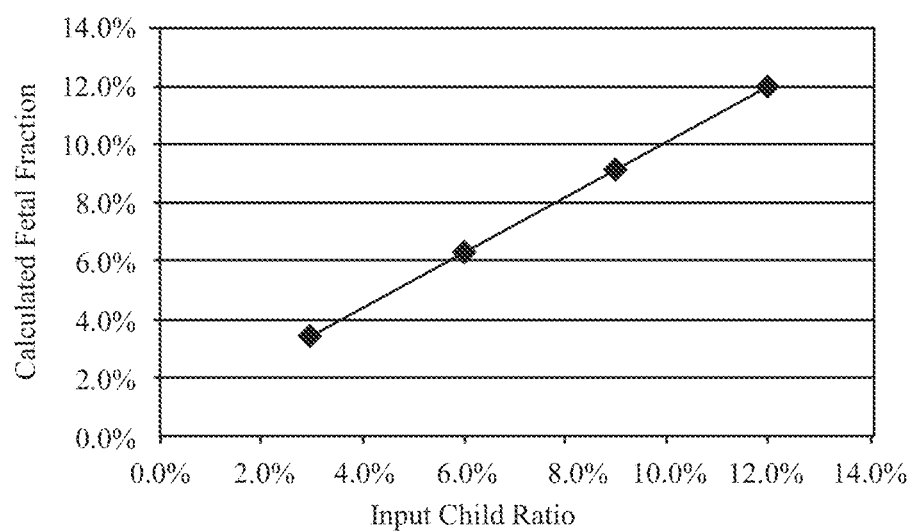
FIG. 2 shows calculated fetal fractions as a function of input child amount.

FIG. 2. Calculated Fetal Fractions as a function of input child amount. Four independent mixtures were generated from one mother/child pair, tested in the PANORAMA™ workflow, and examined for the calculated fetal fraction. The R2=0.99 and the slope=0.94.

Figure 3:
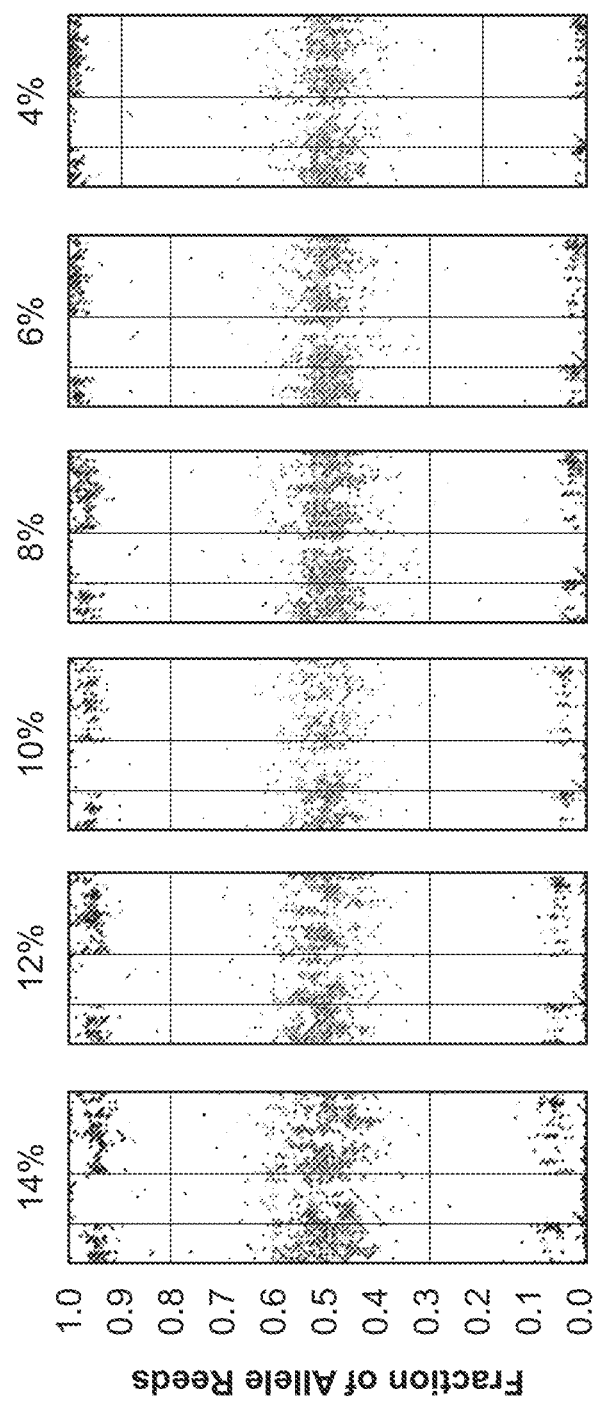
FIG. 3 shows a plot of the allele ratios of the SNPS analyzed at different fetal fraction concentrations.
Figure 5A:
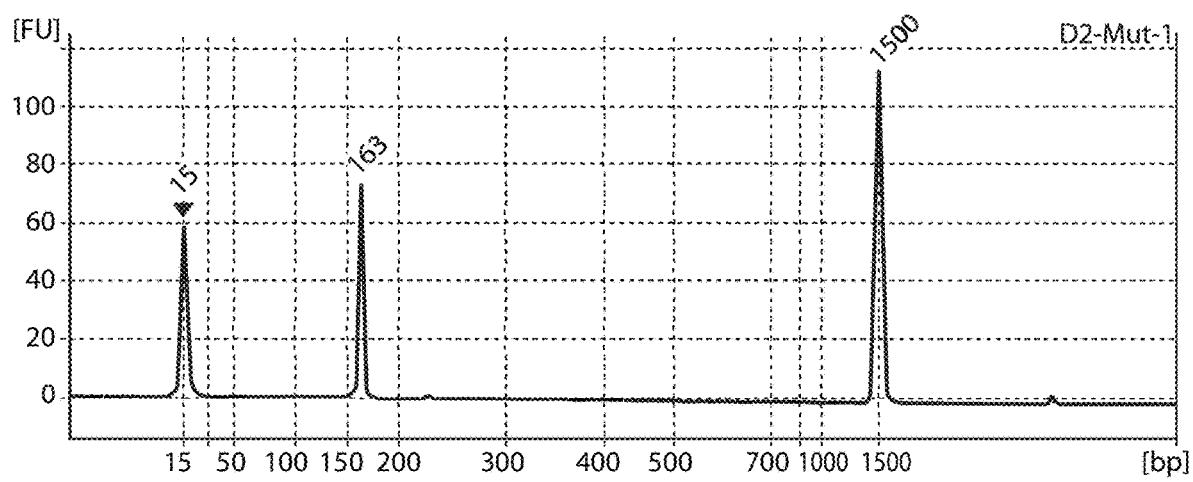
FIGS. 5A-5M provide graphs showing size distribution of synthetic spike PCR DNA products after PCR amplification, confirming the production of 160 base pair fragments in all cases.
Figure 5B:
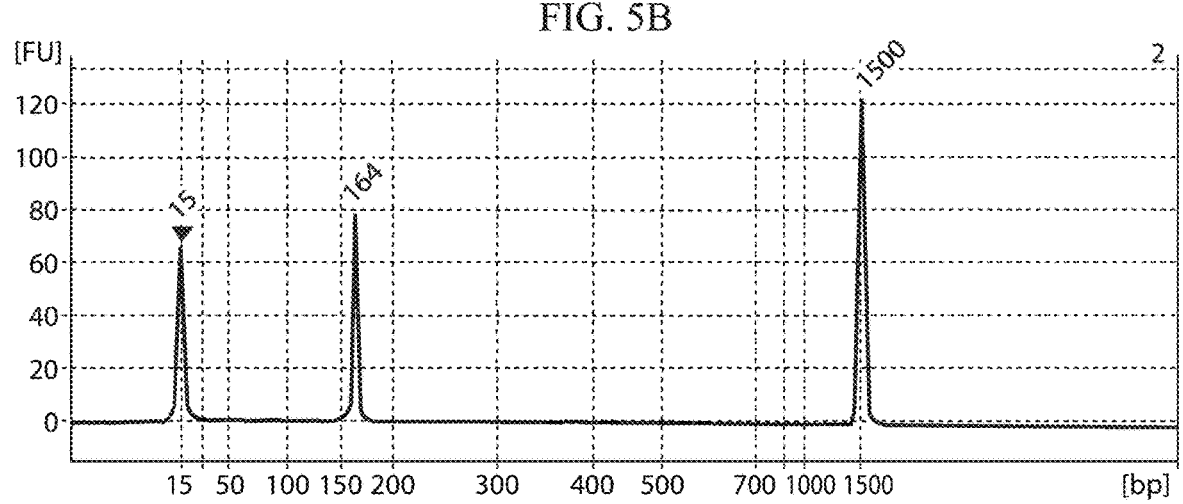
Figure 5C:
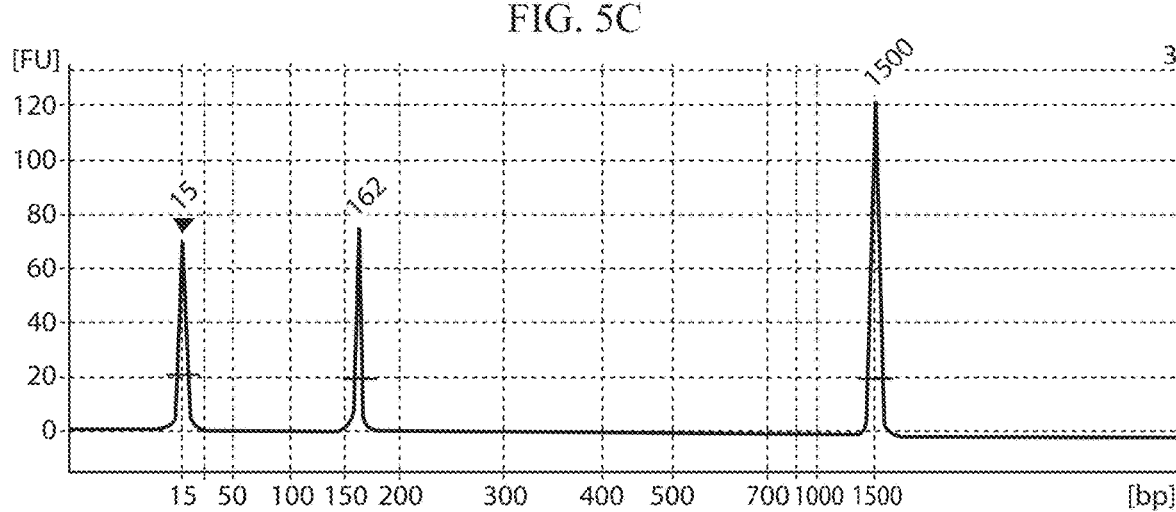
Figure 5D:
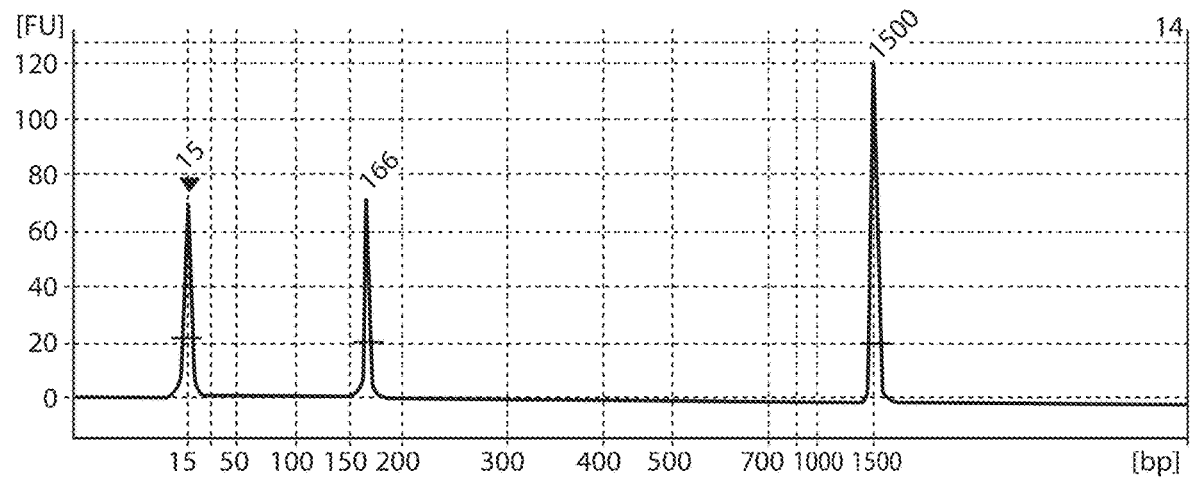
Figure 5E:
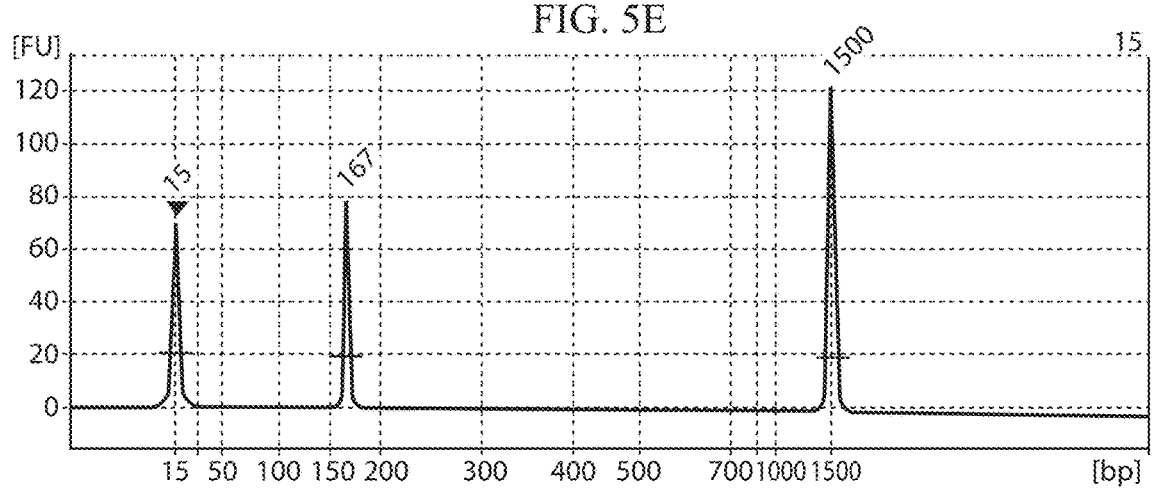
Figure 5F:
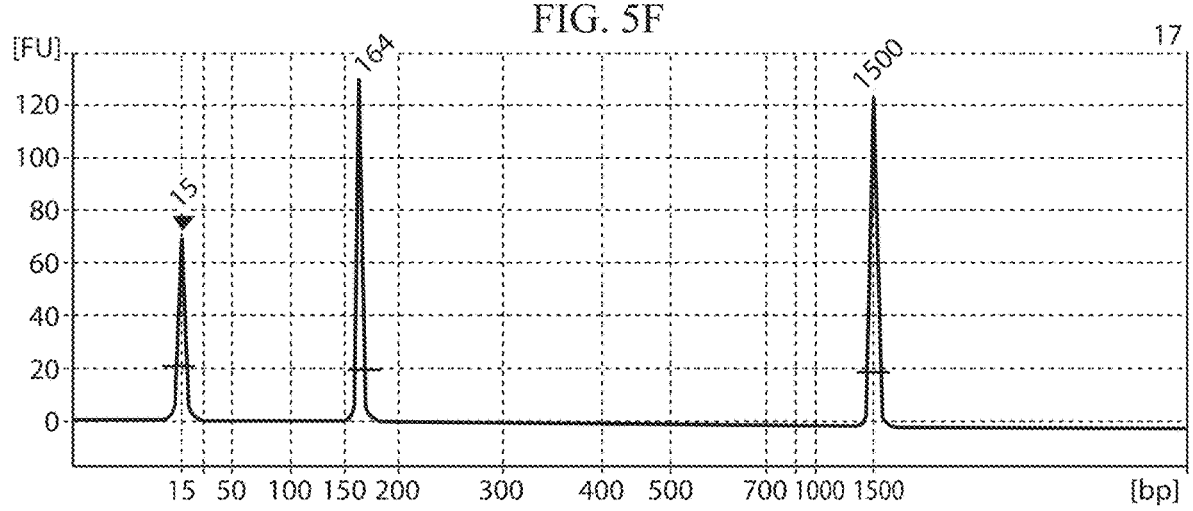
Figure 5G:
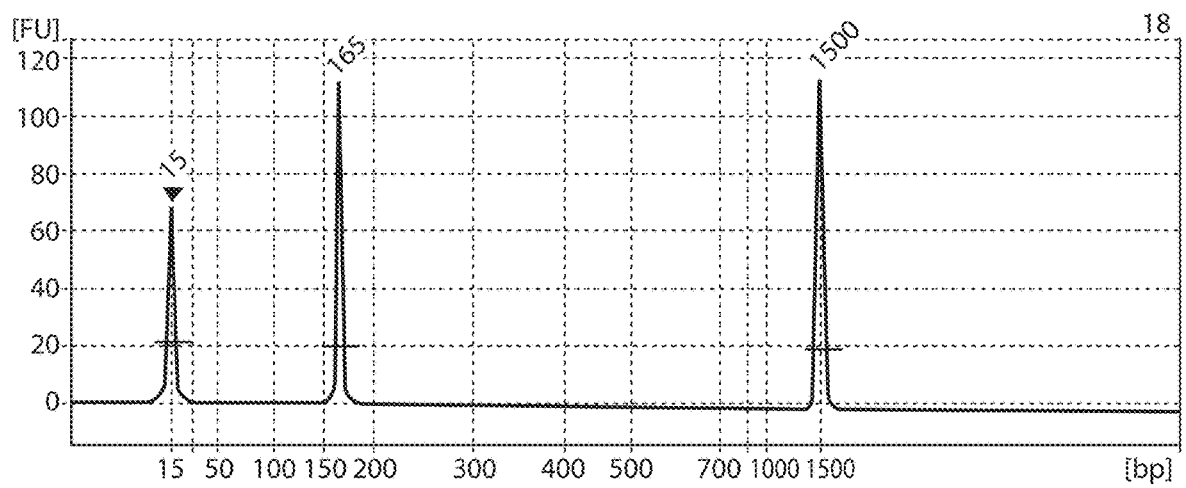
Figure 5H:
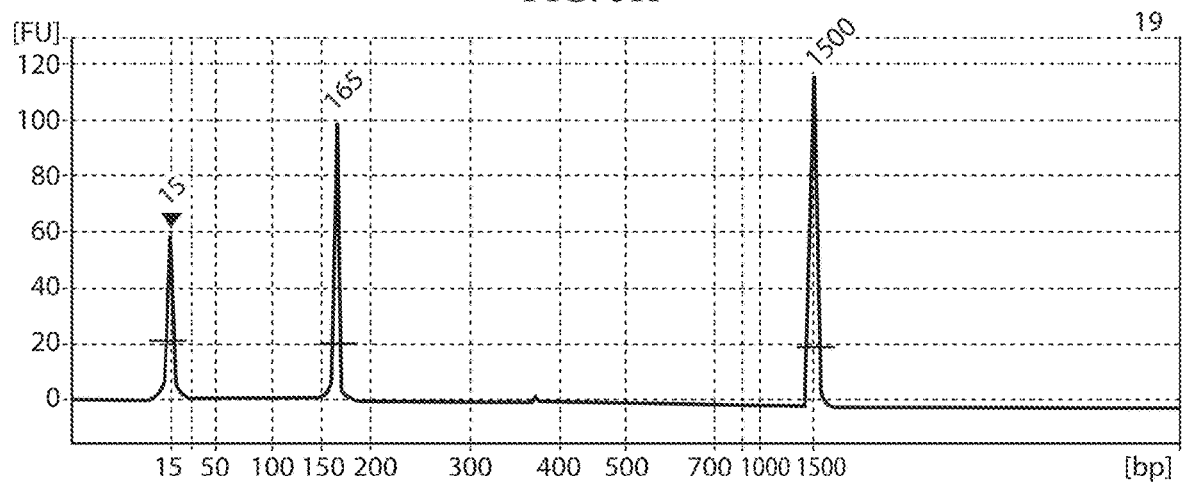
Figure 5I:
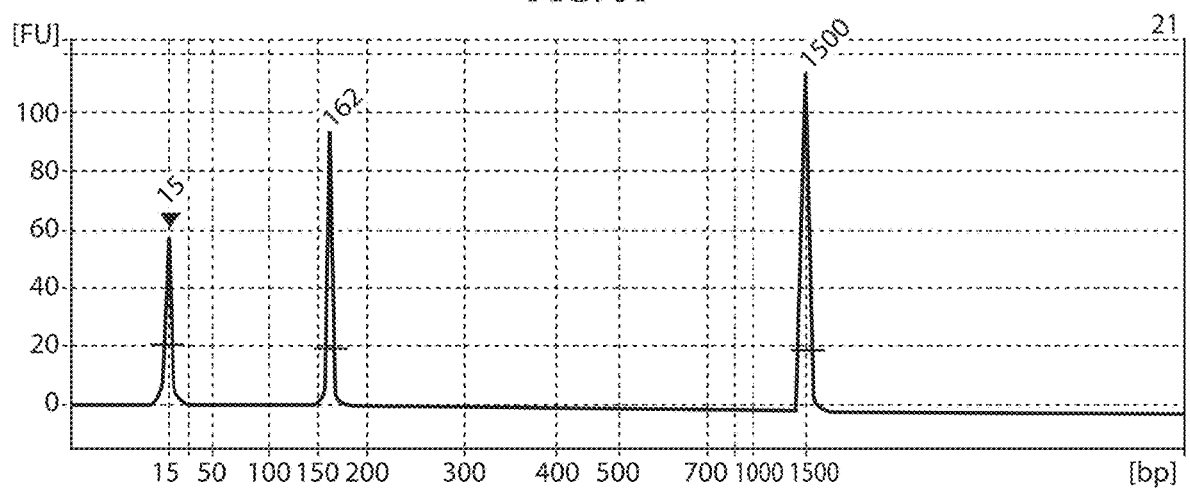
Figure 5J:
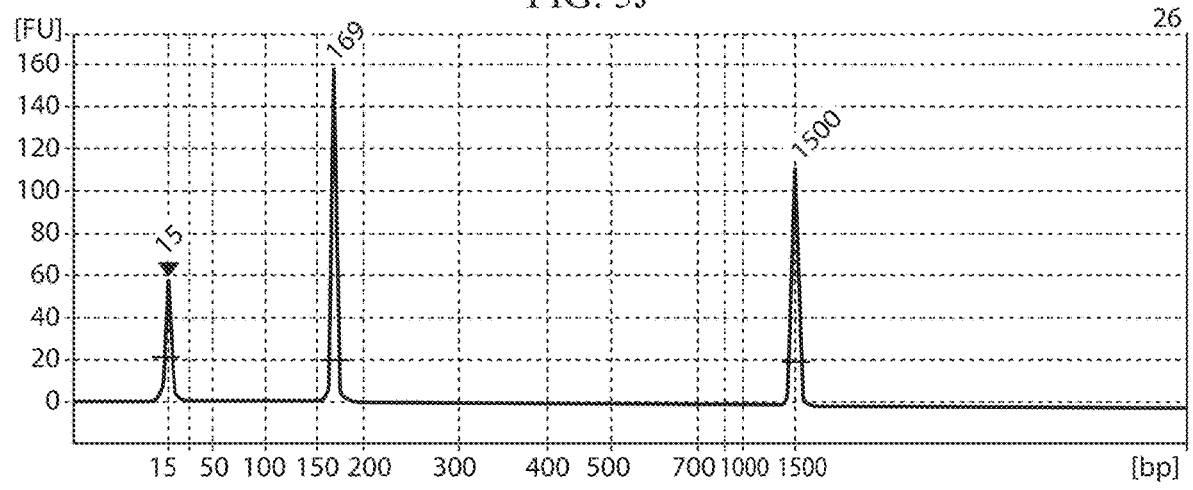
Figure 5K:
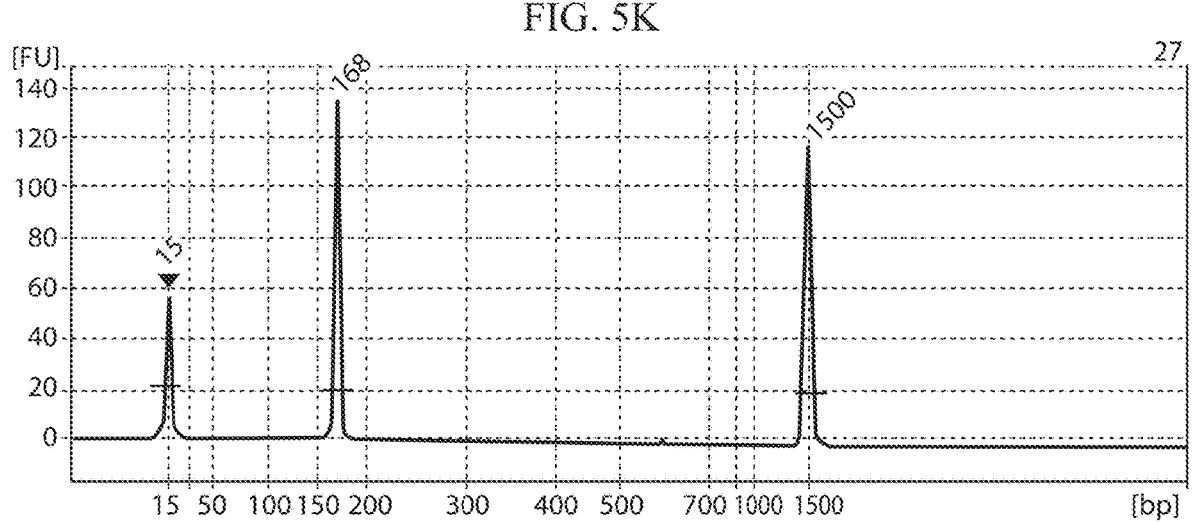
Figure 5L:
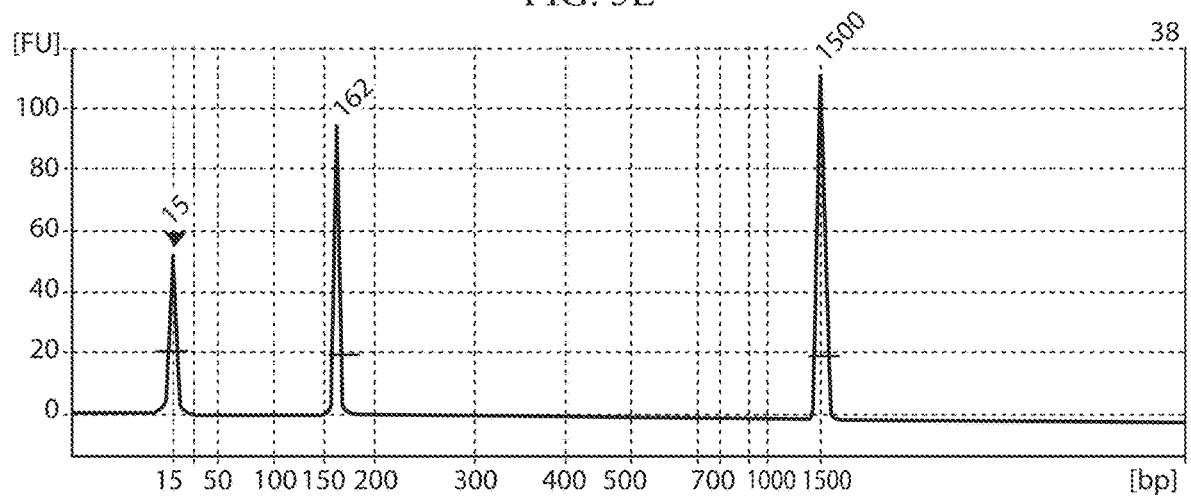
Figure 5M:
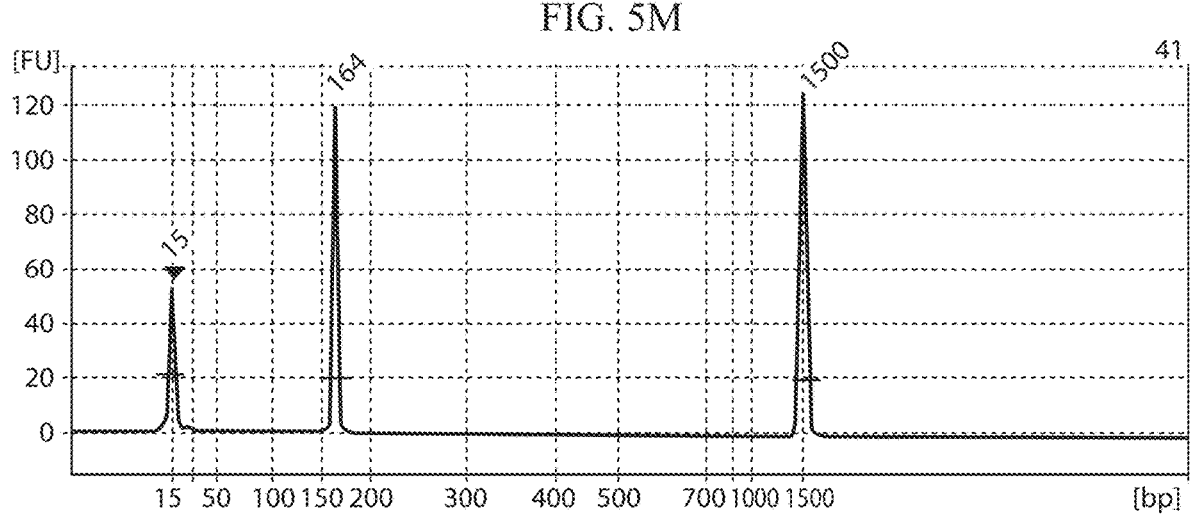

Having demonstrated the ability to make predictable mixtures of mother and child, we examined the ability to detect a paternally contributed 22q11.2 microdeletion. If a microdeletion originates in the father, the lack of paternally contributed SNPs can be visualized on allele frequency plots (FIG. 3). In this case, there are no paternally contributed SNPs in the $22_g11.2$ region, while there are paternally contributed SNPs in other genomic regions. This $22_g11.2$ deletion can be observed from low fetal fraction (4%) to a relatively high fetal fraction (14%), and all intermediate fetal fractions. Taken together, these data show that child DNA can be mixed into mother DNA in predictable amounts, and mixtures can be analyzed to identify known microdeletion syndromes.

FIG. 3. Paternal 22q11.2 deletions can be detected over a range of fetal fractions. At each fetal fraction, 3 different genomic regions are shown adjacent to one another—17p11.2, 22q11.2, and 22q13. "A" allele ratios from individual binary SNPs ["A" allele reads/("A"+"B" reads)] are shown in ascending order on the X-axis by genomic region, then by SNP chromosome location. In pregnancy cfDNA and PlasmArt, the father's contribution to the mixture can be most readily observed as points offset from the 0% or 100% A allele fractions (maternal BB and AA points, respectively). These are SNPs for which the mother is homozygous AA or BB, but has the fetus or mixed in child sample contributes only an A or B allele respectively. For instance, at 10% fetal fraction, the mixed in child sample's contribution can be visualized as points centered at 5% and 95%, since one half of the sample mixed in at 10% corresponds to the A or B allele respectively. The absence of any contribution from the paternal SNPs observed at all fetal fractions for the 22q11.2 region is consistent with a paternally contributed microdeletion of this region. This titration demonstrates the ability to detect a paternally contributed microdeletion over a wide range of fetal fractions, down to 4%.

We next examined the ability to detect maternally contributed microdeletions. Fifteen PlasmArt samples were made over a broad range of fetal fractions from a Coriell Cell Repository Angelman Syndrome family: GM11517 (mother) and GM11516 (child). Angelman Syndrome is caused by a maternally contributed deletion of 15q11.2-q13. The calculated fetal fractions were 6.8%, 7.8%, 8.4%, 10.0%, 10.8%, 11.8%, 13.0%, 14.4%, 14.6%, 15.2%, 16.7%, 18.6%, 20.4%, 21.3%, and 24.6%. Unlike paternal deletions, maternally inherited deletions result in subtler changes to the allele ratios and are difficult to detect visually on Allele Ratio Plots. Thus, the Natera PANORAMA™ NATUS algorithm, modified to detection segmental deletions was employed to examine maternal deletions. The algorithm correctly identified the deletion in all 15 of the PlasmArt samples. Importantly, in these samples the algorithm also evaluated copy number of the 22q11.2, Cri-du-chat, and 1p36 regions. The algorithm correctly identified 44 of 45 regions (3 regions by 15 samples) as normal, no deletion detected. The algorithm did not return a high confidence result for the 22q11.2 region of the 6.8% sample. The observed sensitivity and specificity of these initial tests indicate that PlasmArt can be used for developing and validating NIPS for rare syndromes Conclusion It was demonstrated that the cell-free DNA standard prepared using MNase in vitro more faithfully recapitulates the size distribution of natural cfDNA than sonication. MNase treatment of either cell lines or white blood cells gave similar results that were comparable to natural cfDNA size distributions. Next, we showed that mixtures of various amounts of mother and child PlasmArt samples correlated very well with the fetal fractions measured by the Natera PANORAMA™ NATUS algorithm. Finally, we demonstrated that PlasmArt mixtures could be used to simulate pregnancy cfDNA samples at various fetal fractions having a paternally-inherited 22q11.2 deletion and a maternally-inherited Angelman deletion. For each of these simulated groups, the Natera PANORAMA™ NATUS algorithm correctly identified the deletions and the unaffected regions. These results suggest that PlasmArt can be used as a tool for validating rare disorders in the context of NIPS.

Example 3

Tumor Standards for Copy Number Variants (CNV) Samples

Assay validation was performed using five human breast cancer cell lines (HCC38, HCC1143, HCC1395, HCC1954, and HCC2218) along with matched normal cell lines; these cell lines and matched genomic DNA (gDNA) samples were obtained from American Type Culture Collection (ATCC). Paired father and child cell lines (GM10383 and GM10382 respectively) for producing cell-free nucleic acid standards (details below) were obtained from the Coriell Cell Repository (Camden, N.J.). The child of this cell line is a DiGeorge Syndrome (DGS) proband with a maternal deletion and thus the child cell line has only the paternal DGS 22q11 region; the parental origin of the deletion was determined by our SNP-based mmPCR assay (data not shown). Tumor tissues from 14 breast cancer patients were obtained from Geneticist (Glendale, Calif.) and North Shore-LIJ (Manhasset, N.Y. In addition, matched buffy coat (4 patients) and matched plasma samples (9 patients) were obtained. Blood from each subject was collected into EDTA tubes, and cfDNA was isolated from 1 ml plasma using the QIAAMP™ Circulating Nucleic Acid Kit (catalog no. 55114, Qiagen, Valencia, Calif.) according to the manufacturer's instructions.

Cell Culture

All cell culture reagents (culture media and fetal bovine serum [FBS]) were obtained from Life Technologies (Foster City, Calif.). ATCC cell lines were cultured according to the ATCC cell culturing, passaging, and cryogenic storage guidelines. Cells were cultured in 10% FBS RPMI 1640 (high glucose with pyruvate) with 2 mM L-Glutamine at 37° C. with 5% CO2. Seed stocks were made of each cell line after one passage, and a cut off of five passages was chosen in order to preserve the genetic stability of each cell line. Cells from the Coriell Cell Repository were grown according to manufacturer's instructions: GM10382 in 15% FBS DMEM and GM10383 in 15% FBS RPMI 1640. Cells were washed twice in DPBS to remove FBS and culture media before DNA isolation.

Single cells were isolated from cultures manually using an inverted phase-contrast microscope. A serial-dilution method was implemented involving pipet transfers of single media droplets containing cells in suspension onto the surface of a petri dish. Subsequently, small volumes of the original cell suspension droplet were mixed into droplets of phosphate buffered saline in a serial dilution until visualization of a single intact cell was achieved. Single cells were transferred to a PCR plate (1 cell per well) and lysed using a lysis buffer consisting of Salt Mix (1M KCl, 25 mM MgCl2, 0.1M Tris-HCl), 0.1M DTT, and the Arcturus PicoPure DNA Extraction Kit from Applied BioSystems. After the lysis buffer is added to each well, the plate is run on the following thermal cycler protocol: 56° C. for 1 hr, 95° C. for 10 min, 25° C. for 15 min, 4° C. hold. The single genomic copies were then used as templates for a PCR reaction.

Genomic DNA Isolation

Genomic DNA from fresh frozen (FF) tissue was extracted using the DNeasy Blood and Tissue Kit (catalog no. 69506, Qiagen), according to the manufacturer's spin-column protocol for purification of total DNA from animal tissues. DNA was extracted from FFPE samples with the QIAAMP™ DNA FFPE Tissue Kit (catalog no. 56404, Qiagen) according to the manufacturer's instructions.

Cell-Free Nucleic Acid Standard Generation

A proof-of-concept plasma model system was established by generating fragmented DNA mixtures for use as cell-free nucleic acid size standards that resemble the size profiles of cell-free DNA (cfDNA) naturally found in plasma. To start, $9 \times 10^6$ cells were lysed in hypotonic lysis buffer (20 mM Tris-Cl pH 7.5, 10 mM NaCl, 3 mM MgCl2) for 15 minutes on ice before 10% Igepal CA-630 (Sigma, St. Louis, Mo.) was added to a final concentration of 0.5%. Nuclei were pelleted by centrifugation at 3,000×g for 10 minutes at 4° C., and then resuspended in 1× MNase Buffer (New England BioLabs, Ipswich, Mass.) before 1000 U of MNase (New England BioLabs) was added. Resuspended nuclei were incubated for 5 minutes at 37° C. to facilitate MNase digestion. Reactions were stopped by the addition of EDTA to a final concentration of 15 mM. Undigested chromatin was removed by centrifugation at 2,000×g for 1 minute. Fragmented DNA was purified using the DNA Clean & Concentrator™-500 kit (catalog no. D4032, Zymo Research, Irvine, Calif.) according to manufacturer's instructions. Fragmentation was confirmed by running the purified samples on a BIOANALYZER™ DNA 1000 chip (Agilent, Santa Clara, Calif.). Mononucleosomal-size DNA fragments were purified by a 2-step purification strategy using AMPURE™ XP (Beckman Coulter, Brea, Calif.). First, to remove large fragments, 0.9× AMPURE™ XP beads were added and allowed to bind before magnetic removal. Next, the supernatant was transferred to a fresh tube, additional AMPURE™ XP beads were added to 2×, and DNA was purified according to manufacturer's instructions. Mononucleosomal DNA fragment size (approximately 150 nt) was confirmed by running the samples on a BIOANALYZER™ DNA 1000 chip-based capillary electrophoresis system (Agilent). Child DNA was titrated into the corresponding father DNA to achieve artificial mixtures with different child DNA fractions. This method generates cell-free size standards with 22q11 region CNVs which mimic cancer plasma samples with variable imbalance between copies of the two 22q11 homologs. Pure father samples were run as controls. Cell-free size standards from cancer cell lines (HCC1954 and HCC2218) were also generated by titrating with the corresponding matched normal cell line (HCC1954BL and HCC2218BL, respectively).

Validation of Tissue Samples

Chromosomal microarray analysis on fresh frozen tissue samples was performed using the Illumina CytoSNP-12 97 genotyping microarray platform as previously described [1]. Analysis of FFPE tissue samples using the Affymetrix ONCOSCAN® microarray platform was carried out according to the manufacturer's protocol.

Massively Multiplex PCR and Sequencing

For the 27,744-plex protocol, samples were pre-amplified for 15 cycles using PCR and 27,744 target-specific assays, an aliquot was then transferred to a second nested 15-cycle PCR reaction. Amplified samples were prepared for sequencing by adding barcoded tags in a 12-cycle PCR reaction. Thus, for the 28,000-plex protocol, 27,744 targets were amplified in a single reaction; targets included SNPs from chromosomes 1, 2, 13, 18, 21 and X, and regions 1p36, 4p16, 5p15, 7q11, 15q11, 17p13, 17p11, 22q11, and 22q13. A modified version of this protocol was used for the 3,000-plex approach where 3,168 target-specific assays were amplified using a 25 cycle PCR reaction allowing a focused analysis of SNPs from chromosomes 1 and 2 and the 22q11 focal region. Sequencing of amplicons was carried out using an Illumina HISEQ™ 2500 sequencer; up to 96 tissue samples or 8-12 plasma samples were sequenced per run. Data was plotted with the relative fraction of one allele (arbitrarily chosen) on the y-axis, and the SNP location along the chromosomal region on the x-axis such that the observed allele fractions at each of the chromosomal regions indicate the overall proportion of the two haplotypes present in the sample; note that sample heterogeneity may confound precise determination of the relative copy number of the two haplotypes in any given cell from measurements made on bulk sample.

Data Analysis

Allelic data distributions were modeled for the following hypotheses: (i) all cells are normal, (ii) presence of cells with a homolog 1 deletion and (iii) presence of cells with a homolog 2 deletion. The likelihood of each of the hypotheses was calculated based on observed Next Generation Sequencing (NGS) data at multiple heterozygous SNPs; sequencing and PCR related errors were taken into account. The algorithm compares predicted distributions with actual allelic distributions as measured from the sample in question, employing a Bayesian-based maximum likelihood approach to determine the relative likelihood of each hypothesis given the observed data across multiple tumor fractions and using the haplotype information deduced from the tumor sample corresponding to the same individual. For example, consider a heterozygous SNP with genotype AB (with dimorphic alleles arbitrarily labeled as A and B). If the homolog with allele A is deleted in some cells, then we expect the ratio of A reads to total reads to go down. Similarly, if the homolog with allele B is deleted, then we expect the ratio of B reads to total reads to go down. The change in this ratio is proportional the fraction of tumor DNA present in the plasma. For cases where one of the deletion hypotheses is more likely than the normal hypothesis across a sufficiently large range of tumor fractions, tumor DNA quantity is determined using a maximum likelihood estimation method across those tumor fractions, otherwise tumor DNA fraction is estimated to be equal to zero.

Validation of CNV Approach

The capacity of this SNP-based massively multiplex PCR (mmPCR) approach to accurately detect CNVs (copy number variants) was established using four separate methods, described below. The performance of the assay was demonstrated using, as input, gDNA, both from large numbers of cells and from single cells, DNA from FFPE tissue, and artificial cell free DNA testing standards that simulate cell free circulating tumor DNA (ctDNA) made by mixing appropriately sized DNA from the tumor and germ line samples.

First, an assay targeting 27,744 SNPs dispersed across 6 whole chromosomes and 9 additional focal regions that cover common deletion syndromes were used to analyze gDNA from 71 characterized cell-line samples having a single deletion in one of the nine deletion syndrome regions; p- and q-arms were analyzed separately. Sensitivity was 100% (71/71) and specificity, including all normal regions among affected samples and an additional 25 unaffected samples, was also 100% ($1,849/1,849$).

Second, six characterized cancer cell lines and at least one normal cell line were analyzed using a 3,168-plex, a 27,744-plex PCR and a SNP microarray. Visual inspection of the plotted allele fractions showed similar fractions over all regions with apparent copy number variations. Data was plotted with the relative fraction of one allele (arbitrarily chosen) on the y-axis, and the SNP location along the chromosomal region on the x-axis such that the observed allele fractions at each of the chromosomal regions indicate the overall proportion of the two haplotypes present in the sample; note that sample heterogeneity may confound precise determination of the relative copy number of the two haplotypes in any given cell from measurements made on bulk sample. To show that the assay has single molecule sensitivity, individual cells were isolated from the aforementioned cancer cell lines, and were analyzed as described above. Plotted allele fractions from single cells were similar to both those observed from large quantities, and also SNP arrays, with minor allowances made for expected heterogeneity. To mimic a heterogeneous tumor profile, and determine the capacity for this method to detect CNVs present in a subpopulation of cells, cancer cells were mixed with normal cells at different ratios. Using a linear titration of the cancer cell line HCC2218 into the matched normal control cell line, a corresponding linear change in the allele ratio was determined.

Third, the ability of this methodology to accurately detect CNVs in tumor tissue was validated by visual comparison of three fresh frozen tissue samples using the 3,000-plex PCR and SNP microarray; similar allele fractions were observed. Buffy coat samples from each of the samples were included as germline controls; no CNVs were detected in these samples by either method. The same mmPCR methodology was successfully applied to detect CNVs from formalin fixed paraffin embedded (FFPE) tissue samples, which typically pose a challenge to SNP microarrays. Similar allele fraction patterns were observed among three tumor samples using the 3,000-plex PCR approach and Affymetrix ONCOSCAN®, a commercially available assay that is capable of evaluating CNVs from FFPE samples. Importantly, no modifications of the multiplex PCR method were required to characterize the FFPE samples. To determine whether the CNVs detected in the tumor tissue samples were somatic CNVs a subset of 13 breast cancer samples which had buffy coat, adjacent non-tumor tissue and tumor tissue samples available were analyzed. No CNVs were observed in any of the buffy coat samples, while CNVs were detected in 84.6% ($11/13$) of the tumor tissue samples.

Fourth, validation of ctDNA quantification in plasma samples was carried out using artificial cell-free DNA standards (PlasmArt) mimicking plasma ctDNA. Cell-free nucleic acid standards corresponding to ctDNA were created in one of two ways: Cell-free nucleic acid standards corresponding to ctDNA with well characterized CNVs were created by titrating DNA from a child with a known CNV in the 22q11.2 region resulting from deletion of the maternal haplotype, into the corresponding father's DNA, which had a normal copy number at the 22q region. Alternately, cell-free nucleic acid standards for tumors were created by titrating tumor cell lines with the corresponding matched normal cell lines (see Materials and Methods). Prior to mixing, the DNA of the samples was processed enzymatically to recreate the DNA fragment size distribution observed in natural cell-free DNA which is derived from an apoptotic process. The limit of quantitation (LOQ) is defined as the lowest concentration at which a mutation could be reliably detected with a given level of accuracy and precision. To determine the LOQ, cell-free nucleic acid standards containing various child:father DNA ratios corresponding to ctDNA levels of 0-10% and cell-free nucleic acid standards containing various tumor: matched normal DNA ratios corresponding to ctDNA levels of 0-50% were run. Copy number variations were detected in samples above 0.2% "ctDNA" or above 0.45% "ctDNA" shown in FIGS. 4A-4E. There were 12 samples per run, and the DOR per SNP.

Application of mmPCR Approach

Following validation of the mmPCR (massively multiplexed PCR) method, the technique was applied to the detection of CNVs in tumor tissue and plasma samples from 97 cancer patients. The 3,000-plex mmPCR method focusing on five chromosomal regions was applied for analyses of CNVs in these samples as this focused approach allows a greater depth of read. Overall, somatic copy number variations were detected in at least one of the five regions assayed in 88.9% ($40/45$) of breast tumor tissue samples, 66.7% ($16/24$) of lung tumor tissue samples and 46.4% ($13/28$) of colon tumor tissue samples and were detected across all five regions of interest evaluated. The regions-of-interest included in this panel were not focused on cancer related CNVs; use of a targeted panel of CNVs commonly associated with cancer would be expected to provide significantly greater coverage.

The ability of the mmPCR method to detect the somatic CNVs observed in the tumor tissue in the matched patient plasma samples was then investigated. Overall, copy number variations were detected in breast plasma samples, lung plasma samples and colon plasma samples, and were detected across all five regions-of-interest evaluated.

Tumor Heterogeneity

One of the potential advantages of liquid biopsies is that ctDNA may reveal the spectrum of tumor-associated mutations that exist in the tumor, unlike a focal tumor biopsy that could miss some or all tumor-associated CNVs because of tissue heterogeneity. To determine the effects of tumor heterogeneity on the detection of CNVs in plasma versus focal biopsies, a number of subsections from eight breast cancer samples were analyzed, and compared to the matching plasma sample. Several regions assayed in the 8 samples showed significant heterogeneity between biopsies. Interestingly, one of these samples had a CNV on 22q11 detected in the plasma that was not visible in some of the tumor tissue sections, while a second sample had a CNV on 1q detected in the plasma that was not visible in some of the tumor sections.

Example 4

Tumor Standards for Single Nucleotide Variants (SNV)

To expand on the development of tumor standards for copy number variation (see, Example 3) we hypothesized that genetic nucleic acid standards can be prepared using wild-type gDNA that is mixed with one or more nucleic acid preparations containing known single nucleotide variations (e.g., DNA derived from one or more tumor cells).

One sample of wild-type monosomal DNA (AG16778) was characterized on a BIOANALYZER™ electrophoresis system and quantified by QUBIT™. One pool of 13 dsDNA SNV "spikes" (see "spike PCR" below and Tables 1 and 2) were titrated into wild-type monosomal DNA to verify spike quality and limits of detection in PlasmArt libraries.

TABLE 1

Primer sequences and melting temperature for spike PCR amplification.

| FW Primer Name | Sequence | Melt Tm ° C. | REV Primer Name | Sequence | Melt Tm ° C. | Mut spike |
|---|---|---|---|---|---|---|
| P-D2_1_wt_FW SEQ ID NO: 1 | TACCTCTATTGTTGGAT CATATTC | 49.9 | P-D2_1_wt_REV SEQ ID NO: 2 | TAATATAGTCACATTTTCATTAT TTTTAT | 47.0 | 1, 2, 3 |
| P-D2_9_wt_FW SEQ ID NO: 3 | ACCCTGGGCAACCAGC CCTGT | 66.5 | P-D2_9_wt_REV SEQ ID NO: 4 | CCACACCCCGCCCGGCAC | 69.8 | 14, 15 |
| P-D2_11_wt_FW SEQ ID NO: 5 | TCGTGGTGAGGCTCCCC TTTCT | 62.5 | P-D2_11_wt_REV SEQ ID NO: 6 | GACCTGATTTCCTTACTGCCTCT TG | 57.3 | 17, 18 |
| P-D2_12_wt_FW SEQ ID NO: 7 | CACTGACAACCACCCTT AACC | 55.8 | P-D2_12-wt_REV SEQ ID NO: 8 | CCCTCCTCAGCATCTTATCCG | 56.9 | 19 |
| P-D2_13_wt_FW SEQ ID NO: 9 | ACCACCACACTATGTCG AAAAG | 55.0 | P-D2_13_wt_REV SEQ ID NO: 10 | TGGAGAGACGACAGGGCTG | 59.0 | 21 |
| P-D2_18_wt_FW SEQ ID NO: 11 | CCAGTGTGCAGGGTGGC AAG | 61.5 | P-D2_18_wt_REV SEQ ED NO: 12 | GGCCTGTGTTATCTCCTAGGTT G | 57.0 | 26, 27 |
| P-D2_28_wt_FW SEQ ID NO: 13 | ATGCAGGGGGATACGG CCA | 61.7 | P-D2_28_wt_REV SEQ ID NO: 14 | TGTCATCTTCTGTCCCTTCCCAG | 58.3 | 38 |
| P-D2_31_wt_FW SEQ ID NO: 15 | GAAAGGTGATAAAAGT GAATCTGAG | 51.9 | P-D2_31_wt_REV SEQ ID NO: 16 | GGAGAGACCGGCGCACAG | 61.2 | 41 |

TABLE 2

Exemplary spike pool with 13 spikes

| #Chr | Pos | Gene | Primer Pool | Ref | Sub | Type | Spike mut |
|---|---|---|---|---|---|---|---|
| chr12 | 25398284 | KRAS | 3 | C | T | TRANSITION | mut-1 |
| chr12 | 25398284 | KRAS | 3 | C | G | TRANSVERSION | mut-2 |
| chr12 | 25398284 | KRAS | 3 | C | A | TRANSVERSION | mut-3 |
| chr17 | 7578404 | TP53 | 2 | A | T | TRANSVERSION | mut-14 |
| chr17 | 7578404 | TP53 | 2 | A | C | TRANSVERSION | mut-15 |
| chr17 | 7577124 | TP53 | 2 | C | delC | DELETION | mut-17 |
| chr17 | 7577124 | TP53 | 2 | C | T | TRANSITION | mut-18 |
| chr17 | 7578202 | TP53 | 2 | A | C | TRANSVERSION | mut-19 |
| chr17 | 7578275 | TP53 | 1 | G | A | TRANSITION | mut-21 |
| chr17 | 7577547 | TP53 | 3 | C | A | TRANSVERSION | mut-26 |
| chr17 | 7577547 | TP53 | 3 | C | T | TRANSITION | mut-27 |
| chr17 | 7579329 | TP53 | 2 | T | C | TRANSITION | mut-38 |
| chr17 | 7577022 | TP53 | 1 | G | A | TRANSITION | mut-41 |

The wild-type sample (50,000 copies/rxn) was mixed with seven different percentages of "spikes" (12.5%, 2.5%, 0.5%, 0.25%, 0.1%, 0.025% and 0.01%, each in triplicate). Please note: The percentage refers to the mutation locus only. At that locus, we have 12.5% etc. of spike and the rest is wild-type. It is calculated based on the number of copies of wild-type sequence and mutant sequence. For example, we have 50,000 copies of wild-type (in this case it refers to genome copies; the genome is ~3.3 pg, so 50,000 copies is ~165 ng) and 6250 copies of mutant spike for 12.5%. All spikes were PCR-amplified in single-plex PCR to generate large quantities of DNA. Each spike was purified, normalized and mixed at equimolar concentrations into one spike pool. The spike pool was diluted into wild-type monosomal DNA to reduce DNA loss. A total of 35 wild type controls (with 50,000 copies) were included for error rate calculation.

All samples were prepared using Natera Library Preparation Reagents (Part No. 131100), with amplification to plateau (15 cycles) and using an AMPURE™ nucleic acid clean-up system according to the manufacturer's instructions. Libraries were used for ONESTAR™ (45 Assays, 1KRAS and 44 TP53 in 4 sub-pools) amplification with each of the four Ovarian SNV panel sub-pools (10- to 14-plex), and the ONESTAR™ products were single barcoded, pooled and sequenced (paired end sequencing). The expected DOR/target was ~100,000.

Spike PCR

The primer pairs of Table 1 were diluted to a concentration of 5 uM. Each ssDNA spike was diluted to a concentration of 5 nM. PCR was performed using 10 ul 2× Master Mix (Qiagen), 2 ul FW primer (5 uM), 2 ul REV primer (5 uM), 2 ul ssDNA template Ultramer oligonucleotide (5 nM), 4 ul ultra-pure water (for a total volume of 20 ul) under the following conditions: 95° C. 15 min, 10 cycles [94° C. for 30 sec, 55° C. for 90 sec, 72° C. for 30 sec], 72° C. for 2 min, and held at 4° C. to generate nucleic acid spikes of 160 base pairs in length. Each of the PCR amplified dsDNA spikes were purified using a PCR purification kit according to the manufacturer's instructions (Qiagen). Each amplified dsDNA spike was assessed using a high specificity LAB-CHIP™ automated DNA analysis system and quantified by QUBIT™ fluorometer (see Table 3). The spikes were then pooled at equimolar concentrations and the "spike" pool was diluted in DNA suspension buffer that contained 1 ng/ul monosomal DNA.

TABLE 3

Spike quantification using QUBIT™ and molecule/ul calculation

| spike mut | ng/ul | total 50 ul | molecules/ul | molecules total |
|---|---|---|---|---|
| mut-1 | 1.08 | 54.0 | 2.07E+09 | 1.03E+11 |
| mut-2 | 1.03 | 51.5 | 1.97E+09 | 9.86E+10 |
| mut-3 | 0.99 | 49.5 | 1.90E+09 | 9.48E+10 |
| mut-14 | 1.15 | 57.5 | 2.20E+09 | 1.10E+11 |
| mut-15 | 1.09 | 54.5 | 2.09E+09 | 1.04E+11 |
| mut-17 | 1.63 | 81.5 | 3.12E+09 | 1.56E+11 |
| mut-18 | 1.39 | 69.5 | 2.66E+09 | 1.33E+11 |
| mut-19 | 1.31 | 65.5 | 2.51E+09 | 1.25E+11 |
| mut-21 | 1.36 | 68.0 | 2.60E+09 | 1.30E+11 |
| mut-26 | 2.37 | 118.5 | 4.54E+09 | 2.27E+11 |
| mut-27 | 1.87 | 93.5 | 3.58E+09 | 1.79E+11 |
| mut-38 | 1.36 | 68.0 | 2.60E+09 | 1.30E+11 |
| mut-41 | 1.71 | 85.5 | 3.27E+09 | 1.64E+11 |

Spike Pool Dilution

The number of molecules for each spike per microliter of spike pool were calculated as follows (see Table 4).

TABLE 4

Volume (ul) of purified spikes for generating a spike pool with $5 \times 10^7$ molecules/ul/spike.

| spike mut | ul stock/ 50,000,000 molecules |
|---|---|
| mut-1 | 2.42 |
| mut-2 | 2.54 |
| mut-3 | 2.64 |
| mut-14 | 2.27 |
| mut-15 | 2.40 |
| mut-17 | 1.60 |
| mut-18 | 1.88 |
| mut-19 | 1.99 |
| mut-21 | 1.92 |
| mut-26 | 1.10 |
| mut-27 | 1.40 |
| mut-38 | 1.92 |
| mut-41 | 1.53 |

LOBIND® tubes were used to create a dilution series (diluted in DNA suspension buffer containing 1 ng/ul monosomal DNA). Here, the monosomal DNA solution was added to LOBIND® tubes and vortexed prior to addition of the spike pool, at each dilution step. After adding the appropriate volume of spike solution the sample was vortexed and spun down twice. The following serial dilutions were prepared:

Tube 1: (1:20): 10 ul spike pool ($5 \times 10^7$ molecules/ul) plus 190 ul DNA suspension buffer with monosomal DNA (final $2.5 \times 10^6$ molecules/ul)

Tube 2: (1:10) 10 ul of tube 1 ($2.5 \times 10^6$ molecules) plus 90 ul DNA suspension buffer with monosomal DNA (final $2.5 \times 10^5$ molecules/ul)

Tube 3: (1:10) 10 ul of tube 2 ($2.5 \times 10^5$ molecules/ul) plus 90 ul DNA suspension buffer with monosomal DNA (final $2.5 \times 10^4$ molecules/ul)

Tube 4: (1:10) 10 ul of tube 3 ($2.5 \times 10^4$ molecules/ul) plus 90 ul DNA suspension buffer with monosomal DNA (final $2.5 \times 10^3$ molecules/ul)

For 12.5% sample: mix 2.5 ul of Tube 4 solution with 37.5 ul wild-type monosomal DNA (4.3 ng/ul); this creates a 40 ul sample containing 165 ng wt monosomal DNA (~50,000 copies) and 6,250 molecules of each spike.

Tube 5: (1:5) 10 ul of tube 4 ($2.5 \times 10^3$ molecules/ul) plus 40 ul DNA suspension buffer with monosomal DNA (final 500 molecules/ul)

For 2.5% sample: mix 2.5 ul of Tube 5 solution with 37.5 ul wild-type monosomal DNA (4.3 ng/ul); this creates a 40 ul sample containing 165 ng wt monosomal DNA (~50,000 copies) and 1,250 molecules of each spike.

Tube 6: (1:5) 10 ul of tube 5 (500 molecules/ul) plus 40 ul DNA suspension buffer with monosomal DNA (final 100 molecules/ul).

For 0.5% sample: mix 2.5 ul of Tube 6 solution with 37.5 ul wild-type monosomal DNA (4.3 ng/ul); this creates a 40 ul sample containing 165 ng wt monosomal DNA (~50,000 copies) and 250 molecules of each spike.

For 0.25% sample: mix 1.25 ul of Tube 6 solution with 37.5 ul wild-type monosomal DNA (4.3 ng/ul) and 1.25 ul DNA suspension buffer; this creates a 40 ul sample containing 165 ng wt monosomal DNA (~50,000 copies) and 125 molecules of each spike.

Tube 7: (1:5) 10 ul of tube 6 (100 molecules/ul) plus 40 ul DNA suspension buffer with monosomal DNA (final 20 molecules/ul).

For 0.1% sample: mix 2.5 ul of Tube 7 solution with 37.5 ul wild-type monosomal DNA (4.3 ng/ul); this creates a 40 ul sample containing 165 ng wt monosomal DNA (50,000 copies) and 50 molecules of each spike.

Tube 8: (1:4) 10 ul of tube 7 (20 molecules/ul) plus 30 ul DNA suspension buffer with monosomal DNA (final 5 molecules/ul).

For 0.025% sample: mix 2.5 ul of Tube 8 solution with 37.5 ul wild-type monosomal DNA (4.3 ng/ul); this creates a 40 ul sample containing 165 ng wt monosomal DNA (~50,000 copies) and 12.5 molecules of each spike.

For 0.01% sample: mix 1 ul of Tube 8 solution with 37.5 ul wild-type monosomal DNA (4.3 ng/ul) and 1.5 ul DNA suspension buffer; this creates a 40 ul sample containing 165 ng wt monosomal DNA (~50,000 copies) and 5 molecules of each spike.

A total of 35 wild type controls (50,000 copies) were included for error rate calculation. Each dilution was performed in triplicate for a total number of 56 samples.

Library Prep

All samples were prepared using Natera Library Preparation Reagents (131100), with amplification to plateau (15 cycles) using the Advantage 2 polymerase mix and an AMPURE™ nucleic acid clean-up step according to the manufacturer's instructions. The libraries were assessed using a high specificity LABCHIP™ automated DNA analysis system and prepared for input into the ONESTAR™ amplification system.

TABLE 5

Plate setup for library preparation

| DNA input (copies) | | | | | | | | | |
|---|---|---|---|---|---|---|---|---|---|
| 50000 | WT only | WT only | WT only | WT only | WT only | 12.5% spike | 12.5% spike | 12.5% spike | A |
| 50000 | WT only | WT only | WT only | WT only | WT only | 2.5% spike | 2.5% spike | 2.5% spike | B |
| 50000 | WT only | WT only | WT only | WT only | WT only | 0.5% spike | 0.5% spike | 0.5% spike | C |
| 50000 | WT only | WT only | WT only | WT only | | 0.25% spike | 0.25% spike | 0.25% spike | D |
| 50000 | WT only | WT only | WT only | WT only | | 0.1% spike | 0.1% spike | 0.1% spike | E |
| 50000 | WT only | WT only | WT only | WT only | | 0.025% spike | 0.025% spike | 0.025% spike | F |
| 50000 | WT only | WT only | WT only | WT only | | 0.01% spike | 0.01% spike | 0.01% spike | G |
| 50000 | WT only | WT only | WT only | WT only | | | | | H |

ONESTAR™ Library Amplification

The libraries prepared above, were used as input for ONESTAR™ amplification (45 Assays, 1 KRAS assay and 44 TP53 assays in 4 sub-pools of 10-14 plex, See Table 6). The reactions were prepared in 10 ul total volumes containing 3 ul library and 2 ul primer (125 nM) (final concentration 25 nM per primer) under the following conditions: 95° C. for 10 min, 10 cycles [95° C. for 30 sec, 60° C. for 15 min, 72° C. for 30 sec], 72° C. for 2 min, and held at 4° C.

TABLE 6

Schematic for the 45 assays of an ovarian SNV cancer panel.
Bold assays refer to mutant spikes of the spike pool.

| Assay # | Assay ID | Gene | Well | Sub-pool | Spike detected |
|---|---|---|---|---|---|
| 1 | chr17: 7573882-7574082 | TP53 | D12 | 1 | |
| 2 | chr17: 7573902-7574117 | TP53 | C12 | 2 | |
| 3 | chr17: 7573918-7574118 | TP53 | F11 | 3 | |
| 4 | chr17: 7576755-7576957 | TP53 | A11 | 4 | |
| 5 | chr17: 7576783-7576983 | TP53 | C2 | 2 | |
| 6 | chr17: 7576797-7576997 | TP53 | C9 | 3 | |
| 7 | chr17: 7576922-7577122 | TP53 | C5 | 1 | Mut-41 |
| 8 | chr17: 7576936-7577152 | TP53 | A5 | 2 | |
| 9 | chr17: 7576958-7577158 | TP53 | C8 | 3 | |
| 10 | chr17: 7576969-7577185 | TP53 | D11 | 4 | |
| 11 | chr17: 7576988-7577205 | TP53 | B3 | 1 | |
| 12 | chr17: 7577006-7577221 | TP53 | F1 | 2 | Mut-18/17 |
| 13 | chr17: 7577023-7577238 | TP53 | E9 | 3 | Mut-18/17 |
| 14 | chr17: 7577041-7577248 | TP53 | B6 | 4 | |
| 15 | chr17: 7577401-7577617 | TP53 | D6 | 1 | |
| 16 | chr17: 7577418-7577633 | TP53 | F12 | 2 | |
| 17 | chr17: 7577434-7577649 | TP53 | D4 | 3 | Mut-26/27 |
| 18 | chr17: 7577450-7577665 | TP53 | D5 | 4 | Mut-26/27 |
| 19 | chr17: 7577466-7577681 | TP53 | D10 | 1 | |
| 20 | chr17: 7577486-7577704 | TP53 | D6 | 2 | |
| 21 | chr17: 7578077-7578296 | TP53 | F1 | 1 | |
| 22 | chr17: 7578102-7578324 | TP53 | F8 | 2 | Mut-19 |
| 23 | chr17: 7578125-7578344 | TP53 | G10 | 3 | |
| 24 | chr17: 7578145-7578360 | TP53 | C9 | 4 | |
| 25 | chr17: 7578162-7578380 | TP53 | C1 | 1 | Mut-21 |
| 26 | chr17: 7578181-7578384 | TP53 | A2 | 2 | |
| 27 | chr17: 7578271-7578488 | TP53 | D10 | 4 | |
| 28 | chr17: 7578289-7578504 | TP53 | E8 | 2 | Mut-14/15 |

TABLE 6-continued

Schematic for the 45 assays of an ovarian SNV cancer panel.
Bold assays refer to mutant spikes of the spike pool.

| Assay # | Assay ID | Gene | Well | Sub-pool | Spike detected |
|---|---|---|---|---|---|
| 30 | chr17: 7578328-7578543 | TP53 | F11 | 1 | |
| 31 | chr17: 7578348-7578563 | TP53 | C7 | 4 | |
| 32 | chr17: 7578364-7578579 | TP53 | D5 | 2 | |

TABLE 6-continued

Schematic for the 45 assays of an ovarian SNV cancer panel.
Bold assays refer to mutant spikes of the spike pool.

| Assay # | Assay ID | Gene | Well | Sub-pool | Spike detected |
|---|---|---|---|---|---|
| 33 | chr17: 7578390-7578606 | TP53 | F9 | 1 | |
| 34 | chr17: 7578407-7578624 | TP53 | G6 | 3 | |
| 35 | chr17: 7578425-7578641 | TP53 | C7 | 2 | |
| 36 | chr17: 7578442-7578654 | TP53 | A4 | 4 | |
| 37 | chr17: 7579212-7579413 | TP53 | E8 | 4 | |
| 38 | chr17: 7579229-7579429 | TP53 | A10 | 2 | Mut-38 |
| 39 | chr17: 7579249-7579466 | TP53 | G5 | 3 | |
| 40 | chr17: 7579277-7579478 | TP53 | C9 | 1 | |
| 41 | chr17: 7579314-7579514 | TP53 | E12 | 2 | |
| 42 | chr17: 7579403-7579603 | TP53 | B2 | 4 | |
| 43 | chr17: 7579421-7579621 | TP53 | C9 | 2 | |
| 44 | chr17: 7579447-7579647 | TP53 | C10 | 3 | |
| 45 | chr17: 7579782-7579982 | TP53 | D10 | 3 | |
| 46 | chr12: 25398181-25398385 | KRAS | A5 | 3 | Mut-1/2/3 |

Barcoding-PCR

The products from the ONESTAR™ amplification were used as input for Barcoding PCR amplification. The reactions were prepared in 10 ul total volumes containing 5 ul 2× Q5 Master Mix, 2 ul Forward-Barcode primer (5 uM) and 2 ul of Reverse Barcode primer (5 uM), 1 ul of 1:10 of the ONESTAR™-product under the following conditions: 98° C. for 2 min, 10 cycles of [98° C. for 20 sec, 68° C. for 20 sec, 72° C. for 20 sec], 72° C. for 2 min, and then held at 4° C.

The barcoded products were pooled (complete sample), purified using a Qiagen PCR purification kit, assessed by BIOANALYZER™ electrophoresis, quantified by QUBIT™ fluorometer, and sequenced on a HISEQ™-2500 Illumina DNA sequencing system, paired end, 50 bp reads single index run.

Results:

All 13 SNV spikes as prepared above were observed as a single peak of 160 bp (see FIGS. 5A-5M). All 13 SNV spikes were quantified using QUBIT™ fluorometer (see Table 3).

A summary of the detection data for each SNV spike, at each percentage dilution, is provided in FIG. 13. No dramatic loss of spikes was observed showing that the dilution in monosomal DNA prevented loss of spikes.

Figure 7A:
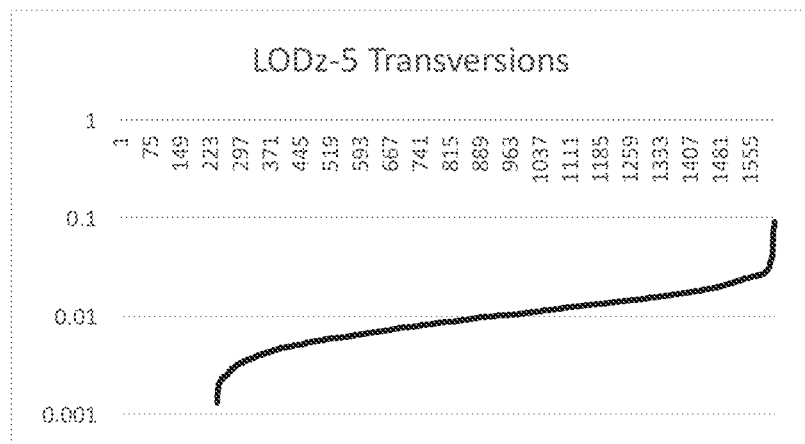
FIG. 7A shows a plot for the detection of transversion events and FIG. 7B shows a plot for the detection of transition events.
Figure 7B:
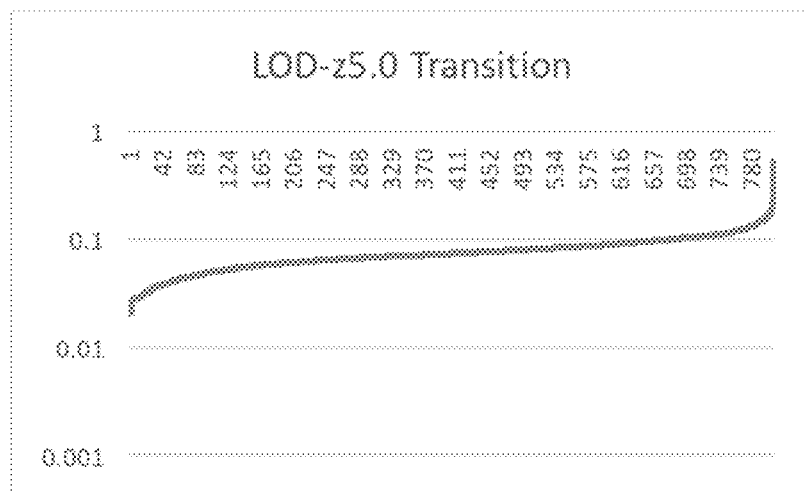

The complete insert for all 45 assays was analyzed on every base and all possible base exchanges. Based on this data, an average error rate for "transversion" events of 0.0016 with an average LODz5 of 0.00937 was observed. For "transition" events, an average error rate of 0.021 and average LODz5 of 0.0769 was observed (see FIG. 6). The LODz5 of all possible Transition and Transversion events in each insert for all 45 assays is plotted in FIGS. 7A and 7B.

Example 5

Detection of SNVs at 0.01% (% Mutant Allele)

To expand on the development of genetic standards for single nucleotide variation (SNV) detection (e.g., Example 4), we hypothesized genetic nucleic acid standards can be prepared having low numbers of mutant alleles, and we performed the following experiment to demonstrate the level of mutant allele detection down to 0.01%.

Assay validation was performed using three human cancer cell lines (HCC1954, HCC2218, and HCC1937) along with a matched normal cell line (HCC1954WT); these cell lines and matched genomic DNA (gDNA) samples were obtained from American Type Culture Collection (ATCC).

Cell Culture

All cell culture reagents (culture medi and fetal bovine serum [FBS]) were obtained from Life Technologies (Foster City, Calif.). ATCC cell lines were cultured according to the ATCC cell culturing, passaging, and cryogenic storage guidelines. Cells were cultured in 10% FBS RPMI 1640 (high glucose with pyruvate) with 2 mM L-Glutamine at 37° C. with 5% CO2. Seed stocks were made of each cell line after one passage, and a cut off of five passages was chosen in order to preserve the genetic stability of each cell line. Cells were washed twice in DPBS to remove FBS and culture media before DNA isolation.

Cell-Free Nucleic Acid Standard Generation

To start, $9 \times 10^6$ cells were lysed in hypotonic lysis buffer (20 mM Tris-Cl pH 7.5, 10 mM NaCl, 3 mM MgCl2) for 15 minutes on ice before 10% Igepal CA-630 (Sigma, St. Louis, Mo.) was added to a final concentration of 0.5%. Nuclei were pelleted by centrifugation at 3,000×g for 10 minutes at 4° C., and then resuspended in 1× MNase Buffer (New England BioLabs, Ipswich, Mass.) before 1000 U of MNase (New England BioLabs) was added. Resuspended nuclei were incubated for 5 minutes at 37° C. to facilitate MNase digestion. Reactions were stopped by the addition of EDTA to a final concentration of 15 mM. Undigested chromatin was removed by centrifugation at 2,000×g for 1 minute. Fragmented DNA was purified using the DNA Clean & Concentrator™-500 kit (catalog no. D4032, Zymo Research, Irvine, Calif.) according to manufacturer's instructions. Fragmentation was confirmed by running the purified samples on a BIOANALYZER™ DNA 1000 chip electrophoresis system (Agilent, Santa Clara, Calif.). Mononucleosomal DNA fragments were purified by a 2-step purification strategy using AMPURE™ XP (Beckman Coulter, Brea, Calif.). First, to remove large fragments, 0.9× AMPURE™ XP beads were added and allowed to bind before magnetic removal. Next, the supernatant was transferred to a fresh tube, additional AMPURE™ XP beads were added to 2×, and DNA was purified according to manufacturer's instructions. Mononucleosomal DNA fragment size (approximately 150 nt) was confirmed by running the samples on a BIOANALYZER™ DNA 1000 chip electrophoresis system (Agilent).

Each cancer cell line (tumor) nucleic acid preparation was titrated into the matched gDNA cell line nucleic acid preparation to achieve artificial mixtures having different target allele percentages shown below (Table 7) (0.5%, 0.15%, 0.06%, 0.03%, 0.01% and 0%). In these mixtures, each of the cancer cell lines carry non-overlapping sets of mutations (as shown in FIG. 8), and the Mut DNA percent is calculated assuming each mutation is heterozygous in each cell line.

TABLE 7

Allele percentages in artificial mixtures

| Mut DNA % | HCC 1954WT | HCC 1954 Mut | HCC 2218 Mut | HCC 1937 Mut |
|---|---|---|---|---|
| 0.5% | 97% | 1% | 1% | 1% |
| 0.15% | 99.1% | 0.3% | 0.3% | 0.3% |
| 0.06% | 99.64% | 0.12% | 0.12% | 0.12% |
| 0.03% | 99.82% | 0.06% | 0.06% | 0.06% |
| 0.01% | 99.94% | 0.02% | 0.02% | 0.02% |
| 0% | 100% | 0% | 0% | 0% |

FIG. 8 provides a list of the single nucleotide variations (SNV) assayed in the four DNA mixtures and the % of mutant alleles.

Library Prep

A total of 9 libraries were prepared. Four libraries were prepared containing 0.01% Tumor DNA, and a further five libraries, one for each of the remaining % Tumor DNA content (i.e., 0%, 0.03%, 0.06%, 0.15% and 0.5%). All samples were prepared using Natera Library Preparation Reagents (131100), with amplification to plateau (15 cycles) using the Advantage 2 polymerase mix and an AMPURE™ clean-up step according to the manufacturer's instructions. The libraries were assessed using a high specificity LAB-CHIP™ automated DNA analysis system and prepared for input onto the ONESTAR™ amplification system.

ONESTAR™ Amplification

The above libraries were used as input for ONESTAR™ amplification. The assay was a 15-plex assay targeting 7 SNVs (see FIG. 9 "Mutation"). The reactions were prepared in 10 ul total volumes containing 2.5 ul library DNA, 0.75 ul 100 nM primer Pool A, 0.75 ul 100 nM primer Pool B, 5 ul 4× Master Mix (Qiagen) and 1 ul EDTA (final concentration 7.5 nM per primer pool) under the following conditions: 95° C. for 15 min, 20 cycles [94° C. for 30 sec, 65° C. for 15 min, 72° C. for 30 sec], 72° C. for 2 min, and held at 4° C.

Barcoding PCR

The products from the ONESTAR™ amplification were diluted 1:40 in water and 1 ul of each was used as input for Barcoding PCR using the Q5 polymerase mix. Dual indexing was performed as follows in a 10 ul total volume (2 ul 5× Q5 buffer, 0.1 ul Q5 polymerase, 0.2 ul dNTPs, 2 ul Forward-Barcode primer (5 uM) and 2 ul of Reverse Barcode primer (5 uM), 1 ul of the ONESTAR™ amplification product, and water to 10 ul, using the following program: 98° C. for 1 min, 15 cycles of [98° C. for 10 sec, 70° C. for 10 sec, 60° C. for 30 sec, 65° C. for 15 sec, 72° C. for 15 sec], 72° C. for 2 min, and then held at 4° C. The barcoded products were pooled, purified using a Qiagen PCR purification kit, assessed by BIOANALYZER™ electrophoresis, quantified by QUBIT™, and sequenced on a HISEQ™ 2500, paired end, 50 bp read single index run.

Results:

The number of mutant detections in each library sample was consistent with expected allele ratio's indicating this method can be used to enrich mutant alleles by sampling biases in low copy number distributed samples, and enabling successful detection of SNV down to 0.01% (% mutant alleles).

Example 6

Non-invasive cell-free tumor DNA based Detection of Breast Cancer-related CNV Validated Using Nucleic Acid Standard Compositions of the Present Invention.

This example describes an exemplary method for non-invasive cell-free tumor DNA-based detection of breast cancer-related copy number variations. Breast cancer screening involves mammography, which results in a high false positive rate and misses some cancers. Analysis of tumor-derived circulating cell-free DNA (ctDNA) for cancer-associated CNVs may allow for earlier, safer, and more accurate screening. A SNP-based massively multiplex PCR (mmPCR) approach was used to screen cfDNA for CNVs in the plasma of breast cancer patients. The mmPCR assay was designed to target 3,168 SNPs on chromosomes 1, 2, and 22, which often have CNVs in cancer (e.g., 49% of breast cancer samples have a 22q deletion). Six plasma samples from breast cancer patients—one stage IIa, four stage IIb, and one stage IIIb—were analyzed. Each sample had CNVs on one or more of the targeted chromosomes. The assay identified CNVs in all six plasma samples, including in one stage IIb sample that was correctly called at a ctDNA fraction of 0.58%; detection only required 86 heterozygous SNPs. A stage IIa sample was also corrected called at a ctDNA fraction of 4.33% using approximately 636 heterozygous SNPs. This demonstrates that focal or whole chromosome arm CNVs, both common in cancer, can be readily detected using massively multiplex PCR (mmPCR) and combined with illustrative analytical methods.

CNVs were identified using analytical methods that used a maximum likelihood algorithm that searched for plasma CNVs in regions where the tumor sample from the same individual also had CNVs, using haplotype information deduced from the tumor sample. This algorithm modeled expected allelic frequencies across a set of average allelic imbalances at 0.025% intervals for three sets of hypotheses: (1) all cells are normal (no allelic imbalance), (2) some/all cells have a homolog 1 deletion or homolog 2 amplification, or (3) some/all cells have a homolog 2 deletion or homolog 1 amplification. For at least some of the analysis, modeling was performed up to 15% average allelic imbalance, although for the vast majority of samples AAI was less than or equal to 5%. The likelihood of each hypothesis was determined at each SNP using a Bayesian classifier based on a beta binomial model of expected and observed allele frequencies at all heterozygous SNPs, and then the joint likelihood across multiple SNPs was calculated taking linkage of the SNP loci into consideration. The maximum likelihood hypothesis from the comparison of expected to observed allele frequencies was then selected.

Figure 10:
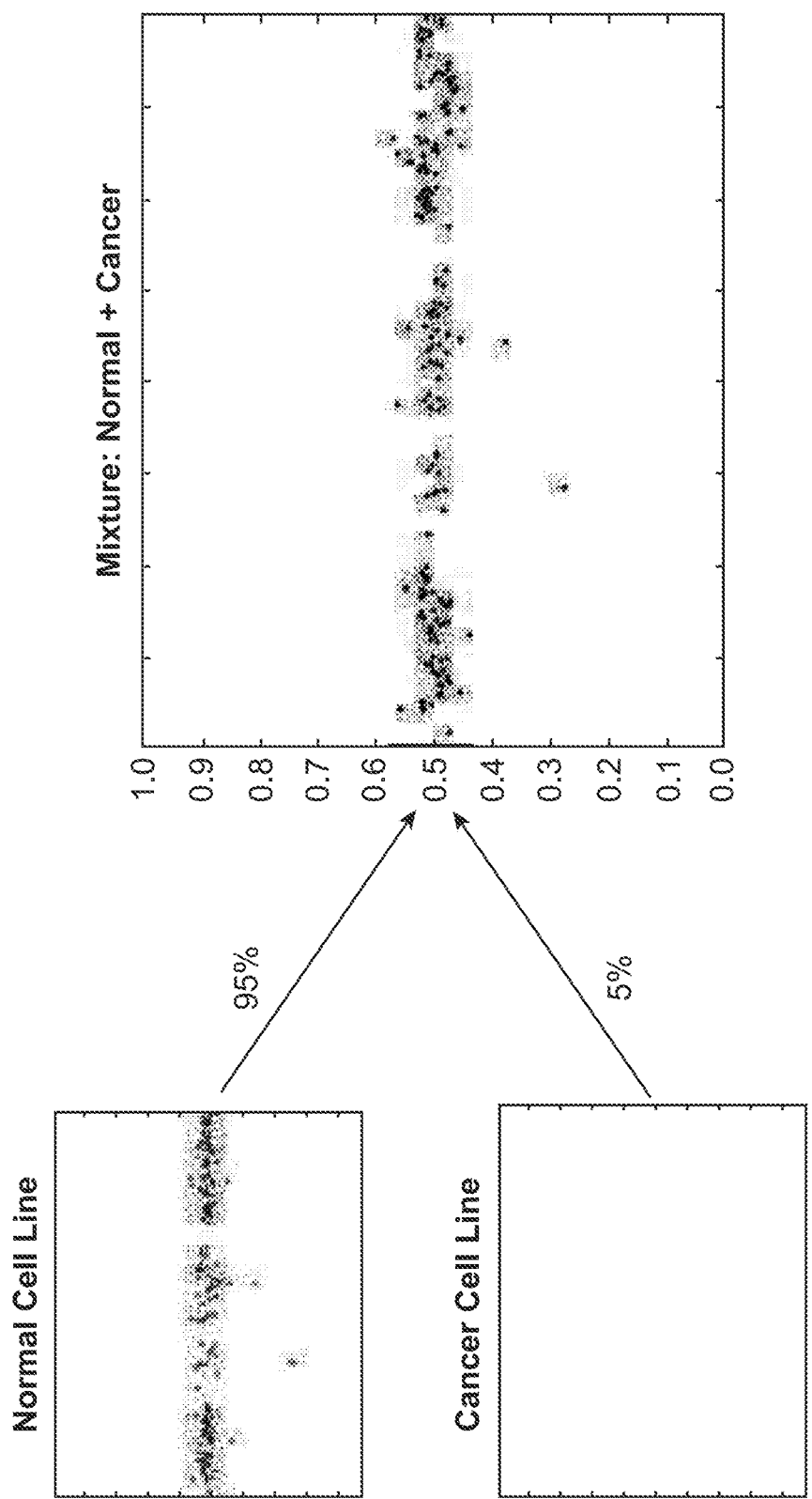
FIG. 10 shows three graphs of reference counts (counts of one allele, such as the "A" allele) divided by total counts for that locus for a normal (noncancerous) cell line, a cancer cell line with a deletion, and for a mixture of DNA from the normal cell line and the cancer cell line.

To further evaluate sensitivity, 22 artificial mixtures containing a 3 Mb 22q CNV from a cancer cell line were mixed with DNA from a normal cell line (5:95) to simulate a ctDNA fraction of between 0.43% and 7.35% (FIG. 10). The method correctly detected CNVs in 100% of these samples. Thus, artificial cfDNA polynucleotide standards can be made by spiking isolated polynucleotide samples that include fragmented polynucleotide mixtures generated by non-cfDNA sources known to exhibit CNV, such as tumor cell lines, into other DNA samples at concentrations similar to those observed for cfDNA in vivo, such as between, for example, 0.01% and 20%, 0.1% and 15%, or 0.4% and 10% of DNA in that fluid. These standards can be used as controls for assay design, characterization, development, and/or validation, and as quality control standards during testing, such as cancer testing performed in a CLIA lab and/or as standards included in research use only or diagnostic test kits.

Example 7

This example further validates a massively multiplexed PCR methodology for chromosomal aneuploidy and CNV determination, sometimes referred to as CoNVERGe (Copy Number Variant Events Revealed Genotypically) in cancer diagnostics, and further illustrates the development and use of the nucleic acid standard compositions, and sets thereof, provided herein, sometimes referred to as "PlasmArt" standards, for use as controls in ctDNA analysis. In certain aspects, nucleic acid standards provided herein, include polynucleotides having sequence identity to regions of the genome known to exhibit CNV and a size distribution that reflects that of cfDNA fragments naturally found in plasma.

Sample Collection

Human breast cancer cell lines (HCC38, HCC1143, HCC1395, HCC1937, HCC1954, and HCC2218) and matched normal cell lines (HCC38BL, HCC1143BL, HCC1395BL, HCC1937BL, HCC1954BL, and HCC2218BL) were obtained from the American Type Culture Collection (ATCC). Trisomy 21 B-lymphocyte (AG16777) and paired father/child DiGeorge Syndrome (DGS) cell lines (GM10383 and GM10382, respectively) were from the Coriell Cell Repository (Camden, N.J.). GM10382 cells only have the paternal 22q11.2 region.

We procured tumour tissues from 16 breast cancer patients, including 11 fresh frozen (FF) samples from Geneticist (Glendale, Calif.) and five formalin-fixed paraffin-embedded (FFPE) samples from North Shore-LIJ (Manhasset, N.Y.). We acquired matched buffy coat samples for eight patients and matched plasma samples for nine patients. FF tumour tissues and matched buffy coat and plasma samples from five ovarian cancer patients were from North Shore-LIJ. For eight breast tumour FF samples, tissue subsections were resected for analysis. Institutional review board approvals from Northshore/LIJ IRB and Kharkiv National Medical University Ethics Committee were obtained for sample collection and informed consent was obtained from all subjects.

Blood samples were collected into EDTA tubes. Circulating cell free DNA was isolated from 1 mL plasma using the QIAAMP™ Circulating Nucleic Acid Kit (Qiagen, Valencia, Calif.). Genomic DNA (gDNA) from FF tumor tissues, blood, and buccal samples was extracted using the DNeasy Blood and Tissue Kit (Qiagen).

To make the PlasmArt standards according to one exemplary method, first, $9 \times 10^6$ cells were lysed with hypotonic lysis buffer (20 mM Tris-Cl (pH 7.5), 10 mM NaCl, and 3 mM $MgCl_2$) for 15 min on ice. Then, 10% IGEPAL CA-630 (Sigma, St. Louis, Mo.) was added to a final concentration of 0.5%. After centrifugation at 3,000 g for 10 min at 4° C., pelleted nuclei were resuspended in 1× micrococcal nuclease (MNase) Buffer (New England BioLabs, Ipswich, Mass.) before adding 1000 U of MNase (New England BioLabs), and then incubated for 5 min at 37° C. Reactions were stopped by adding EDTA to a final concentration of 15 mM. Undigested chromatin was removed by centrifugation at 2,000 g for 1 min. Fragmented DNA was purified with the DNA Clean & Concentrator™-500 kit (Zymo Research, Irvine, Calif.). Mononucleosomal DNA produced by MNase digestion was also purified and size-selected using AMPURE™ XP magnetic beads (Beckman Coulter, Brea, Calif.). DNA fragments were sized and quantified with a BIOANALYZER™ DNA 1000 chip electrophoresis system (Agilent, Santa Clara, Calif.).

To model ctDNA at different concentrations, different fractions of PlasmArt's from HCC1954 and HCC2218 cancer cells were mixed with those from the corresponding matched normal cell line (HCC1954BL and HCC2218BL, respectively). Three samples at each concentration were analyzed. Similarly, to model allelic imbalances in plasma DNA in a focal 3.5 Mb region, we generated PlasmArt's from DNA mixtures containing different ratios of DNA from a child with a maternal 22q11.2 deletion and DNA from the father. Samples containing only the father's DNA were used as negative controls. Eight samples at each concentration were analyzed.

Massively Multiplexed PCR and DNA Sequencing

Massively multiplex PCR and DNA sequencing methods below were used to determine allele counts at a plurality of polymorphic loci with 3-6 million (M) reads/sample for cell lines, 1.5-7 M reads/sample for tumour tissues, 18 M reads/sample for FFPE-LCM samples, 6-7 M reads/sample for germline controls, and 18-25 M reads/sample for plasma. The fraction of sequencing reads at a given locus with a particular allele (allele fraction) was the fractional abundance of the allele in a sample These counts provided observed allele frequencies that were used by the data analysis methods provided immediately below in this Example to determine the ploidy state of a chromosome or chromosome segment of interest and/or to determine the average allelic imbalance of the sample.

Libraries were generated from the samples above. Adapters were ligated to DNA fragments and the fragments were amplified using the following protocol: 95° C., 2 min; 15×[95° C., 20 sec, 55° C., 20 sec, 68° C., 20 sec], 68° C. 2 min, 4° C. hold.

Multiplexed PCR allows simultaneous amplification of many targets in a single reaction. In this study, we targeted 3,168 SNPs, which were distributed across five chromosome arms as follows: 646 on 1p, 602 on 1q, 541 on 2p, 707 on 2q, and 672 on the 22q11.2 focal region. These genomic regions were selected for convenience from SNP panels available in our laboratory. Target SNPs had at least 10% population minor allele frequency (1000 Genomes Project data; Apr. 30, 2012 release) to ensure that a sufficient fraction would be heterozygous in any given patient. For each SNP, multiple primers were designed to have a maximum amplicon length of 75 bp and a melting temperature between 54.0-60.5° C. To minimize the likelihood of primer dimer product formation, primer interaction scores for all possible combinations of primers were calculated, and primers with high scores were eliminated. Candidate PCR assays were ranked and 3,168 assays were selected on the basis of target SNP minor-allele frequency, observed heterozygosity rate (from dbSNP), presence in HapMap, and amplicon length.

For PCR amplifications, 3,168 SNPs were amplified in a multiplex PCR reaction using one primer pair for each SNP, during 25 cycles, and sequencing barcodes were added in 12 additional cycles. Prior to sequencing, the barcoded products were pooled, purified with the QIAQUICK™ PCR Purification Kit (Qiagen), and quantified using the QUBIT™ dsDNA BR Assay Kit (Life Technologies). Amplicons were sequenced using an Illumina HISEQ™ 2500 sequencer with 1.5-7 M reads/sample for tumor tissue DNA and 18-25 M reads/sample for plasma cfDNA.

For the 3,168 SNP multiplex PCR reaction, approximately 7 ul (approx. 1200 ng) of library DNA, such as DNA from a DNA library generated from plasma of a target individual, was used. The master mix included the following: 2× (twice manufacturer's recommended concentration) Qiagen master mix, 70 mM TMAC (tetramethylammonium chloride, Sigma), 2 nM each primer, and 7 ul nucleic acid library (1200 ng total library input) (20 ul total volume). The cycling conditions for the 3,168 SNP multiplex PCR reaction were as follows: 95° C., 15 min; 25×[96° C., 30 sec; 65° C., 20 min; 72° C., 30 sec]; 72° C., 2 min; 4° C. hold.

For the barcoding reaction, a 1× master mix was prepared that included the following: 1 uM forward primer (containing Illumina sequencing tag), 1 uM reverse primer (containing Illumina sequencing tag as well as internally-designed sequencing barcode), 1 ul of mmPCR product, diluted 1:2,000 and 1× Qiagen master mix. Barcoding cycling conditions were as follows: 95° C., 10 min; 12×[95° C., 30 sec; 70° C., 10 sec, 60° C., 30 sec; 65° C., 15 sec, 72° C., 15 sec]; 72° C., 2 min; 4° C. hold.

Data Analysis of Tumor Tissue Genomic DNA

For tumor tissue samples, CNVs were delineated by transitions between allele frequency distributions. Regions with at least 100 SNPs that had an allele ratio statistically different from 0.50 were considered to be of interest. More specifically, the analysis focused on regions with average allele ratios of ≤0.45 or ≥0.55 for loci that are heterozygous in the germline. A segmentation algorithm was used to exhaustively search DNA sequences in five chromosome arms as follows: 646 on 1p, 602 on 1q, 541 on 2p, 707 on 2q, and 672 on the 22q11.2 for such regions, and iteratively selected them starting from the longest one until a region of 100 SNPs was reached. Once a ≥100 SNP region was determined to contain a CNV, it was further segmented by average allelic ratios with a minimum segment size of 50 SNPs if needed.

Fresh frozen tissue samples from three patients with breast cancer were also analyzed using Illumina CytoSNP-12 microarrays as previously described (Levy, B. et al. Genomic imbalance in products of conception: single-nucleotide polymorphism chromosomal microarray analysis. Obstetrics and gynecology 124, 202-209 (2014)).

Data Analysis of Circulating Tumor DNA

CNVs were identified by a maximum likelihood algorithm that searched for plasma CNVs in regions where the tumor sample from the same individual also had CNVs, using haplotype information deduced from the tumor sample. This algorithm modeled expected allelic frequencies across a set of average allelic imbalances at 0.025% intervals for three sets of hypotheses: (1) all cells are normal (no allelic imbalance), (2) some/all cells have a homolog 1 deletion or homolog 2 amplification, or (3) some/all cells have a homolog 2 deletion or homolog 1 amplification. For at least some of the analysis, modeling was performed up to 15% average allelic imbalance, although for the vast majority of samples AAI was less than or equal to 5%. The likelihood of each hypothesis was determined at each SNP using a Bayesian classifier based on a beta binomial model of expected and observed allele frequencies at all heterozygous SNPs, and then the joint likelihood across multiple SNPs was calculated taking linkage of the SNP loci into consideration. The maximum likelihood hypothesis from the comparison of expected to observed allele frequencies was then selected. This algorithm also calculates the confidence of each CNV call by comparing the likelihoods of different hypotheses. A confidence threshold of 99.9% was used in plasma samples to minimize false positive results.

For dimorphic SNPs that have alleles arbitrarily designated 'A' and 'B', the allele ratio of the A allele is nA/(nA+nB), where nA and nB are the number of sequencing reads for alleles A and B, respectively. Allelic imbalance is the difference between the allele ratios of A and B for loci that are heterozygous in the germline. This explanation is analogous to that for SNVs, where the proportion of abnormal DNA is typically measured using mutant allele frequency, or nm/(nm+nr), where nm and nr are the number of sequencing reads for the mutant allele and the reference allele, respectively.

Consider a chromosomal region with an average of N copies in the tumor, and let c denote the fraction of DNA in plasma derived from the mixture of normal and tumour cells in a disomic region. AAI was calculated as:

$$AAI = \frac{c|N-2|}{2+c(N-2)}$$

Allele frequency data was corrected for errors before it was used to generate individual probabilities. Errors that were corrected included allele amplification bias, ambient contamination, genotype contamination, and sequencing error. Ambient contamination refers to the contamination error across all SNPs in addition to sequencing errors, and genotype contamination refers to the additional contamination at some SNPs due to contamination from another sample. Ambient contamination and genotype contamination were determined on the same run as the on-test sample analysis by analyzing homozygous alleles in the sample. The ploidy status of a chromosomal segment was estimated using heterozygous loci for a test individual.

Best hypothesis was defined to be the one with the highest likelihood across all polymorphic loci. Likelihood at each locus was calculated using a beta binomial model of observed allele frequencies at each of the polymorphic loci, and the likelihood across a set of polymorphic loci was computed using the phase information deduced from the corresponding tumor sample.

A linear regression model was used to compare either expected AAI or tumor input DNA percentage and observed AAI determined by the CNV detection algorithm. $P<0.05$ was considered statistically significant. SigmaPlot 12.5 (Systat Software, San Jose, Calif.) and Matlab 7.12.0 R2011.a (MathWorks, Natick, Mass.) were used.

Figure 11A:
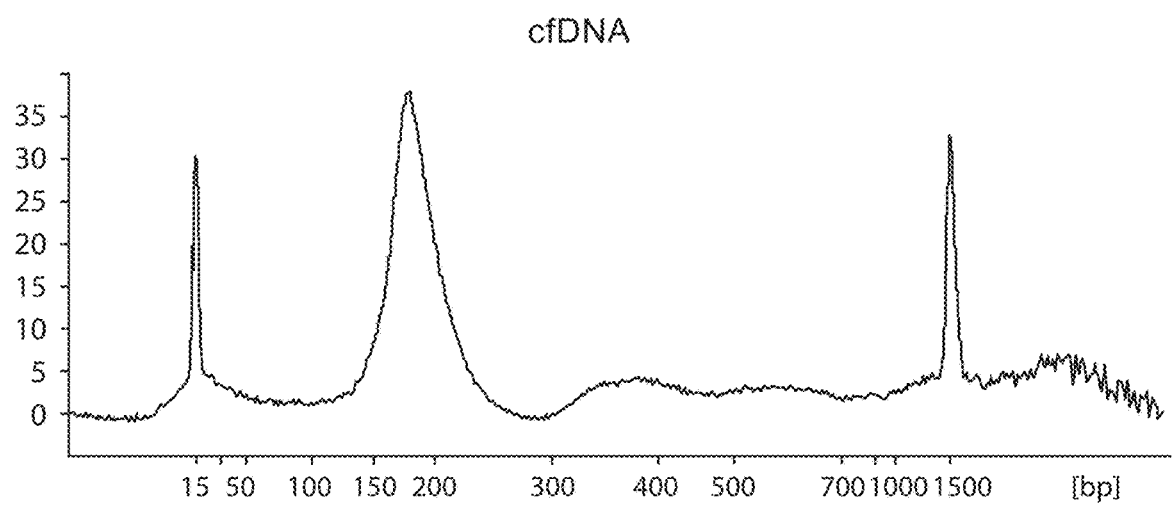
FIGS. 11A and 11B provide fragment size distributions for an exemplary nucleic acid standard composition prepared as discussed in the relevant Example herein.
Figure 11B:
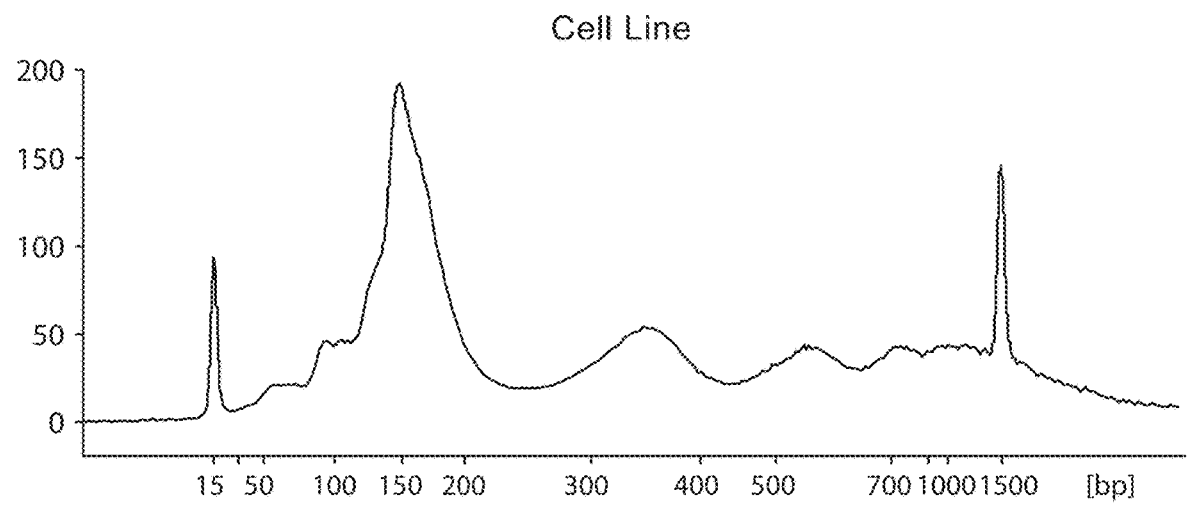
Figure 12A:
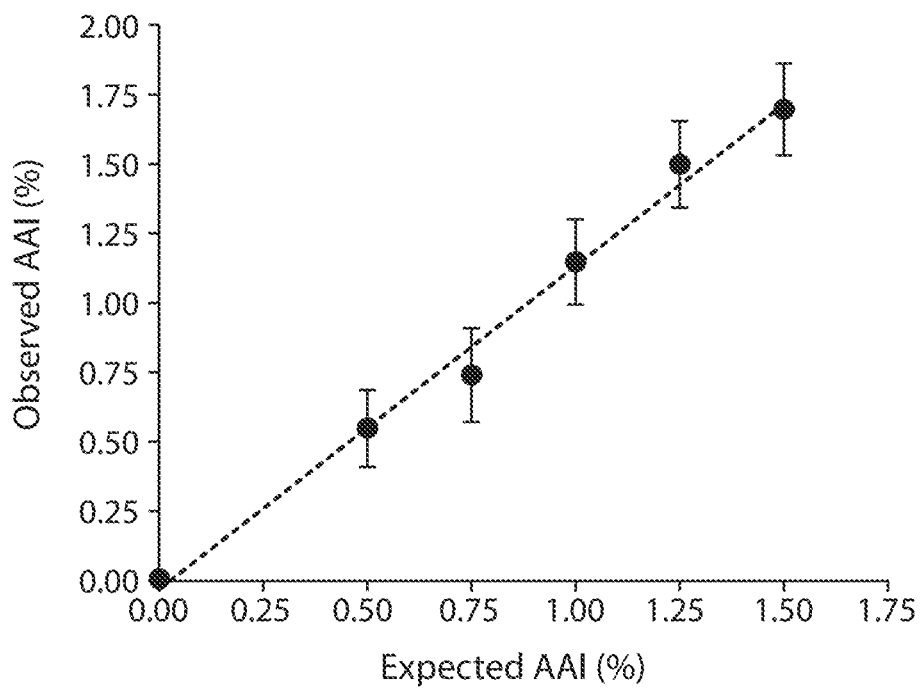
FIGS. 12A-D are graphs of sensitivity of CoNVERGe determined with PlasmArt standards. (a) Correlation between CoNVERGe-calculated AAI and actual input fraction in PlasmArt samples with DNA from a 22q11.2 deletion and matched normal cell lines. (b) Correlation between calculated AAI and actual tumour DNA input in PlasmArt samples with DNA from HCC2218 breast cancer cells with chromosome 2p and 2q CNVs and matched normal HCC2218BL cells, containing 0-9.09% tumour DNA fractions. (c) Correlation between calculated AAI and actual tumour DNA input in PlasmArt samples with DNA from HCC1954 breast cancer cells with chromosome 1p and 1q CNVs and matched normal HCC1954BL cells, containing 0-5.66% tumour DNA fractions. (d) Allele frequency plot for HCC1954 cells used in (c). In (a), (b), and (c), data points and error bars indicate the mean and standard deviation (SD), respectively, of 3-8 replicates.

Accordingly, to evaluate the sensitivity and reproducibility of CoNVERGe, especially when the proportion of abnormal DNA for a CNV, or average allelic imbalance (AAI), is low, we used it to detect CNVs in DNA mixtures comprised of a previously characterized abnormal sample titrated into a matched normal sample. The mixtures consisted of artificial cfDNA, termed "PlasmArt", with fragment size distribution approximating natural cfDNA (see above). FIG. 11 graphically displays the size distribution of an exemplary PlasmArt prepared from a cancer cell line compared to the size distribution of cfDNA, looking at CNVs on chromosome arms 1p, 1q, 2p, and 2q. In the first pair, a son's tumor DNA sample having a 3 Mb Focal CNV deletion of the 22q11.2 region was titrated into a matched normal sample from the father at between 0-1.5% total cfDNA (FIG. 12a). CoNVERGe reproducibly identified CNVs corresponding to the known abnormality with estimated AAI of >0.35% in mixtures of ≥0.5%+/−0.2% AAI, failed to detect the CNV in 6/8 replicates at 0.25% abnormal DNA, and reported a value of ≤0.05% for all eight negative control samples. The AAI values estimated by CoNVERGe showed high linearity (R2=0.940) and reproducibility (error variance=0.087). The assay was sensitive to different levels of amplification within the same sample. Based on these data a conservative detection threshold of 0.45% AAI could be used for subsequent analyses.

Figure 12B:
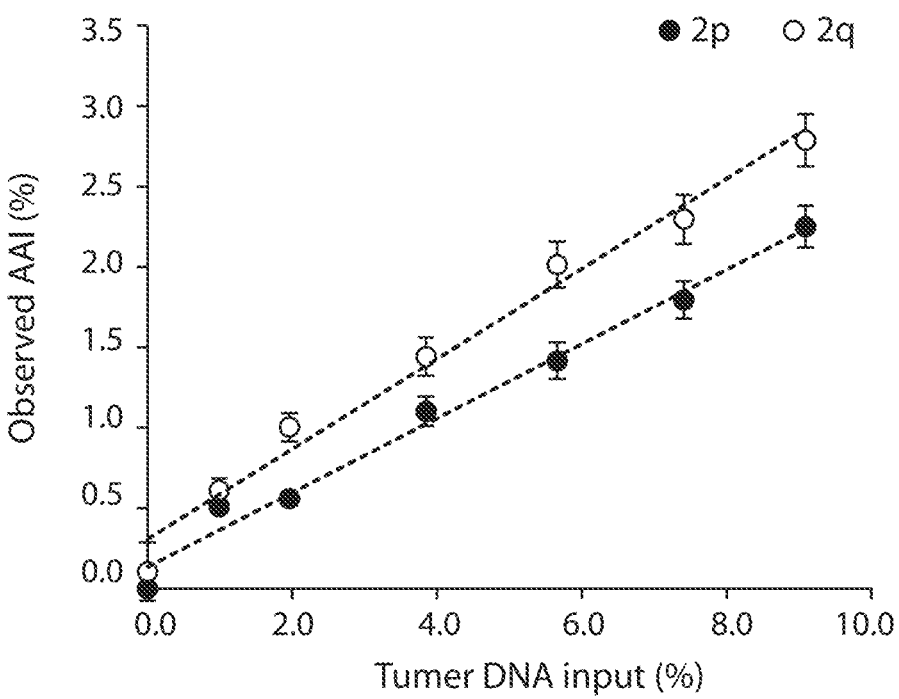
Figure 12C:
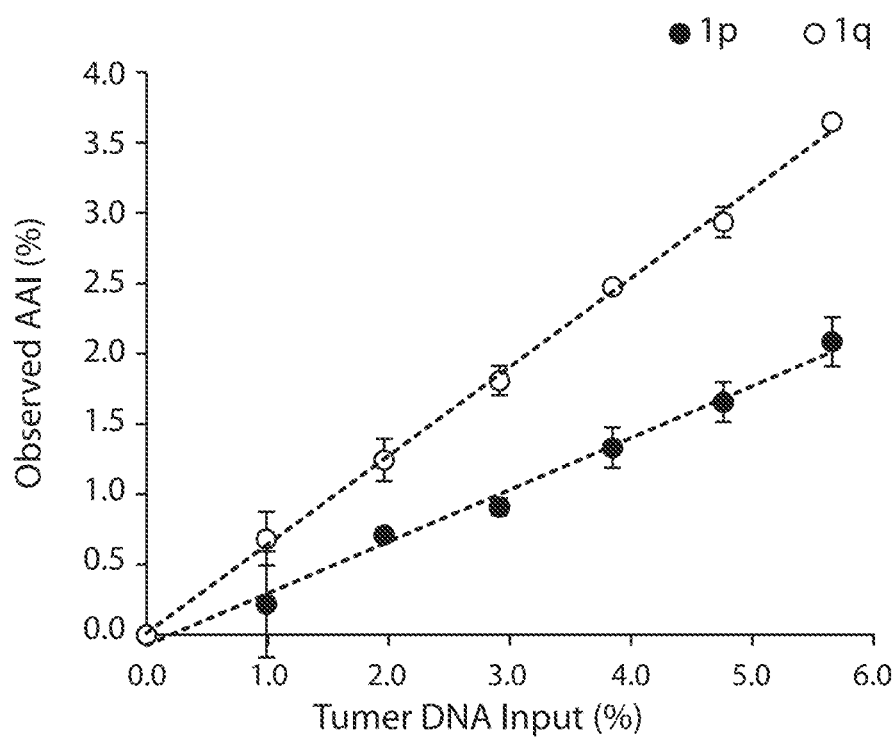
Figure 12D:
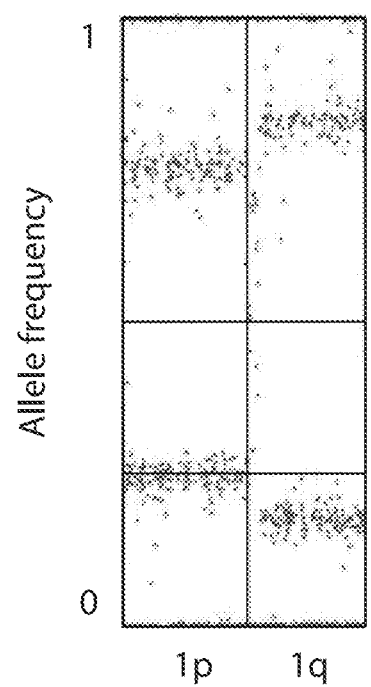

Two additional PlasmArt titrations, prepared from pairs of matched tumor and normal cell line samples and having CNVs on chromosome 1 or chromosome 2, were also evaluated (FIG. 12b, 12c). Among negative controls, all values were <0.45%, and high linearity (R2=0.952 for HCC1954 1p, R2=0.993 for HCC1954 1q, R2=0.977 for HCC2218 2p, R2=0.967 for HCC2218 2q) and reproducibility (error variance=0.190 for HCC1954 1p, 0.029 for HCC1954 1q, 0.250 for HCC2218 2p, and 0.350 for HCC2218 2q) were observed between the known input DNA amount and that calculated by CoNVERGe. The difference in the slopes of the regressions for regions 1p and 1q of one sample pair correlates with the relative difference in copy number observed in the B-allelic frequencies (BAFs) of regions 1p and 1q of the same sample, demonstrating the relative precision of the AAI estimate calculated by CoNVERGe (FIG. 12c, 12d).

CoNVERge has application to a variety of sample sources including FFPE, Fresh Frozen, Single Cell, Germline control and cfDNA. We applied CoNVERGe to six human breast cancer cell lines and matched normal cell lines to assess whether it can detect somatic CNVs. Arm-level and focal CNVs were present in all six tumour cell lines, but were absent from their matched normal cell lines, with the exception of chromosome 2 in HCC1143 in which the normal cell line exhibits a deviation from the 1:1 homolog ratio. To validate these results on a different platform, we performed CytoSNP-12 microarray analyses, which produced consistent results for all samples. Moreover, the maximum homolog ratios for CNVs identified by CoN-VERGe and CytoSNP-12 microarrays exhibited a strong linear correlation ($R2=0.987$, $P<0.001$).

We next applied CoNVERGe to fresh-frozen (FF) and formalin-fixed, paraffin-embedded (FFPE) breast tumour tissue samples. In both sample types, several arm-level and focal CNVs were present; however, no CNVs were detected in DNA from matched buffy coat samples. CoNVERGe results were highly correlated with those from microarray analyses of the same samples ($R2=0.909$, $P<0.001$ for CytoSNP-12 on FF; $R2=0.992$, $P<0.001$ for ONCOSCAN® on FFPE). CoNVERGe also produces consistent results on small quantities of DNA extracted from laser capture microdissection (LCM) samples, for which microarray methods are not suitable.

Detection of CNVs in Single Cells with CoNVERGe

To test the limits of the applicability of this mmPCR approach, we isolated single cells from the six aforementioned cancer cell lines and from a B-lymphocyte cell line that had no CNVs in the target regions. The CNV profiles from these single-cell experiments were consistent between three replicates and with those from genomic DNA (gDNA) extracted from a bulk sample of about 20,000 cells. On the basis of the number of SNPs with no sequencing reads, the average assay drop-out rate for bulk samples was 0.48% (range: 0.41-0.60%), which is attributable to either synthesis or assay design failure. For single cells, the additional average assay drop-out rate observed was 0.39% (range: 0.19-0.67%). For single cell assays that did not fail (i.e. no assay drop-out occurred), the average single ADO rate calculated using heterozygous SNPs only was 0.05% (range: 0.00-0.43%). Additionally, the percentage of SNPs with high confidence genotypes (i.e. SNP genotypes determined with at least 98% confidence) was similar for both single cell and bulk samples and the genotype in the single cell samples matched those in the bulk sample (average 99.52%, range: 92.63-100.00%).

In single cells, allele frequencies are expected to directly reflect chromosome copy numbers, unlike in tumour samples where this may be confounded by TH and non-tumour cell contamination. BAFs of $1/n$ and $(n-1)/n$ indicate n chromosome copies in a region. Chromosome copy numbers are indicated on the allele frequency plots for both single cells and matched gDNA samples.

Application of CoNVERGe to Plasma Samples

To investigate the ability of CoNVERGe to detect CNVs in real plasma samples, we applied our approach to cfDNA paired with a matched tumour biopsy from each of two stage II breast cancer patients and five late-stage ovarian cancer. In all seven patients, CNVs were detected in both FF tumour tissues and in the corresponding plasma samples. A total of 32 CNVs, at a level of $\geq 0.45\%$ AAI, were detected in the seven plasma samples (range: 0.48-12.99% AAI) over the five regions assayed, which represent about 20% of the genome. Note that the presence of CNVs in plasma cannot be confirmed due to the lack of alternative orthogonal methods.

Example 8

Genetic Standards for CNV and SNV Detection

Detection of genomic insertions, deletions, indels, single nucleotide variations or chromosomal rearrangements such as inversions, duplications, translocations, or gene fusion junction locations has been shown to identify genes and chromosomal regions of interest in various disease states including cancer, genetic disorders, and non-invasive prenatal testing. Paired end sequencing data has been shown to reliably detect such altered regions of the genome. We present here in Example 3, the development of genetic nucleic acid standards for the detection of copy number variants (CNV). Additionally, we present in Examples 4 and 5, the development of genetic nucleic acid standards for the detection of single nucleotide variations (SNV), including the detection of 0.01% mutant alleles. It is to be understood that the methods for preparing a CNV genetic nucleic acid standard and/or a SNV genetic nucleic acid standard is not limited to the methods presented herein, and thus other methods to prepare nucleic acid libraries and resulting nucleic acid standards having either a CNV and/or SNV, known to one of ordinary skill in the art are anticipated as being within the scope of the present invention.

An additional beneficial tool for mutation detection, disease monitoring, and structural genetic variation analysis would involve the use of combined CNV and SNV genetic nucleic acid standards. As such, we propose a set of genetic nucleic acid standards having one or more CNV standards (prepared for example according to Example 3 herein) in combination with one or more SNV standards (prepared for example according to Example 4 or 5 herein). Accordingly, at least one of the standard compositions in a set of standard compositions could include both, between 0.01% and 20% of the total nucleic acids present in the standard composition, of a nucleosomal nucleic acid preparation from a cell source that exhibits aneuploidy of a chromosomal region where aneuploidy has been correlated with cancer, and between 0.01% and 20% of the total nucleic acids present in the standard composition, of a synthetic oligonucleotide between 50 and 500 base pairs in length comprising at least 50 contiguous nucleotides having a sequence that is at least 90, 95, 99 or in this illustrative example 100% identical to a genomic sequence comprising or flanking a mutation correlated with cancer selected from a single nucleotide variant, an indel, or a gene fusion junction.

Once prepared, a CNV standard can contain one or more copy number variations (CNV) that can be titrated to mimic an expected concentration of the CNV in a test sample. Additionally, an SNV standard can contain one or more SNVs that can be titrated to mimic an expected concentration of the SNV in a test sample. If a set of such standards are prepared, each having at least one CNV standard composition combined with at least one SNV standard composition having at least one SNV, the resulting set of genetic nucleic acid standards provides a powerful tool to analyze various test samples, particularly cancer test samples, such as tumor samples and especially plasma samples suspected of containing circulating tumor DNA. Optionally, the set of genetic standards (e.g., the combination of at least one CNV genetic standard and at least one SNV genetic standard) can be prepared to detect and/or identify related genetic conditions. On the other hand, a SNV nucleic acid standard having 10, 20, 30, 40, 50, or more SNVs can be combined with at least one CNV genetic standard as controls in methods related to cancer diagnostics, such as methods for detecting circulating tumor DNA.

The set of genetic standards can contain a plurality of known CNV and SNV variants that can be prepared in any desired ratio or percentage allele frequency to correlate to, or match specific tumor content, or especially circulating tumor DNA content. The combined genetic standards having both a SNV and CNV variant can be, for example, titrated against a reference sample (such as a WT cell line) or matched non-cancer cell line to assist in the detection of one or more CNVs or SNVs in a single sample. In another configuration, the set of genetic standards is provided as a set of nucleic acid standards, where the set includes between 2 and 250 nucleic acid standards, and where at least one nucleic acid standard detects a CNV variant and at least one nucleic acid standard detects a SNV variant.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the methods, compositions described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A kit, comprising two or more nucleic acid standard compositions for analyzing circulating tumor DNA, each standard composition comprising a mixture of a first nucleosomal ladder nucleic acid preparation generated in vitro from a cancer cell source and a second nucleosomal ladder nucleic acid preparation generated in vitro from a matched non-cancer cell source, wherein the first nucleosomal ladder nucleic acid preparation and the second nucleosomal ladder nucleic acid preparation are generated in vitro by MNase treatment, wherein the ratio of the quantity of the first nucleosomal ladder nucleic acid preparation and the quantity of the second nucleosomal ladder nucleic acid preparation in each nucleic acid standard composition is different, wherein the first nucleosomal ladder nucleic acid preparation comprises between 0.01% to 20% of the total nucleosomal nucleic acids in at least two of the nucleic acid standard compositions, and wherein a copy number of a chromosomal region known to exhibit copy number variation in cancer is different in the first nucleosomal ladder nucleic acid preparation compared to the second nucleosomal ladder nucleic acid preparation.

2. The kit of claim 1, wherein the kit comprises between 2 and 20 nucleic acid standard compositions.

3. The kit of claim 1, wherein the kit comprises between 5 and 10 nucleic acid standard compositions.

4. The kit of claim 1, wherein the kit comprises at least one nucleic acid standard composition in which the quantity of the first nucleosomal ladder nucleic acid preparation comprises between 0.01% to 10% of the total nucleic acids of the nucleic acid standard composition.

5. The kit of claim 1, wherein the kit comprises at least two nucleic acid standard composition in which the quantity of the first nucleosomal ladder nucleic acid preparation comprises between 0.01% to 1% of the total nucleic acids of the nucleic acid standard composition.

6. The kit of claim 1, wherein the kit comprises at least two nucleic acid standard composition in which the quantity of the first nucleosomal ladder nucleic acid preparation comprises between 1% to 10% of the total nucleic acids of the nucleic acid standard composition.

7. The kit of claim 1, wherein at least one of the nucleic acid standard compositions further comprises between 0.01 and 10% of total nucleic acids in the nucleic acid standard composition, of a synthetic oligonucleotide between 50 and 500 base pairs in length comprising at least 50 contiguous nucleotides having a sequence that is at least 90% identical to a genomic sequence comprising or flanking a mutation correlated with cancer selected from a single nucleotide variant, an indel, or a gene fusion junction.

8. A kit comprising:
(a) two or more nucleic acid standard compositions each in a separate chamber, tube, or vessel and each standard composition comprising a mixture of a first nucleosomal ladder nucleic acid preparation generated in vitro from a cancer cell source and a second nucleosomal ladder nucleic acid preparation generated in vitro from a matched non-cancer cell source, wherein the first nucleosomal ladder nucleic acid preparation and the second nucleosomal ladder nucleic acid preparation are generated in vitro by MNase treatment, wherein the ratio of the quantity of the first nucleosomal ladder nucleic acid preparation and the quantity of the second nucleosomal ladder nucleic acid preparation in each nucleic acid standard composition is different, wherein the first nucleosomal ladder nucleic acid preparation comprises between 0.01% to 20% of the total nucleosomal nucleic acid in at least two of the nucleic acid standard compositions, and wherein a copy number of a chromosomal region known to exhibit copy number variation in cancer is different in the first nucleosomal ladder nucleic acid preparation compared to the second nucleosomal ladder nucleic acid preparation; and
(b) one or more primers for amplifying at least a portion of the chromosomal region known to exhibit copy number variation in cancer.

9. The kit of claim 8, wherein the kit comprises at least one nucleic acid standard composition in which the quantity of the first nucleosomal ladder nucleic acid preparation comprises between 0.01% and 1% of the total nucleic acids of the nucleic acid standard composition preparations.

* * * * *

SEQUENCE LISTING

```
<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tacctctatt gttggatcat attc                                              24

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
taatatagtc acattttcat tatttttat                                         29

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
accctgggca accagccctg t                                                 21

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccacaccccc gcccggcac                                                    19
```

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcgtggtgag gctccccttt ct                                              22

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gacctgattt ccttactgcc tcttg                                           25

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cactgacaac caccctta ac c                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccctcctcag catcttatcc g                                               21

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
accaccacac tatgtcgaaa ag                                              22

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggagagacg acagggctg                                                  19

```
<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccagtgtgca gggtggcaag                                               20

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcctgtgtt atctcctagg ttg                                           23

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atgcaggggg atacggcca                                                19

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgtcatcttc tgtcccttcc cag                                           23

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gaaaggtgat aaaagtgaat ctgag                                         25

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggagagaccg gcgcacag                                                 18
```